United States Patent [19]
Cho et al.

[11] Patent Number: 6,066,630
[45] Date of Patent: May 23, 2000

[54] CEPHALOSPORIN ANTIBIOTICS

[75] Inventors: In-Seop Cho, Mountain View; Scott J. Hecker, Los Gatos; Tomaz W. Glinka, Sunnyvale; Ving J. Lee, Los Altos; Zhijia J. Zhang, Foster City, all of Calif.

[73] Assignee: Microcide Pharmaceuticals, Inc., Mountain View, Calif.

[21] Appl. No.: 08/728,232

[22] Filed: Oct. 11, 1996

Related U.S. Application Data

[60] Provisional application No. 60/005,389, Oct. 12, 1995.

[51] Int. Cl.$^7$ ...................... A61K 31/545; C07D 501/59; C07D 501/24
[52] U.S. Cl. ........................... 514/203; 514/204; 514/206; 514/208; 540/224; 540/225; 540/226; 540/227; 540/229
[58] Field of Search ................................ 540/227, 224, 540/225, 226, 229; 514/206, 203, 204, 208

[56] References Cited

U.S. PATENT DOCUMENTS

| | | | |
|---|---|---|---|
| 3,992,377 | 11/1976 | Chauvette et al. | 260/243 C |
| 4,256,739 | 3/1981 | Woodward et al. | 544/17 |
| 4,307,116 | 12/1981 | Farge et al. | 514/206 |
| 4,415,562 | 11/1983 | Farge et al. | 514/203 |
| 4,584,290 | 4/1986 | Takaya et al. | 514/206 |
| 4,870,168 | 9/1989 | Baker et al. | 540/222 |
| 5,025,006 | 6/1991 | Dinninno et al. | 514/210 |
| 5,077,287 | 12/1991 | Temansky | 514/210 |

FOREIGN PATENT DOCUMENTS

| | | |
|---|---|---|
| 0527686 | 2/1993 | European Pat. Off. . |
| 9507283 | 3/1995 | WIPO . |
| 9526966 | 10/1995 | WIPO . |

OTHER PUBLICATIONS

Ege, "Organic Chemistry" (Heath & Co) p. 98, 1984.
Bruice, "Organic Chemistry, 2nd Ed" (Prentice Hall) pp. 53,63,1083, 1998.
Barrett, "Amide Transacylation in Penicillin and Cephalosporin Derivatives," *J.C.S. Perkin I* pp. 1629–1633 (1979).
Chauvette et al. "Chemistry of Cephalosporin Antibiiotics. XXI. Conversion of Penicillin to Cephalexin," *J. Org. Chem.* 36:1259–1267 (1971).
Farina et al., "A General Route to 3–Functionalized 3–Norcephalosporins," *J. Org. Chem.* 54:4962–4966 (1989).
Greene et al., *Protective Groups in Organic Synthesis*, John Wiley & Sons, New York, pp. 309–315 (1991).
Georg, *The Organic Chemistry of β–Lactams*, VCH (1992) (Table of Contents Only).
Kondo et al., "New 2''–Amino Derivatives of Arbekacin, Potent Aminoglycoside Antibiotics Against Methicillin–Resistant *Staphylococcus aureus*," *J. Antibiotics* 46:531–534 (1993).
Larock, "8. Lactone and Lactam Formation," *Comprehensive Organic Transformations*, VCH Publishers, pp. 941–962 (1992).

NCCLS publication entitled Methods For Dilution Antimicrobial Susceptibility Tests For Bacterial That Grow Aerobically—Third Edition; Approved Standard, NCCLS 13(25) (1993).
Ohki et al., "FK037. A New Parenteral Cephalosporin With a Broad Antibacterial Spectrum: Synthesis and Antibacterial Activity," *J. Antibiotics* 46:359–361 (1993).
Sanders and Sanders, "Microbiological Characterization of Everninomicins B and D," *Antimicrobial Agents and Chemotherapy* 6:232–238 (1974).
Spangler et al., "Susceptibilities of Penicillin–Susceptible and –Resistant Strains of *Streptococcus pneumoniae* to RP 59500, Vancomycin, Erythromycin, PD 131628, Sparfloxacin, Temafloxacin, Win 57273, Ofloxacin, and Ciprofloxacin," *Antimicrobial Agents and Chemotherapy* 36:856–859 (1992).
Sum et al., "Glycylcyclines. 1. A New Generation of Potent Antibacterial Agents through Modification of 9–Aminotetracyclines," *J. Med. Chem.* 37:184–188 (1994).
Ternansky et al., "Discovery and Structure–Activity Relationship of a Series of 1–Carba–1–dethiacephems Exhibiting Activity against Methicillin–Resistant *Staphylococcus aureus*," *J. Med. Chem.* 36:1971–1976 (1971).

*Primary Examiner*—Mark L. Berch
*Attorney, Agent, or Firm*—Lyon & Lyon LLP

[57] ABSTRACT

The present invention includes novel compounds of formula

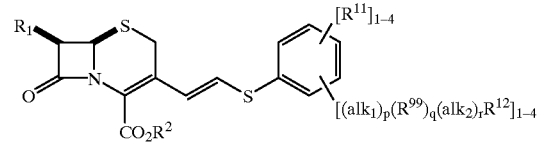

where $R^{99}$ is selected from the group consisting of sulfur, SO, $SO_2$, NH, N-alkyl, oxygen, C=C (cis or trans), and C≡C, and $R^{12}$ is

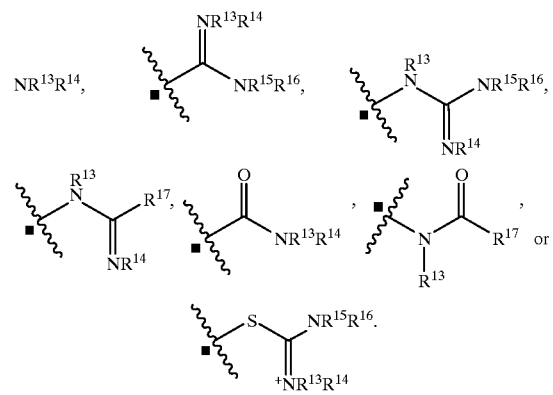

The invention also includes the pharmacologically acceptable salts which exhibit antibiotic activity against a wide spectrum of organisms including organisms which are resistant to β-lactam antibiotics and are useful as antibacterial agents. The invention also relates to novel intermediates useful for making the novel compounds of the present invention and to novel methods for producing the novel compounds and intermediate compounds.

11 Claims, 5 Drawing Sheets

PREPARING THE CEPHEM

PREPARATION OF THE C(7)SUBSTITUENT

PREPARATION OF THE 3-SUBSTITUENT

DEPROTECTION AND SALT FORMATION

CEPHALOSPORIN ANTIBIOTICS

RELATED APPLICATIONS

This application is related to and claims priority to the U.S. Provisional Application Ser. No. 60/005,389, filed Oct. 12, 1995, by Cho et al. and entitled "CEPHALOSPORIN ANTIBIOTICS" (Lyon & Lyon Docket No. 216/170), which is incorporated herein by reference in its entirety, including any drawings.

BACKGROUND OF THE INVENTION

1. Field of the Invention

The present invention relates to novel cephalosporin antibiotics and their methods of production and use. These compounds are expected to exhibit antibiotic activity against a wide spectrum of organisms, including organisms which are resistant to conventional β-lactam antibiotics.

2. Review of the Background Art

The following review of the background of the invention is merely provided to aid in the understanding of the present invention and neither it nor any of the references cited within it are admitted to be prior art to the present invention.

Over the past three decades a large variety of antibiotics have become available for clinical use. One class of antibiotics which has seen remarkable growth are the cephalosporins, over 70 of which have entered clinical use for the treatment of bacterial infections in mammals since 1965. The cephalosporins exhibit their antibacterial activity by inhibiting bacterial peptidoglycan biosynthesis, and have been extremely effective in treating a wide variety of bacterial infections. Cephalosporins that are said to have antibacterial activity are described in U.S. Pat. No. 3,992,377 and U.S. Pat. No. 4,256,739.

Unfortunately, the wide-spread and indiscriminant use of these antibiotics has led to a rapid increase in the number of bacterial strains which are resistant to these compounds. Most importantly, this resistance has emerged among clinically important microorganisms which threaten to limit the utility of presently available cephalosporin antibiotics. In particular, resistant strains of Salmonella, S. pneumoniæ, Enterobacteriaceæ, and Pseudomonas have emerged which threaten to undo many of the strides made in reducing mortality and morbidity from bacterial infections.

Bacterial resistance to cephalosporins follows three major pathways: (a) the development of β-lactamases capable of inactivating the β-lactam ring of the cephalosporin; (b) decreased cephalosporin penetration into the bacteria due to changes in bacterial cell wall composition; and (c) poor binding to penicillin-binding proteins (PBPs). The latter pathway is especially important, as the binding of β-lactams to PBPs is essential for inhibiting bacterial cell-wall biosynthesis. Certain Gram-positive bacteria, namely methicillin-resistant *Staphylococcus aureus* ("MRSA") and enterococci are highly resistant to β-lactam antibiotics. Resistance in MRSA is due to the presence of high levels of an unusual PBP, PBP2a, which is insensitive, or binds poorly, to β-lactam antibiotics. The activity of β-lactam antibiotics against PBP2a-containing organisms has been shown to correlate well with the binding affinity of the antibiotic to PBP2a. Currently, the glycopeptides vancomycin and teicoplanin are primarily used for MRSA bacteremia. The quinolone antibacterials and some carbapenems, such as imipenem, have been reported to be active against a few MRSA strains, but their use is restricted due to emerging resistant MRSA strains.

Experimental compounds which may possess utility as anti-MRSA or anti-enterococcal bactericides include the glycylcyclines (see, e.g., P.-E. Sum et al., *J. Med. Chem.*, 37, (1994)), FK-037 (see, e.g., H. Ohki et al., *J. Antibiotics*, 46:359–361 (1993)), RP-59,500 (see, e.g., S. K. Spangler et al., *Antimicro. Agents Chemother.*, 36:856–9 (1992)), the everninomycin complex (see, e.g., W. E. Sanders et al., *Antimicro. Agents Chemother.*, 6: 232–8 (1974)), the 2-(biaryl)carbapenems (see, e.g., U.S. Pat. No. 5,025,006), 3-(benzothiazolylthio)cephems (see, e.g., EP Application No. 527686), 3-(thiazolylthio)carbacephems (see, e.g., R. J. Ternansky et al., *J. Med. Chem.*, 36:1971 (1993) and U.S. Pat. No. 5,077,287) and arbekacin (S. Kondo, et al. *J. Antibiotics* 46:531 (1993).

Recent advances in the compounds, compositions and methods useful for treating infections in mammals arising from β-lactam antibiotic resistant bacteria are described in commonly owned International Publication WO 95/26966 and U.S. patent applications Ser. No. 08/222,262, filed Apr. 1, 1994, now abandoned; Ser. No. 08/369,798, filed Jan. 6, 1995, now abandoned; Ser. No. 08/413,713, now U.S. Pat. No. 5,756,493, issued May 26, 1998; Ser. No. 08/413,714, now U.S. Pat. No. 5,607,926, issued Mar. 4, 1997; Ser. No. 08/415,065, filed Mar. 29, 1995, now abandoned; Ser. No. 08/413,712, now U.S. Pat. No. 5,604,218, issued Feb. 18, 1997; Ser. No. 08/415,064, now U.S. Pat. No. 5,789,584, issued Aug. 4, 1998; Ser. No. 08/415,069, now U.S. Pat. No. 5,593,986 issued Jan. 14, 1997; Ser. No. 08/455,969, now U.S. Pat. No. 5,698,547, issued Dec. 16, 1997; and Ser. No. 08/457,673, now U.S. Pat. No. 5,688,786, issued Nov. 18, 1997; all of which are incorporated herein by reference in their entirety, including any drawings.

SUMMARY OF THE INVENTION

The present invention includes compounds, compositions and methods effective to treat infections in mammals arising from β-lactam antibiotic resistant bacteria. Preferred compounds will have a minimum inhibitory concentration (MIC) that is less that 50%, more preferably less than 10, and most preferably less than 1% of the MIC of cefotaxime or imipenem for a beta-lactam resistant organism, preferably a methicillin-resistant Staphylococcal or ampicillin-resistant Enterococcal organism. Other preferred compounds will be able to prevent or reduce mortality in mice infected with the beta-lactam resistant organism to a greater extent than cefotaxime or imipenem.

In one aspect the invention features compounds of the structures II–VI

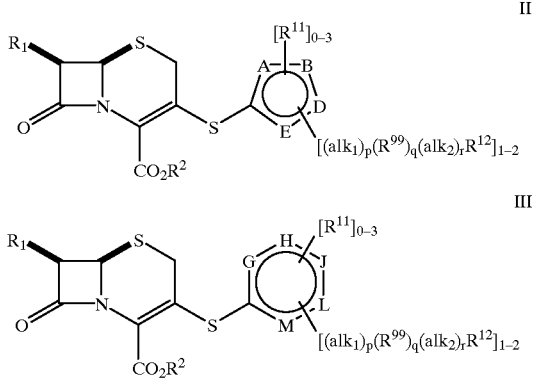

-continued

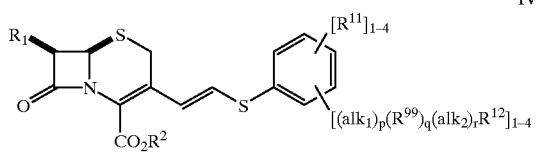

IV

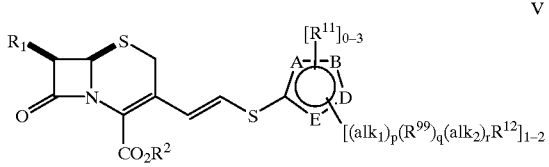

V

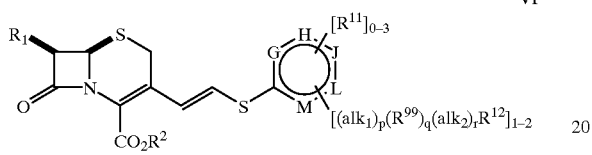

VI and/or their pharmaceutically acceptable salts and/or prodrugs, wherein $R^1$ is selected from the group consisting of

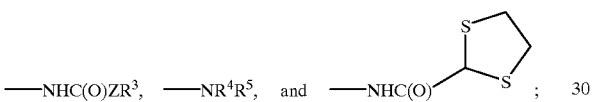

—NHC(O)ZR$^3$, —NR$^4$R$^5$, and —NHC(O)

Z is selected from the group consisting of —CH$_2$(X)$_m$—, —(NOR$^6$)—, —CH(OR$^7$)—, —C(CHCO$_2$R$^8$)— and —CH(NR$^9$R$^{10}$)—;

X is selected from the group consisting of oxygen and sulphur;

m is selected from the group consisting of 0 and 1;

$R^3$ is selected from the group consisting of cyano, alkyl, aryl, heterocycle (wherein said heterocycle is optionally substituted and preferably is disubstituted with NH$_2$ and halogen (preferably chlorine)), heteroaralkyl and (CH$_2$)$_n$T, n is 1 to 6, T is selected from the group consisting of amino, amidino (C- or N-linked), guanidino, and isothioureido, optionally substituted by alkyl, aryl, hydroxyl, or amino;

$R^{4-7}$ are independently selected from the group consisting of hydrogen, alkyl, aryl and acyl;

$R^8$ is selected from the group of hydrogen, alkyl and aryl;

$R^9$ and $R^{10}$ are selected independently from the group consisting of hydrogen, alkyl, acyl, and heterocyclecarbonyl;

$R^2$ is selected from the group consisting of hydrogen, alkyl, alkenyl, aryl, heterocycle, aralkyl, heteroaralkyl, and trialkylsilyl; or $R^2$ is not present and the CO$_2$ group to which it would be attached bears a negative charge.

A, B, D, and E are selected from the group consisting of carbon, nitrogen and sulphur and the specific juxtaposition of groups A, B, D and E is limited to examples of heterocyclic groups known in the chemistry arts;

G, H, J, L and M are carbon, nitrogen or $^+$NR$^{11}$ (quaternary ammonium heterocycle) and the specific juxtaposition of groups G, H, J, L and M is limited to examples of heterocyclic groups known in the chemistry arts;

$R^{11}$ is selected from the group consisting of H, halogen, alkyl, alkoxy, hydroxyl, amino, cyano, hydroxyalkyl, carboxamidoalkyl, optionally substituted aminoalkyl or quaternary ammonium alkyl, and quaternary heteroaryliumalkyl;

alk$_1$ and alk$_2$ are alkyl groups and are independently and optionally substituted with a substitutent selected from the group consisting of alkyl, hydroxyl, optionally substituted amino, alkoxy, hydroxyalkyl and optionally substituted carboxamide;

p is 0, 1, or 2;

$R^{99}$ is selected from the group consisting of sulfur, SO, SO$_2$, NH, N-alkyl, oxygen, C=C (cis or trans), and C≡C;

q is 0 or 1;

r is 0, 1, 2 or 3;

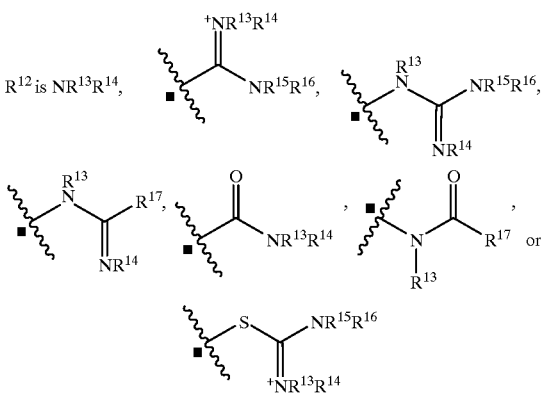

$R^{13}$–$R^{16}$ are independently selected from the group consisting of H, hydroxy, amino, amidino, alkyl, cycloalkyl, acyl, aminoacyl, and phosphoryl and taken together may form a 5- or 6-membered ring; and $R^{17}$ is H or alkyl;

wherein alk$_2$ and $R^{12}$ taken together may form an optionally substituted 5 or 6 member non-aromatic heterocycle.

Specific examples of heterocyclic groups known in the chemistry arts include the following (shown linked to a sulfur atom in each case, as above):

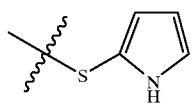 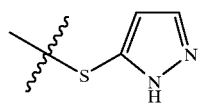

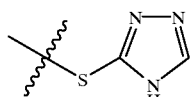 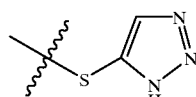

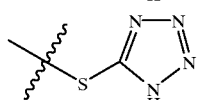 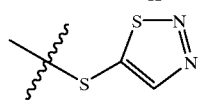

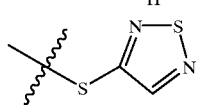 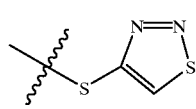

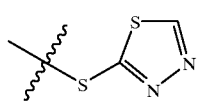 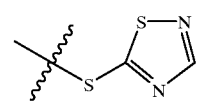

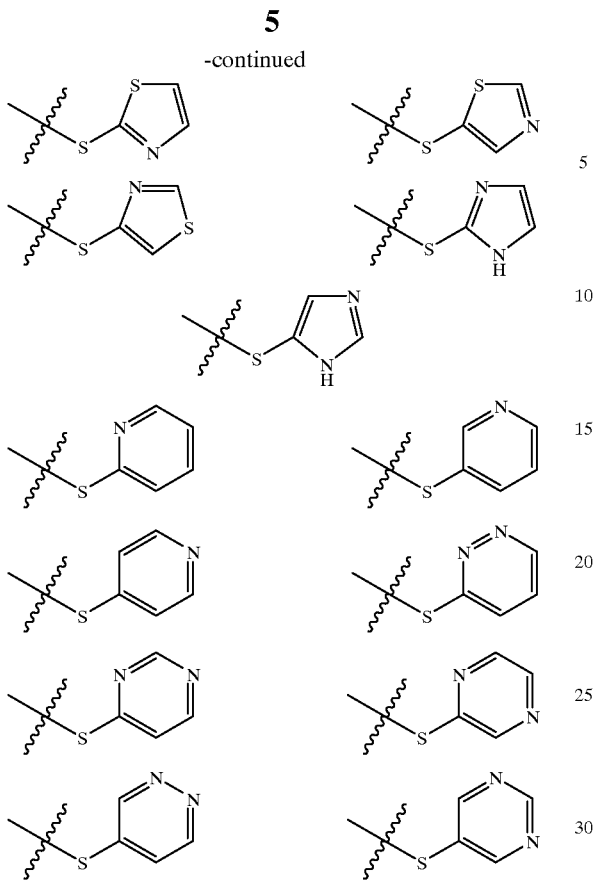

Structures IV, V and VI show a vinyl group linking the cephem nucleus to an arylthio or heteroarylthio group. It is to be understood that each carbon atom of the vinyl group may optionally in addition be substituted by a lower alkyl group, such as a methyl or ethyl group.

Preferred compounds include those compounds wherein $R^{11}$ is H or halogen, $R^{12}$ is $NR^{13}R^{14}$,

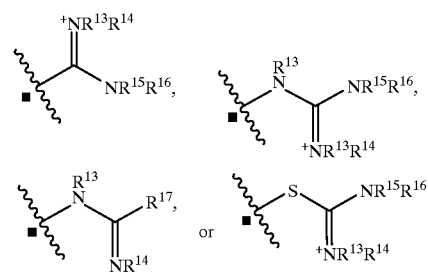

p is 0 or 1, q is 0 or 1, r is 1, 2 or 3, $R^{13}$–$R^{16}$ are H or lower alkyl, and $R^{17}$ is H or lower alkyl. Especially preferred compounds include those compounds wherein $R^{11}$ is hydrogen, $R^{12}$ is $NR^{13}R^{14}$,

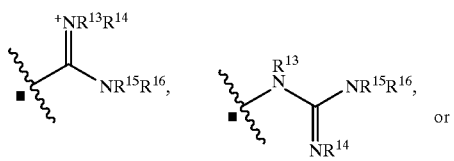

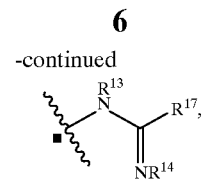

are hydrogen, and $R^{17}$ is hydrogen or lower alkyl. There are preferably one or two $[(CH_2)_p(S)_q(CH_2)_rR^{12}]$ groups present. There are preferably three or four $R^{11}$ groups present.

Preferred compounds include those wherein:

(1) $R^1$ is $NHC(O)ZR^3$
Z is —$CH_2(X)_m$—
X is S
m is 1

(2) $R^1$ is $NHC(O)ZR^3$
Z is —$C(NOR^6)$—
$R^6$ is selected from the group consisting of hydrogen, methyl, 2-fluoroethyl, cyclopropylmethyl, allyl, dichloroallyl and cyclopentyl, and $R^3$ is selected from the group consisting of phenyl, 2-thienyl, 2-furyl, 2-aminothiazol-4-yl, 2-amino-5-chlorothiazol-4-yl, and 2-aminothiadiazol-4-yl;

(3) $R^{11}$ is H or halogen (4) $R^{12}$ is $NR^{13}R^{14}$,

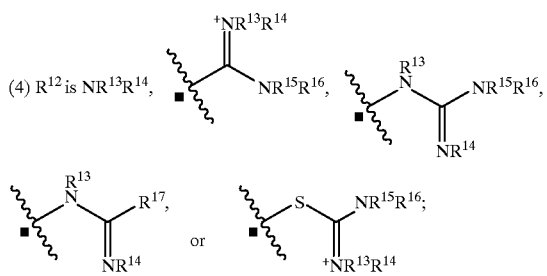

(5) p is 0 or 1
q is 0 or 1
r is 1, 2 or 3; and/or (6) $R^{13}$–$R^{17}$ are H or lower alkyl.

Preferred compounds include those wherein $alk_2$ and $R^{12}$ taken together an optionally substituted 5 or 6 member carbon ring containing a single nitrogen. In especially preferred embodiments, $alk_2$ and $R^{12}$ taken together form a substitutent (shown below on a sulfur atom) selected from the group consisting of

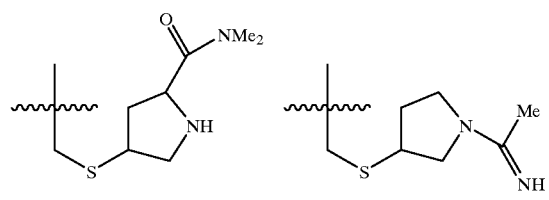

Other preferred examples are shown below linked through a sulfur atom to a 4-pyridyl substituent:

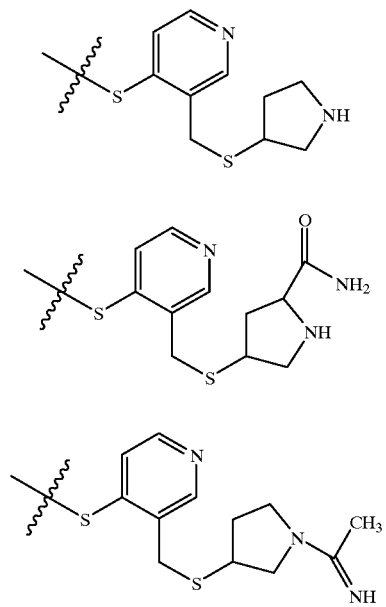

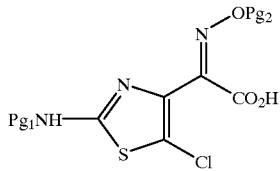

Other features and advantages of the invention will be apparent from the following description of the preferred embodiments thereof and from the claims.

BRIEF DESCRIPTION OF THE DRAWINGS

FIG. 1 shows preparation of the cephem.

FIG. 2 shows preparation of the C(7)-substituent.

FIG. 3 shows preparation of the 3-substituent.

FIG. 4 shows the final assembly.

FIG. 5 shows deprotection and salt formation.

DESCRIPTION OF THE PREFERRED EMBODIMENTS

I. Definitions

Figure 1:
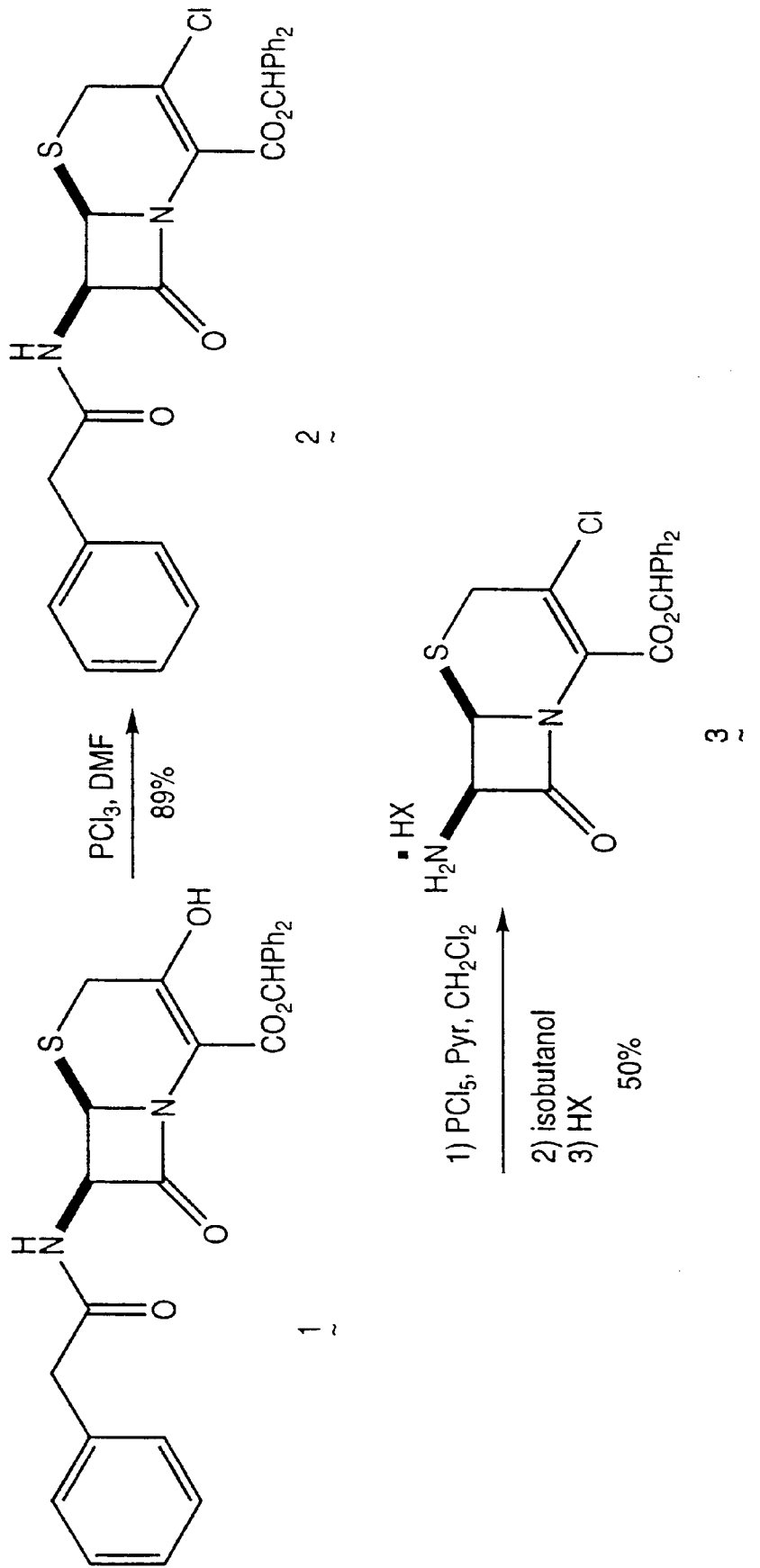
FIGS. 1–5 show preferred synthetic schemes for producing compounds of the present invention.

As used herein, the term "alkyl" denotes branched or unbranched hydrocarbon chains, preferably containing between one and six, more preferably one and four, carbon atoms, such as, e.g., methyl, ethyl, n-propyl, iso-propyl, n-butyl, sec-butyl, iso-butyl, tert-butyl, and 2-methylpentyl. These groups may be optionally substituted with one or more functional groups which are attached commonly to such chains, such as, e.g., hydroxyl, bromo, fluoro, chloro, iodo, mercapto or thio, cyano, alkylthio, heterocycle, aryl, heteroaryl, carboxyl, alkoxycarbonyl, alkyl, alkenyl, nitro, amino, alkoxyl, amido, and optionally substituted isothioureido, amidino, guanidino, and the like to form alkyl groups such as trifluoromethyl, 3-hydroxyhexyl, 2-carboxypropyl, 2-fluoroethyl, carboxymethyl, 4-cyanobutyl, 2-guanidinoethyl, 3-N,N'-dimethylisothiouroniumpropyl, and the like.

The term "alkenyl" denotes an alkyl group as defined above having at least one double bond, e.g., allyl, 3-hydroxy-2-buten-1-yl, 1-methyl-2-propen-1-yl and the like.

The term "aryl" denotes a chain of carbon atoms an which form an least one aromatic ring having preferably between about 6–14 carbon atoms, such as, e.g., phenyl, naphthyl, indenyl, and the like, and which may be substituted with one or more functional groups which are attached commonly to such chains, such as, e.g., hydroxyl, bromo, fluoro, chloro, iodo, mercapto or thio, cyano, cyanoamido, alkylthio, heterocycle, aryl, heteroaryl, carboxyl, alkoxycarbonyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, Without being bound to any particular theory regarding operation of the invention, it is noted that there are several novel structural features of the invention which are believed to contribute to the substantially improved functional properties. In particular, chlorine substituents on heterocyclic $R^3$ groups appear to impact 2–4 fold improved MIC values compared to the compounds with non-chlorinated heterocyclic $R^3$ groups.

Preferred pharmaceutically acceptable salts include (1) inorganic salts such as chloride, bromide, iodide, nitrate, phosphate or sulfate; (2) carboxylate salts such as acetate, propionate, butyrate, maleate, or fumarate; (3) alkylsulfonates such as methanesulfonate, ethanesulfonate, 2-hydroxyethylsulfonate, n-propylsulfonate or iso-propylsulfonate; and (4) hydroxycarboxylates such as lactate, malate, and citrate.

In another embodiment, the present invention provides for compositions comprising an amount of a compound of Structure II, III, IV, V or VI effective to treat bacterial infections in mammals arising from bacteria resistant to β-lactam antibiotics.

In still another embodiment, the present invention includes methods for treating a bacterial infection in a mammal arising from bacteria resistant to β-lactam antibiotics comprising administering to a mammal suffering from such an infection a therapeutically effective amount of a compound of Structure II, III, IV, V or VI. Of course, the compounds of the present invention also have utility in compositions and methods to treat mammals infected with bacteria that are sensitive to conventional β-lactam antibiotics.

In another embodiment, this invention features compounds and methods for preparation of an intermediate VII, which is useful for preparing compounds having particularly potent activity against methicillin-resistant Staphylococci and ampicillin-resistant Enterococci.

oxazolylphenyl, imidazolylphenyl, imidazolylmethylphenyl, cyanophenyl, pyridylphenyl, pyrrolylphenyl, pyrazolylphenyl, triazolylphenyl, tetrazolylphenyl and the like.

The term "heterocycle" denotes a chain of carbon and at least one non-carbon atoms which together form one or more aromatic or non-aromatic rings having preferrably between about 6–14 atoms, such as, e.g., furyl, thienyl, imidazolyl, indolyl, pyridinyl, thiadiazolyl, thiazolyl, piperazinyl, dibenzfuranyl, dibenzthienyl. These rings may be optionally substituted with one or more functional groups which are attached commonly to such rings, such as, e.g., hydroxyl, bromo, fluoro, chloro, iodo, mercapto or thio, cyano, cyanoamido, alkylthio, heterocycle, aryl, heteroaryl, carboxyl, oxo, alkoxycarbonyl, alkyl, alkenyl, nitro, amino, alkoxyl, amido, and the like to form rings such as, e.g., 2-aminothiazol-4-yl, 2-amino-5-chlorothiazol-4-yl, 2-amino-thiadiazol-4-yl, 2,3-dioxopiperazinyl, 4-alkylpiperazinyl, 2-iodo-3-dibenzfuranyl and 3-hydroxy-4-dibenzthienyl and the like.

The term "heteroaromatic" or "heteroaryl" (HetAr) denotes an aromatic heterocycle as defined above.

The term "heterotricycle" denotes an aromatic heterocyclic substituent as defined above which comprises three aromatic rings.

The term "heterocyclecarbonyl" denotes the group —C(O)Het, where Het is heterocycle as defined above.

The term "alkoxyl" denotes the group —OR, where R is alkyl as defined above, such as methoxy, ethoxy, n-propoxy, iso-propoxy, n-butoxy, sec-butoxy, iso-butoxy, tert-butoxy, trifluoromethoxy, 3-hydroxyhexyloxy, 2-carboxypropyloxy, 2-fluoroethoxy, carboxymethoxy and cyanobutyloxy and the like.

The term "alkylthio" denotes the group —SR, where R is alkyl as defined above, such as methylthio, ethylthio, n-propylthio, iso-propylthio, n-butylthio, sec-butylthio, iso-butylthio, tert-butylthio, trifluoromethylthio, 3-hydroxyhexylthio, 2-carboxypropylthio, 2-fluoroethylthio, carboxymethylthio and cyanobutylthio and the like.

The term "acyl" denotes groups —C(O)R, where R is alkyl as defined above, such as formyl, acetyl, propionyl, or butyryl.

The term "aryloxy" denotes groups —OAr, where Ar is an aryl group as defined above.

The term "aralkyl" denotes groups —RAr, where R is alkyl and Ar is aryl, both as defined above.

The term "heteroaralkyl" denotes groups —RHetAr where R is alkyl and HetAr is heteroaryl as defined above.

The term "trialkylsilyl" denotes the group RR'R"Si—, where R, R' and R" are alkyl as defined above.

The term "trialkylammonium" denotes the group [RR'R"N—]⁺, where R, R' and R" are alkyl as defined above.

The term "amino" denotes the group NRR', where R and R' may independently be alkyl, aryl or acyl as defined above, or hydrogen.

The term "carboxamido" denotes the group —C(O)NRR', where R and R' may independently be alkyl, aryl or acyl as defined above, or hydrogen.

The term "cyanoamido" refers to the group —NH—C≡N.

The term "β-lactam resistant bacteria" refers to bacteria against which a β-lactam antibiotic has an minimum inhibitory concentration (MIC) greater than 32 mg/ml.

The term "methicillin-resistant bacteria" refers to bacteria that are resistant to methicillin. Examples of such bacteria are provided in Table 1 and are identified Meth$^R$. The term "methicillin sensitive bacteria" refers to bacteria that are sensitive to methicillin. Examples of such bacteria are provided in Table 1 and are identified Meth$^s$.

The term "prodrug" refers to an agent that is converted into the parent drug in vivo. Prodrugs may be easier to administer than the parent drug in some situations. For example, the prodrug may be bioavailable by oral administration but the parent is not, or the prodrug may improve solubility to allow for intravenous administration.

II. Compounds of the Invention

The present invention provides compounds, methods and compositions effective to treat bacterial infections, and, especially, infections arising from bacteria which have developed resistance to conventional β-lactam antibiotics. More importantly, the present invention provides compounds, methods and compositions effective to treat bacterial infections arising from bacteria which have developed resistance to conventional cephalosporin antibiotics.

A. Synthesis of Compounds of Structure II

The compounds of the present invention may be readily prepared in accordance with the following schemes. However, it will be appreciated that other synthetic pathways for forming the compounds of the invention are available and that the following is offered merely by way of example, and not limitation. It will be further recognized that various protecting and deprotecting strategies will be employed which are standard in the art (see, e.g., Green and Wuts). Those of skill in the art will recognize that the selection of any particular protecting group (e.g., a carboxy protecting group) will depend on the stability of the protected moiety with respect to subsequent reaction conditions.

Generally, the synthesis of the cephalosporins of the present invention may be achieved using well-known methods and readily available materials (see, e.g., March; Larock, COMPREHENSIVE ORGANIC TRANSFORMATIONS (VCH Publishers, 1989); and G. I. Georg, THE ORGANIC CHEMISTRY OF β-LACTAMS, (VCH 1992), each of which is incorporated herein by reference). As shown below in Scheme 1, treatment of the cephem triflate 1 with the desired optionally protected thiolate nucleophile 2, using standard methods such as those described in Farina et al., *J. Org. Chem*, 54:4962 (1989) and U.S. Pat. No. 4,870,168 to Baker, et al., (both of which are incorporated herein by reference), provides the 3-thio derivative 3. Subsequent deprotection using procedures known to those skilled in the art affords the biologically active 4-carboxycephem 4.

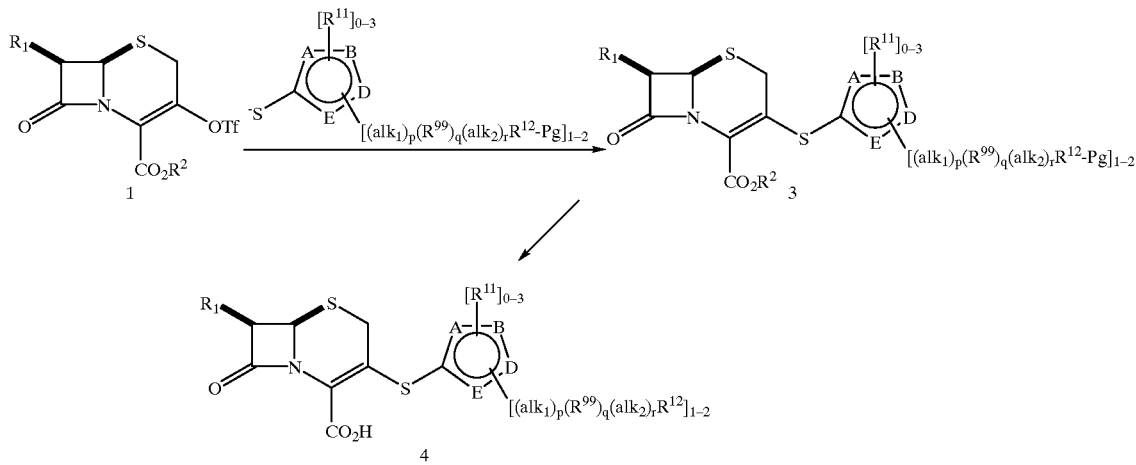

Compound 1 is formed readily from commercially available starting materials, such as the reaction of (7R)-7-[(phenylacetyl)amino]-3-hydroxy-3-cephem-4-carboxylic acid (Otsuka Chemical Co., Ltd., Otsuka, Japan) with triflic anhydride (Aldrich, Milwaukee, Wis.), using known procedures (see, e.g., Farina; and U.S. Pat. No. 4,870,168 to Baker, et al.) Other 3-hydroxy-3-cephems may be formed from the ozonolysis of 3-exomethylene cephems using known procedures (see, e.g., Farina). Similarly, the thiolate nucleophile 2 may be formed using known procedures and commercially available starting materials.

The substituent $R^1$ may be any of the groups described above and are either available commercially (e.g., from Aldrich, Milwaukee, Wis.) or can be formed using known techniques and starting materials (see, e.g., March; Larock). These groups can be substituted for those present on the starting material by variety of well known techniques (see, e.g., Barrett, J. C. S. Perkin I, 1629 (1979) or Chauvette, J. Org. Chem. 36:1259 (1971), both of which are incorporated herein by reference), such as by transamination of an existing substituent for the desired substituent, or hydrolytic removal of the existing substituent followed by reaction with a suitably reactive form of desired substituent, such as an acyl chloride. Again, the appropriate reagents and techniques will be apparent to those of skill in the art.

The carboxyl group $R^2$ may be those protecting groups amenable to reductive cleavage, such as benzyl, p- or o-nitrobenzyl, 2,2,2-trichloroethyl, allyl, cinnamyl, benzhydryl, 2-chloroallyl and the like. Alternatively, $R^2$ may be a protecting group amenable to acidic cleavage, such as t-butyl, t-amyl, trityl, 4-methoxytrityl, 4,4'-dimethoxytrityl, trimethylsilyl, t-butyldimethylsilyl, phenacyl, β-(trimethylsilyl)ethyl, benzyl, 4-(or 2-methoxybenzyl, 2,4-dimethoxybenzyl, 3,4-dimethoxybenzyl, 2,4,6-trimethoxybenzyl, methoxymethyl, benzhydryl, or 3,3-dimethylallyl. Preferred protecting groups are p-methoxybenzyl, p-nitrobenzyl, allyl and benzhydryl. Such groups may be attached to the unprotected carboxyl group of the cephalosporin starting material using known reagents and techniques, such as those described in Green and Wuts.

B. Synthesis of Compounds of Structure III

Figure 4:
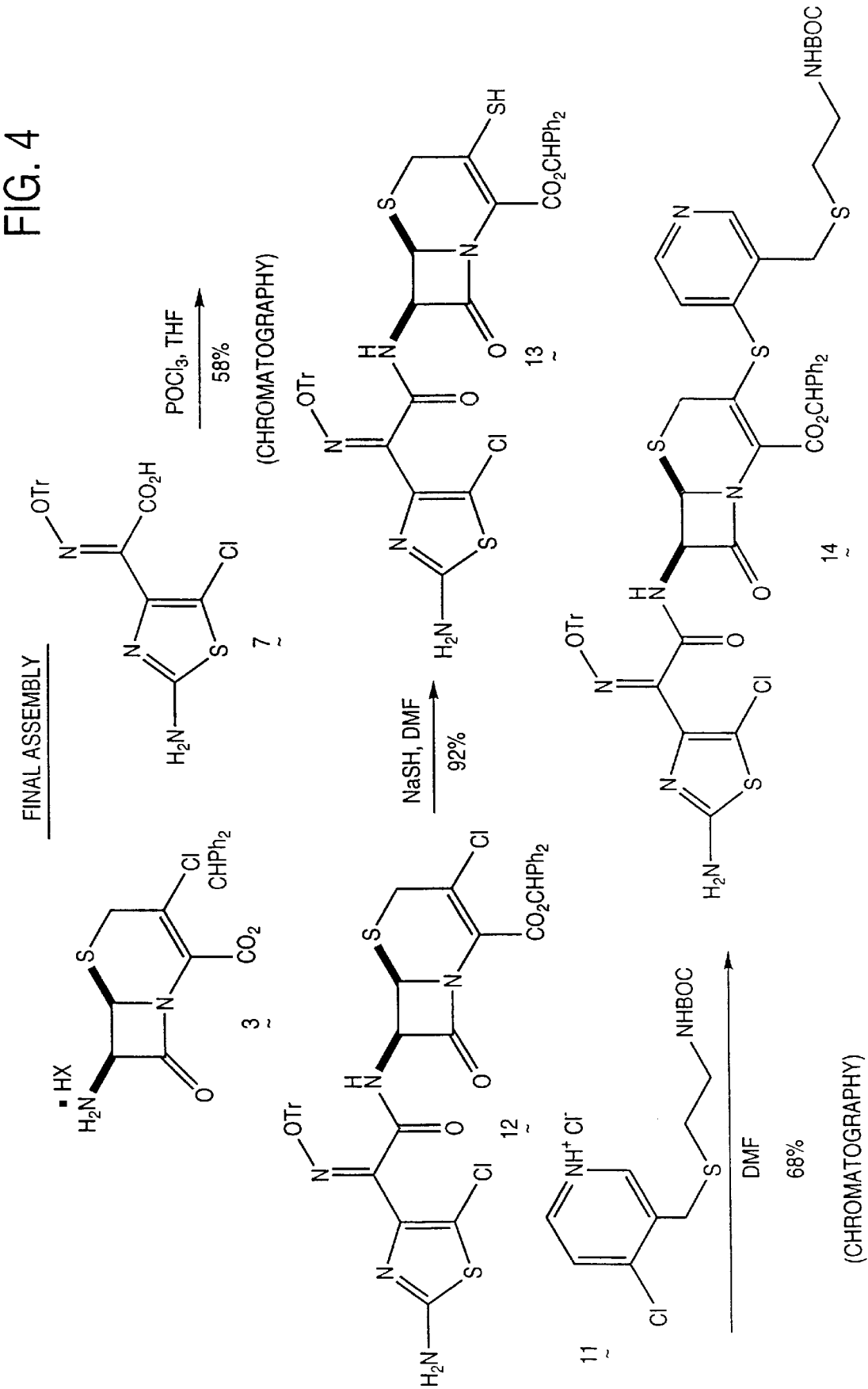
Figure 5:
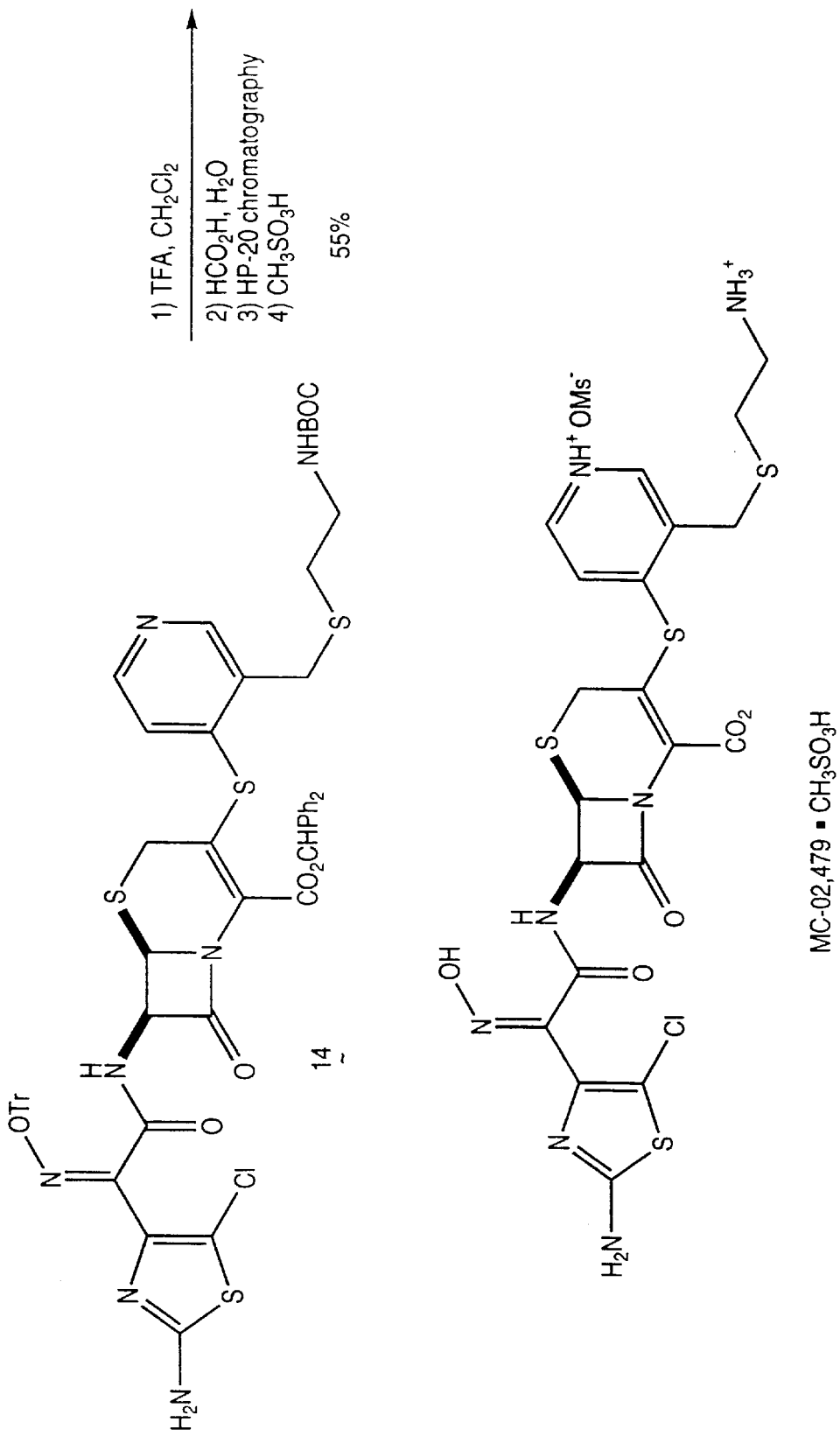

The compounds of general structure III are prepared similarly to those of general structure II. In most cases, a key step is the coupling of a substituted heteroarylthiolate with cephem triflate 1 or a functionally equivalent cephem having an alternative leaving group at C-(3). Compounds of structure III where the ring containing G, H, J, L and M is 4-pyridyl may also be prepared as exemplified in FIG. 4.

C. Synthesis of Compounds of Structures IV, V and VI

The compounds of general structure IV, V and VI are prepared by coupling an aromatic or heteroaromatic thiolate with tosylvinyl cephem sulfoxide 6. Compound 6 is formed readily from commercially available starting materials using known procedures (see, e.g., Farge et al., U.S. Pat. No. 4,307,116). The requisite aromatic or heteroaromatic thiols are prepared by a variety of methods known in the literature, as described in the Examples. As shown below in Scheme 2, treatment of the cephem intermediate 6 with a desired optionally protected thiolate nucleophile, such as 5, using methods such as those described in Farge et al., U.S. Pat. No. 4,307,116 (which is incorporated herein by reference), provides the 3-thiovinyl derivative 7. Sulfoxide reduction and subsequent deprotection using procedures known to those skilled in the art affords the biologically active 4-carboxycephem 8.

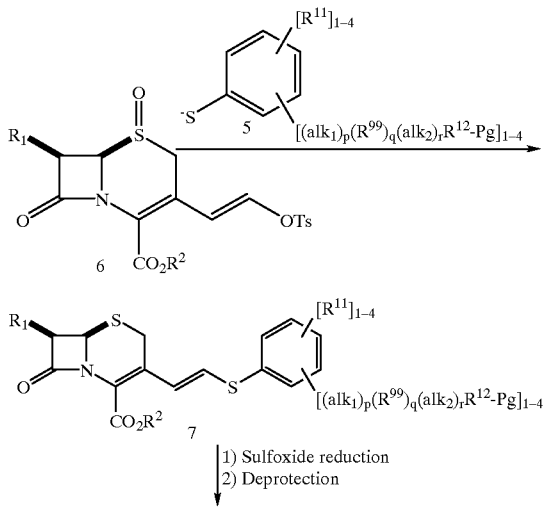

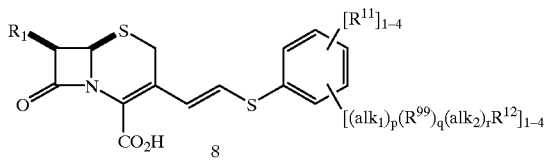

8

D. Synthesis of Compounds of Structure VII

Figure 2:
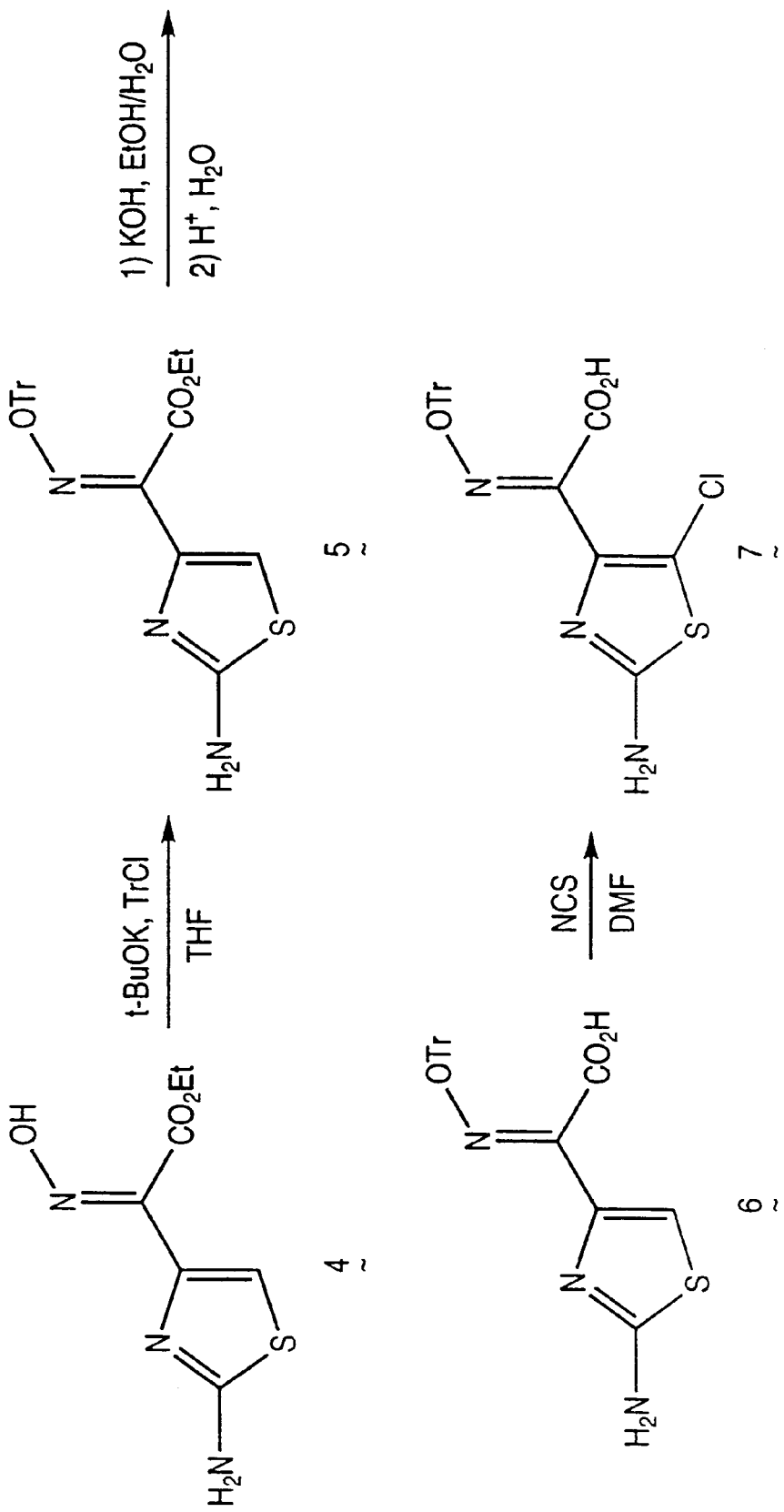
Figure 3:
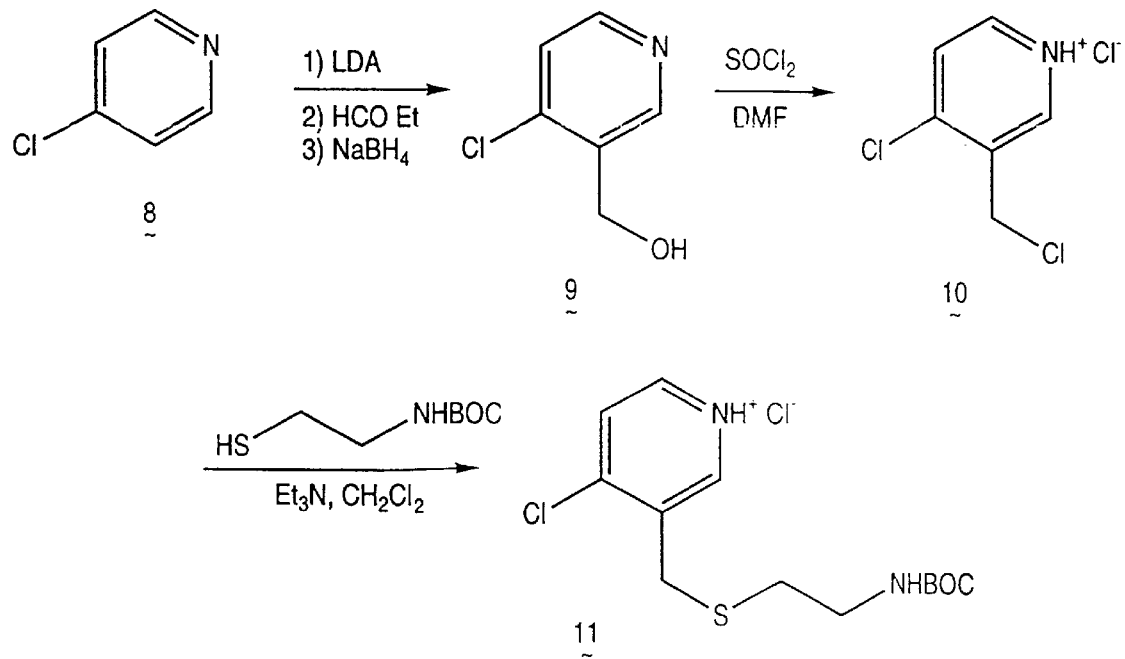

A preferred synthetic route for preparation of these intermediates is set forth in FIG. 2. In particular, the step of converting 6 to 7 shown in FIG. 2 and described in Example 18 is especially useful in providing compounds having substantially improved activity against methicillin-resistant and ampicillin-resistant bacteria.

III. Pharmaceutical Applications and Preparations

According to this invention, a therapeutically or pharmaceutically effective amount of a cephalosporin and particularly, a compound of Structure II, III, IV, V or VI, is administered to a mammal suffering from an methicillin-resistant bacterial infection (or other β-lactam resistant bacterial infections, such as vancomycin-resistant or ampicillin-resistant infections), especially resistant $S.$ $aureus$, in an amount effective to at least partially relieve the infection. Especially important are infections resulting from strains having similar activity to strains such as $S.$ $aureus$ Col (Meth$^R$) (lac$^-$), $S.$ $aureus$ 76 (Meth$^R$) (lack), $E.$ $fæcium$ ATCC 35667, or $E.$ $fæcalis$ ATCC 29212. Again, such compounds are also effective against bacteria sensitive to methicillin, vancomycin, and/or ampicillin and therefore have utility in such compositions and methods.

The compositions containing the compound(s) of the invention can be administered for prophylactic and/or therapeutic treatments. In therapeutic applications, the compositions are administered to a patient already suffering from an infection, as described above, in an amount sufficient to cure or at least partially arrest the symptoms of the infection. An amount adequate to accomplish this is defined as "therapeutically effective amount or dose." Amounts effective for this use will depend on the severity and course of the infection, previous therapy, the patient's health status and response to the drugs, and the judgment of the treating physician. In prophylactic applications, compositions containing the compounds of the invention are administered to a patient susceptible to or otherwise at risk of a particular infection. Such an amount is defined to be a "prophylactically effective amount or dose." In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the compound of the invention will be in the range of 0.1 to 1000 milligram (mg) per recipient per day, preferably in the range of 1 to 100 mg per day. The desired dosage is preferably presented in one, two, three, four or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 250 mg/kg of patient body weight, between about one to four times per day.

While it is possible to administer the active ingredient of this invention alone, it is preferable to present it as part of a pharmaceutical formulation. The formulations of the present invention comprise at least one compound or inhibitor of this invention in a therapeutically or pharmaceutically effective dose together with one or more pharmaceutically or therapeutically acceptable carriers. Solid carriers inlcude, e.g., starch, lactose, dicalcium phosphate, microcrystalline cellulose, sucrose, and kaolin, and optionally other therapeutic ingredients. Liquid carriers include, e.g., sterile water, polyethylene glycols, non-ionic surfactants, and edible oils such as corn, peanut and sesame oils. In addition, various adjuvants such as are commonly used in the art may be included. For example: flavoring agents, coloring agents, preservatives, and antioxidants, e.g., vitamin E, ascorbic acid, BHT and BHA. Various other considerations are described, e.g., in Gilman et al. (eds) (1990) Goodman and Gilman's: The Pharmacological Basis of Therapeutics, 8th Ed., Pergamon Press; and Remington's supra. Methods for administration are discussed therein, e.g., for oral, intravenous, intraperitoneal, or intramuscular administration, and others. Pharmaceutically acceptable carriers will include water, saline, buffers, and other compounds described, e.g., in the MERCK INDEX, Merck & Co., Rahway, N.J. Generally, preferred routes of administration are intravenous and intraperitoneal.

These pharmacological agents can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Generally, a pharmacologically acceptable salt of the compound will be used to simplify preparation of the composition. Preferred salts include sodium, potassium, arginine, glycine, alanine, threonine. These are prepared, preferably, in water suitably mixed with a surfactant such as hydroxypropylcellulose.

Depending on the specific conditions being treated, such agents may be formulated and administered systemically or locally. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular subcutaneous, intramedullary injections, as well an intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

In soft capsules, the active compounds may be dissolved or suspended in suitable liquids, such as fatty oils, liquid paraffin, or liquid polyethylene glycols. In addition, stabilizers may be added.

IV. Biological Activity

In Vitro Antibacterial Evaluation

The compounds of the invention were evaluated against several β-lactam resistant (for example methicillin-resistant, vancomycin resistant, and/or ampicillin-resistant) bacteria strains by determining the minimum inhibitory concentration (MIC, µg/ml) of each compound with respect to each strain. The MIC, the lowest concentration of antibiotic which inhibits growth of the test organism, was determined by the agar dilution method.

To determine the MIC for bacterial isolates, the test compound was incorporated in a series of two-fold dilutions into liquified Mueller-Hinton agar. Upon solidification, a number of different bacterial strains were spot inoculated with a replicating device onto the agar surface. After overnight incubation, the MIC breakpoint was determined as the lowest drug concentration that completely inhibited growth, disregarding a single colony or a faint haze. The procedures used in these stuides have been standardized by the National Committee for Clinical Laboratory Standards (NCCLS), as per the NCCLS publication entitled METHODS FOR DILUTION ANTIMICROBIAL SUSCEPTIBILITY TESTS (1991), which is incorporated herein by reference.

Aliquots of antimicrobial agents were prepared in phosphate buffered saline (PBS) at pH 7.2. Tween 20 or DMSO was used as a solubilizing vehicle as needed. Standard methods of vortexing, sonicating and gentle heat were used to facilitate solubilizing the test agent. Typically, the concentration of the stock solution was 10× that of the highest drug concentration tested. A 1.28 mg/mL stock solution was used with a subsequent highest working concentration of 128 µg/mL. Serial two-fold dilutions were done through ≦0.25 µg/mL. Each drug level was tested in duplicate. Two-fold drug dilutions were done in sterile 50 mL tubes with a final drug volume of 5 mL. Upon the addition of 45 mL of molten agar, a 10-fold dilution resulted. Two, 25 mL plates were then poured into 15×150 mm square Petri plates with grids and allowed to harden.

A control plate with a reference drug, either cefotaxime, vancomycin or imipenem, was used as the positive growth control. Stock concentrations of reference antibiotics were prepared and frozen at −80° C. Upon preparation, the control plates were sealed and stored in the refrigerator for up to 1 week prior to use; however, imipenem control plates had to be prepared just prior to use. All test plates were used within 24 hours of preparation.

Satisfactory results were obtained where the inoculum contained about $10^4$ colony forming units (cfu) ±0.5 logs. Starting with pure cultures of the test isolates on agar plates, a few isolated colonies were transferred to a tube of nutrient broth and allowed to grow 4–6 hours at 35–36° C. to reach log-phase growth. Dropwise addition of the broth culture to PBS was done to match a 0.5 McFarland turbidity standard equal to $10^8$ cfu/mL. This was further diluted ten-fold in PBS to reach a working inoculum concentration of $10^7$ cfu/mL. When 1 µL of the working inoculum was applied to the agar surface a concentration of about $10^4$ cfu per spot was obtained.

Disposable sterile 1 µL loops were used to inoculate test plates, with each isolate in a designated grid on the agar plate. An alternate method of inoculation involved the use of a replica plater, a device with 48 steel pins allowing the simultaneous inoculation of multiple isolates. After the spots had dried, the plates were incubated at 35–36° C. for 16–20 hours. Endpoints were assessed as the minimum inhibitory concentration (MIC) of antimicrobial agent.

The novel agents of this invention are notable for their enhanced activity against *S. aureus* Col and Enterococci (*E. faecium* and *E. faecalis*). The *S. aureus* Col strain is a high-level PBP2a producer, whereas *S. aureus* Col 8A, its isogenic partner, lacks PBP2a.

Certain compounds show broad activity against both *S. aureus* Col and *S. aureus* Col 8A, as well as Enterococci. The *S. aureus* Col 8A strain was highly responsive to all test agents including the Cefotaxime control. Thus, the compounds of the present invention are effective against PBP2a-producing bacteria. Certain compounds show potent activity against enterococci. Certain other compounds of the present invention, are effective against *E. coli* in addition to Gram-positive organisms.

In Vivo Antibacterial Evaluation

Compounds with superior activity in vitro when compared to reference antibiotics, are further evaluated in a murine model for lethal bacteremic peritonitis.

Groups of 5 female Swiss-Webster mice (Simonsen, Gilroy, Calif.) each are challenged by the intraperitoneal (IP) route with tenfold increments of a bacterial inoculum. This permits calculation of the mean lethal dose ($LD_{50}$) and the $LD_{100}$. For preliminary evaluation of a new antibiotic, mice are challenged IP with an $LD_{100}$ titer of bacteria. In two equal doses administered at the time of bacterial challenge and 2 hours later, groups of 10 mice each are treated subcutaneously with two-fold increments of the test drug and an antibiotic of known efficacy in mice and humans (i.e., positive control). Mice are observed for 72 h. Those alive at 72 h are considered long term survivors. The total drug dose in mg/kg that protects 50% of mice in a group from death is termed the mean protective dose ($PD_{50}$). $PD_{50}$s are similarly determined for several pathogens. The quantitative endpoints for the new drug are then compared with those obtained with reference antibiotics.

Six ten-fold dilutions of inoculum suspended in 0.5 mL of sterilized 7% hog gastric mucin (Sigma) are injected IP in groups of 5 mice each. A control group of 5 mice receive mucin alone. Mice are observed for 72 h. Those alive at 72 h are considered long term survivors. The mean lethal dose ($LD_{50}$) and 100% lethal dose ($LD_{100}$) are determined by the probit test.

For antibiotic efficacy studies, mice are challenged IP with bacterial titers that will afford an $LD_{100}$ for the test strain. In two equal doses administered at the time of bacterial challenge and 2 hours later, groups of 10 mice each are treated by the subcutaneous route (SC) with twofold increments of the test antibiotic; another group is treated similarly with a reference antibiotic of known efficacy in animals and man. Drug doses can range from 0.01 to 512 mg/kg. If the drug is poorly soluble, Tween 20 or propylene glycol will be employed to solubilize the drug. Animals are observed for 72 h. The 50% protective dose ($PD_{50}$) is calculated in mg/kg by the probit method. The $PD_{50}$ is the same as the 50% effective dose ($ED_{50}$) and the 50% curative dose ($CD_{50}$). Samples of blood from the hearts of all animals that die and from half the mice that survive are cultured on brain-heart infusion agar. Animals that received a protective dosage of the test drug will be alive at 72 h, although they may appear moderately ill to very ill during the observation period. Infected, placebo-treated control mice and those receiving non-effective i.e. lower dosages of the test drug will demonstrate a high rate of mortality. Most of these mice will die within 6 to 48 h. Those alive at 72 h will be considered long term survivors.

TABLE 1

Antimicrobial Properties of 7-(Acylamido)-3-(arylthio)cephems

| Organism | Imipenem | 1 | 2 | 3 | 4 | 5 | 6 |
|---|---|---|---|---|---|---|---|
| S. aureus ATCC 29213 | ≦0.25 | 0.13 | <0.06 | 0.5 | 0.25 | 0.13 | 0.25 |
| S. aureus Col8A (Meth$^S$)(lac$^-$) | ≦0.25 | ≦0.06 | ≦0.06 | 0.5 | 0.25 | ≦0.06 | 0.13 |
| S. aureus PC1 (Meth$^S$)(lac$^+$) | ≦0.25 | 1 | 0.5 | 0.5 | 0.25 | 0.25 | 0.5 |
| S. aureus ATCC 13709 (Meth$^S$) | ≦0.25 | — | — | 0.5 | 0.25 | ≦0.06 | ≦0.06 |
| S. aureus Col (Meth$^R$)(lac$^-$) | 32 | 4 | 1 | 8 | 8 | 8 | 2 |
| S. aureus 76 (Meth$^R$)(lac$^+$) | 32 | 8 | 4 | 8 | 8 | 16 | 8 |
| S. aureus ATCC 33593 (Meth$^R$) | 32 | 8 | 4 | 8 | 4 | 16 | 8 |
| S. aureus Spain #356 (Meth$^R$) | 323 | 8 | 4 | 8 | 8 | 16 | 8 |
| S. haemolyticus 05 (Meth$^R$) | 64 | 16 | 4 | 8 | 8 | 16 | 16 |
| E. faecalis ATCC 29212 | ≦0.25 | 1 | 0.5 | 0.5 | 0.5 | 2 | 0.5 |
| E. faecium ATCC 35667 | 4 | 2 | 1 | 2 | 2 | 4 | 2 |
| E. faecium VanA (Van$^R$) | 4 | 8 | 4 | 8 | 4 | 32 | 8 |
| E. faecalis VanB (Van$^R$) | 0.5 | 4 | 0.5 | 1 | 4 | 4 | 8 |
| E. faecium A491 (Amp$^R$) | >128 | >32 | >32 | >32 | >32 | >32 | >32 |
| E. coli ATCC 25992 | ≦0.25 | >32 | 16 | 2 | 4 | >32 | >32 |
| P. aeruginosa ATCC 27853 | 1 | >32 | >32 | >32 | >32 | >32 | >32 |

| Organism | Imipenem | 7 | 8 | 9 | 10 | 11 | 12 |
|---|---|---|---|---|---|---|---|
| S. aureus ATCC 29213 | ≦0.25 | 0.5 | 1 | 0.25 | 0.5 | 0.5 | 0.5 |
| S. aureus Col8A (Meth$^S$)(lac$^-$) | ≦0.25 | 0.5 | 1 | 0.13 | 0.5 | 1 | 0.5 |
| S. aureus PC1 (Meth$^S$)(lac$^+$) | ≦0.25 | 2 | 1 | 1 | 0.5 | 1 | 0.5 |
| S. aureus ATCC 13709 (Meth$^S$) | ≦0.25 | 0.5 | 1 | ≦0.06 | 0.5 | 0.5 | 0.25 |
| S. aureus Col (Meth$^R$)(lac$^-$) | 32 | 8 | 2 | 1 | 2 | 4 | 2 |
| S. aureus 76 (Meth$^R$)(lac$^+$) | 32 | 8 | 4 | 4 | 2 | 8 | 2 |
| S. aureus ATCC 33593 (Meth$^R$) | 32 | 8 | 4 | 4 | 2 | 4 | 2 |
| S. aureus Spain #356 (Meth$^R$) | 32 | 8 | 4 | 4 | 2 | 8 | 2 |
| S. haemolyticus 05 (Meth$^R$) | 64 | 32 | 4 | 16 | 4 | 4 | 2 |
| E. faecalis ATCC 29212 | ≦0.25 | 1 | 0.5 | 1 | 0.5 | 0.25 | 0.25 |
| E. faecium ATCC 35667 | 4 | 4 | 2 | 1 | 2 | 2 | 1 |
| E. faecium VanA (Van$^R$) | 4 | 16 | 8 | 4 | 4 | 4 | 4 |
| E. faecalis VanB (Van$^R$) | 0.5 | 2 | 0.5 | 2 | 1 | 0.5 | 0.5 |
| E. faecium A491 (Amp$^R$) | >128 | >32 | 32 | >32 | >32 | >32 | >32 |
| E. coli ATCC 25992 | ≦0.25 | 4 | 2 | >32 | 4 | 8 | 8 |
| P. aeruginosa ATCC 27853 | 1 | >32 | >32 | >32 | >32 | >32 | >32 |

| Organism | Imipenem | 13 | 14 | 15 | 16 | 17 | 18 |
|---|---|---|---|---|---|---|---|
| S. aureus ATCC 29213 | ≦0.25 | 2 | 0.5 | 1 | 0.25 | 0.25 | 1 |
| S. aureus Col8A (Meth$^S$)(lac$^-$) | ≦0.25 | 2 | 0.5 | 1 | 0.25 | 0.5 | 1 |
| S. aureus PC1 (Meth$^S$)(lac$^+$) | ≦0.25 | 2 | 0.5 | 1 | 0.25 | 0.25 | 1 |
| S. aureus ATCC 13709 (Meth$^S$) | ≦0.25 | 2 | 0.25 | 0.5 | 0.13 | 0.25 | 1 |
| S. aureus Col (Meth$^R$)(lac$^-$) | 32 | 4 | 4 | 4 | 0.5 | 2 | 44 |
| S. aureus 76 (Meth$^R$)(lac$^+$) | 32 | 8 | 4 | 4 | 1 | 4 | 8 |
| S. aureus ATCC 33593 (Meth$^R$) | 32 | 8 | 2 | 4 | 1 | 2 | 4 |
| S. aureus Spain #356 (Meth$^R$) | 32 | 8 | 4 | 4 | 1 | 4 | 8 |
| S. haemolyticus 05 (Meth$^R$) | 64 | 8 | 4 | 8 | 2 | 8 | 8 |
| E. faecalis ATCC 29212 | ≦0.25 | 1 | 0.25 | 2 | ≦0.06 | 0.13 | 0.25 |
| E. faecium ATCC 35667 | 4 | 4 | 1 | 2 | 0.5 | 1 | 2 |
| E. faecium VanA (Van$^R$) | 4 | 8 | 2 | 4 | 0.25 | 0.25 | 2 |
| E. faecalis VanB (Van$^R$) | 0.5 | 2 | 0.25 | 0.5 | 0.13 | 0.5 | 0.5 |
| E. faecium A491 (Amp$^R$) | >128 | >32 | >32 | >32 | 8 | >32 | >32 |
| E. coli ATCC 25992 | ≦0.25 | 8 | 4 | 8 | 8 | 2 | 8 |
| P. aeruginosa ATCC 27853 | 1 | >32 | >32 | >32 | >32 | >32 | >32 |

| Organism | Imipenem | 19 | 20 | 21 | 22 | 23 | 24 |
|---|---|---|---|---|---|---|---|
| S. aureus ATCC 29213 | ≦0.25 | 0.5 | 0.5 | 0.25 | 0.25 | 1 | 1 |
| S. aureus Col8A (Meth$^S$)(lac$^-$) | ≦0.25 | 0.5 | 0.5 | 0.25 | 0.5 | 0.5 | 1 |
| S. aureus PC1 (Meth$^S$)(lac$^+$) | ≦0.25 | 0.5 | 0.5 | 0.5 | 1 | 0.5 | 1 |
| S. aureus ATCC 13709 (Meth$^S$) | ≦0.25 | 0.5 | 0.5 | 1 | 1 | 0.5 | 1 |
| S. aureus Col (Meth$^R$)(lac$^-$) | 32 | 8 | 2 | 1 | 2 | 2 | 8 |
| S. aureus 76 (Meth$^R$)(lac$^+$) | 32 | 8 | 4 | 1 | 2 | 4 | 8 |
| S. aureus ATCC 33593 (Meth$^R$) | 32 | 8 | 2 | 1 | 2 | 4 | 4 |
| S. aureus Spain #356 (Meth$^R$) | 32 | 8 | 4 | 1 | 2 | 4 | 4 |
| S. haemolyticus 05 (Meth$^R$) | 64 | 16 | 4 | 2 | 2 | 4 | 8 |
| E. faecalis ATCC 29212 | ≦0.25 | 1 | 1 | 0.13 | 0.13 | 0.5 | 0.25 |
| E. faecium ATCC 35667 | 4 | 1 | 1 | 0.5 | 1 | 2 | 2 |
| E. faecium VanA (Van$^R$) | 4 | 2 | 2 | 1 | 2 | 4 | 4 |
| E. faecalis VanB (Van$^R$) | 0.5 | 0.5 | 0.5 | 0.13 | 0.5 | 1 | 0.5 |
| E. faecium A491 (Amp$^R$) | >128 | >32 | >32 | 8 | 16 | >32 | >32 |
| E. coli ATCC 25992 | ≦0.25 | 8 | 4 | 32 | 8 | 2 | 8 |
| P. aeruginosa ATCC 27853 | 1 | >32 | >32 | >32 | >32 | >32 | >32 |

TABLE 1-continued

Antimicrobial Properties of 7-(Acylamido)-3-(arylthio)cephems

| Organism | Imipenem | 25 | 26 | 27 | 28 | 29 | 30 |
|---|---|---|---|---|---|---|---|
| S. aureus ATCC 29213 | ≦0.25 | 0.25 | 0.13 | 0.25 | 1 | 0.25 | 0.25 |
| S. aureus Col8A (Meth$^S$)(lac$^-$) | ≦0.25 | 0.25 | 0.13 | ).13 | ).25 | 0.25 | 0.13 |
| S. aureus PC1 (Meth$^S$)(lac$^+$) | ≦0.25 | 0.25 | 0.13 | 0.25 | 0.5 | 0.25 | ≦0.25 |
| S. aureus ATCC 13709 (Meth$^S$) | ≦0.25 | 0.25 | ≦0.06 | 0.13 | 0.13 | 0.13 | ≦0.25 |
| S. aureus Col (Meth$^R$)(lac$^-$) | 32 | 1 | 0.5 | 0.5 | 2 | 1 | 0.5 |
| S. aureus 76 (Meth$^R$)(lac$^+$) | 32 | 2 | 1 | 1 | 2 | 1 | 2 |
| S. aureus ATCC 33593 (Meth$^R$) | 32 | 1 | 1 | 1 | 4 | 2 | 1 |
| S. aureus Spain #356 (Meth$^R$) | 32 | 2 | 1 | 1 | 2 | 2 | 1 |
| S. haemolyticus 05 (Meth$^R$) | 64 | 2 | 2 | 2 | 4 | 2 | 1 |
| E. faecalis ATCC 29212 | ≦0.25 | 0.13 | ≦0.06 | ≦0.06 | 0.13 | ≦0.06 | ≦0.06 |
| E. faecium ATCC 35667 | 4 | 1 | 0.25 | 0.25 | 1 | 0.25 | 0.5 |
| E. faecium VanA (Van$^R$) | 4 | 2 | 0.5 | 0.5 | 4 | 0.5 | 1 |
| E. faecalis VanB (Van$^R$) | 0.5 | 0.13 | 0.13 | ≦0.06 | 0.25 | ≦0.06 | ≦0.06 |
| E. faecium A491 (Amp$^R$) | >128 | 32 | 8 | 4 | 16 | 4 | 8 |
| E. coli ATCC 25992 | ≦0.25 | 4 | >32 | 8 | 2 | 8 | 8 |
| P. aeruginosa ATCC 27853 | 1 | >32 | >32 | 32 | 32 | >32 | >32 |

| Organism | Imipenem | 31 | 32 | 33 | 34 | 35 | 36 |
|---|---|---|---|---|---|---|---|
| S. aureus ATCC 29213 | ≦0.25 | 0.25 | 0.25 | 0.25 | ≦0.06 | 0.25 | 0.5 |
| S. aureus Col8A (Meth$^S$)(lac$^-$) | <0.25 | 0.25 | 0.25 | 0.25 | ≦0.06 | 0.25 | 0.25 |
| S. aureus PC1 (Meth$^S$)(lac$^+$) | ≦0.25 | 0.25 | 0.5 | 0.25 | 0.13 | 0.5 | 0.25 |
| S. aureus ATCC 13709 (Meth$^S$) | ≦0.25 | 0.25 | 0.13 | 0.13 | ≦0.06 | 0.25 | 0.25 |
| S. aureus Col (Meth$^R$)(lac$^-$) | 32 | 2 | 1 | 1 | 1 | 2 | 1 |
| S. aureus 76 (Meth$^R$)(lac$^+$) | 32 | 2 | 2 | 1 | 1 | 2 | 2 |
| S. aureus ATCC 33593 (Meth$^R$) | 32 | 2 | 2 | 2 | 1 | 2 | 1 |
| S. aureus Spain #356 (Meth$^R$) | 32 | 2 | 2 | 1 | 1 | 2 | 1 |
| S. haemolyticus 05 (Meth$^R$) | 64 | 4 | 4 | 2 | 4 | 4 | 2 |
| E. faecalis ATCC 29212 | ≦0.25 | 0.5 | ≦0.06 | 0.13 | ≦0.06 | ≦0.06 | 0.25 |
| E. faecium ATCC 35667 | 4 | 0.5 | 0.5 | 0.5 | 0.25 | 0.25 | 0.5 |
| E. faecium VanA (Van$^R$) | 4 | 1 | 1 | 2 | 0.5 | 0.5 | 1 |
| E. faecalis VanB (Van$^R$) | 0.5 | 0.25 | 0.13 | 0.13 | ≦0.06 | 0.25 | 0.13 |
| E. faecium A491 (Amp$^R$) | >128 | 8 | 8 | 8 | 4 | 4 | 8 |
| E. coli ATCC 25992 | ≦0.25 | 8 | 8 | 1 | 4 | 8 | 16 |
| P. aeruginosa ATCC 27853 | 1 | >32 | >32 | 32 | >32 | >32 | >32 |

| Organism | Imipenem | 37 | 38 | 39 | 40 | 41 | 42 |
|---|---|---|---|---|---|---|---|
| S. aureus ATCC 29213 | ≦0.25 | 0.5 | 0.13 | 0.25 | 0.25 | 0.13 | 0.13 |
| S. aureus Col8A (Meth$^S$)(lac$^-$) | ≦0.25 | ≦0.06 | 0.13 | 0.5 | 0.5 | 0.25 | 0.25 |
| S. aureus PC1 (Meth$^S$)(lac$^+$) | ≦0.25 | 1 | 0.25 | 0.5 | 0.13 | 0.25 | 0.13 |
| S. aureus ATCC 13709 (Meth$^S$) | ≦0.25 | ≦0.06 | 0.13 | 0.25 | 0.25 | 0.13 | 0.13 |
| S. aureus Col (Meth$^R$)(lac$^-$) | 32 | 0.5 | 1 | 2 | 2 | 1 | 0.5 |
| S. aureus 76 (Meth$^R$)(lac$^+$) | 32 | 4 | 1 | 4 | 2 | 1 | 1 |
| S. aureus ATCC 33593 (Meth$^R$) | 32 | 16 | 1 | 4 | 2 | 1 | 1 |
| S. aureus Spain #356 (Meth$^R$) | 32 | 8 | 1 | 4 | 2 | 1 | 1 |
| S. haemolyticus 05 (Meth$^R$) | 64 | 8 | 2 | 8 | 4 | 1 | 2 |
| E. faecalis ATCC 29212 | ≦0.25 | 0.25 | 0.13 | 0.25 | 0.13 | ≦0.06 | ≦0.06 |
| E. faecium ATCC 35667 | 4 | 0.5 | 1 | 1 | 1 | 0.25 | 0.25 |
| E. faecium VanA (Van$^R$) | 4 | 2 | 2 | 2 | 2 | 1 | 0.5 |
| E. faecalis VanB (Van$^R$) | 0.5 | 0.5 | 0.13 | 0.25 | 0.25 | ≦0.06 | ≦0.06 |
| E. faecium A491 (Amp$^R$) | >128 | >32 | >32 | 32 | 16 | 8 | 4 |
| E. coli ATCC 25992 | ≦0.25 | >32 | 2 | 8 | 8 | 4 | 2 |
| P. aeruginosa ATCC 27853 | 1 | >32 | >32 | >32 | >32 | 32 | 32 |

| Organism | Imipenem | 43 | 44 | 45 | 46 | 47 | 48 |
|---|---|---|---|---|---|---|---|
| S. aureus ATCC 29213 | ≦0.25 | 0.5 | 0.5 | 1 | 1 | 1 | 0.5 |
| S. aureus Col8A (Meth$^S$)(lac$^-$) | ≦0.25 | 0.5 | 0.5 | 1 | 0.5 | 0.5 | 0.5 |
| S. aureus PC1 (Meth$^S$)(lac$^+$) | ≦0.25 | 1 | 2 | 2 | 2 | 2 | 0.5 |
| S. aureus ATCC 13709 (Meth$^S$) | ≦0.25 | 0.5 | 2 | 2 | 2 | 2 | 0.25 |
| S. aureus Col (Meth$^R$)(lac$^-$) | 32 | 2 | 4 | 4 | 2 | 2 | 4 |
| S. aureus 76 (Meth$^R$)(lac$^+$) | 32 | 2 | 4 | 4 | 4 | 2 | 8 |
| S. aureus ATCC 33593 (Meth$^R$) | 32 | 2 | 4 | 4 | 2 | 2 | 4 |
| S. aureus Spain #356 (Meth$^R$) | 32 | 2 | 4 | 4 | 4 | 2 | 8 |
| S. haemolyticus 05 (Meth$^R$) | 64 | 4 | 8 | 8 | 8 | 4 | 16 |
| E. faecalis ATCC 29212 | ≦0.25 | 0.13 | 0.13 | 0.13 | 0.13 | 0.13 | 0.25 |
| E. faecium ATCC 35667 | 4 | 1 | 4 | 2 | 2 | 2 | 1 |
| E. faecium VanA (Van$^R$) | 4 | 1 | 2 | 4 | 2 | 2 | 4 |
| E. faecalis VanB (Van$^R$) | 0.5 | 0.25 | — | — | — | — | 0.5 |
| E. faecium A491 (Amp$^R$) | >128 | 8 | 16 | 16 | 16 | 16 | 32 |
| E. coli ATCC 25992 | ≦0.25 | 8 | 8 | 16 | 8 | 8 | 4 |
| P. aeruginosa ATCC 27853 | 1 | >32 | >32 | >32 | >32 | >32 | >32 |

TABLE 1-continued

Antimicrobial Properties of 7-(Acylamido)-3-(arylthio)cephems

| Organism | Imipenem | 49 | 50 | 51 | 52 | 53 | 54 |
|---|---|---|---|---|---|---|---|
| S. aureus ATCC 29213 | ≤0.25 | 0.25 | 0.13 | 0.25 | 0.5 | 0.5 | 0.25 |
| S. aureus Col8A (Meth$^S$)(lac$^-$) | ≤0.25 | 0.5 | 0.25 | 0.5 | 0.25 | 0.5 | 0.25 |
| S. aureus PC1 (Meth$^S$)(lac$^+$) | ≤0.25 | 0.5 | 0.25 | 0.5 | 0.5 | 1 | 0.25 |
| S. aureus ATCC 13709 (Meth$^S$) | ≤0.25 | 0.25 | 0.13 | 0.5 | 0.5 | 0.25 | 0.25 |
| S. aureus Col (Meth$^R$)(lac$^-$) | 32 | 2 | 2 | 2 | 2 | 4 | 2 |
| S. aureus 76 (Meth$^R$)(lac$^+$) | 32 | 2 | 2 | 4 | 2 | 4 | 2 |
| S. aureus ATCC 33593 (Meth$^R$) | 32 | 2 | 2 | 2 | 2 | 2 | 1 |
| S. aureus Spain #356 (Meth$^R$) | 32 | 2 | 2 | 2 | 2 | 4 | 2 |
| S. haemolyticus 05 (Meth$^R$) | 64 | 4 | 4 | 2 | 2 | 4 | 2 |
| E. faecalis ATCC 29212 | ≤0.25 | 0.13 | 0.13 | 0.13 | ≤0.06 | 0.13 | 0.13 |
| E. faecium ATCC 35667 | 4 | 1 | 1 | 0.13 | ≤0.06 | 1 | 0.5 |
| E. faecium VanA (Van$^R$) | 4 | 2 | 2 | 1 | 1 | 2 | 1 |
| E. faecalis VanB (Van$^R$) | 0.5 | 0.13 | 0.5 | 0.25 | 0.13 | 0.25 | 0.25 |
| E. faecium A491 (Amp$^R$) | >128 | 16 | 16 | 8 | 4 | 16 | 8 |
| E. coli ATCC 25992 | ≤0.25 | 8 | 4 | 8 | 2 | 4 | 8 |
| P. aeruginosa ATCC 27853 | 1 | >32 | >32 | >32 | >32 | >32 | >32 |

| Organism | Imipenem | 55 | 56 | 57 | 58 | 59 | 60 |
|---|---|---|---|---|---|---|---|
| S. aureus ATCC 29213 | ≤0.25 | 0.5 | 0.5 | 1 | 0.5 | 0.5 | 0.25 |
| S. aureus Col8A (Meth$^S$)(lac$^-$) | ≤0.25 | 0.5 | 0.5 | 1 | 0.5 | 0.25 | 0.25 |
| S. aureus PC1 (Meth$^S$)(lac$^+$) | ≤0.25 | 1 | 0.5 | 1 | 1 | 0.5 | 0.25 |
| S. aureus ATCC 13709 (Meth$^S$) | ≤0.25 | 0.25 | 0.25 | 0.5 | 0.5 | 0.13 | 0.13 |
| S. aureus Col (Meth$^R$)(lac$^-$) | 32 | 4 | 2 | 4 | 4 | 2 | 2 |
| S. aureus 76 (Meth$^R$)(lac$^+$) | 32 | 4 | 2 | 4 | 4 | 2 | 1 |
| S. aureus ATCC 33593 (Meth$^R$) | 32 | 2 | 2 | 4 | 2 | 2 | 2 |
| S. aureus Spain #356 (Meth$^R$) | 32 | 4 | 2 | 4 | 4 | 4 | 2 |
| S. haemolyticus 05 (Meth$^R$) | 64 | 4 | 4 | 8 | 4 | 4 | 4 |
| E. faecalis ATCC 29212 | <0.25 | 0.25 | 0.13 | 0.13 | 0.5 | 0.5 | 0.5 |
| E. faecium ATCC 35667 | 4 | 0.5 | 1 | 1 | 1 | 1 | 1 |
| E. faecium VanA (Van$^R$) | 4 | 2 | 1 | 2 | 2 | 2 | 2 |
| E. faecalis VanB (Van$^R$) | 0.5 | 0.5 | 0.5 | 4 | 0.5 | 0.5 | 0.25 |
| E. faecium A491 (Amp$^R$) | >128 | 16 | 8 | 16 | 16 | 16 | 16 |
| E. coli ATCC 25992 | ≤0.25 | 8 | 8 | 4 | 8 | 8 | 8 |
| P. aeruginosa ATCC 27853 | 1 | >32 | >32 | >32 | >32 | >32 | >32 |

| Organism | Imipenem | 61 | 62 | 63 | 64 | 65 |
|---|---|---|---|---|---|---|
| S. aureus ATCC 29213 | ≤0.25 | 1 | 0.5 | 0.25 | 0.25 | 0.5 |
| S. aureus Col8A (Meth$^S$)(lac$^-$) | ≤0.25 | 1 | 0.5 | 0.13 | 0.25 | 0.5 |
| S. aureus PC1 (Meth$^S$)(lac$^+$) | ≤0.25 | 1 | 0.5 | 0.25 | 0.5 | 1 |
| S. aureus ATCC 13709 (Meth$^S$) | ≤0.25 | 1 | 0.5 | 0.25 | 0.25 | 0.5 |
| S. aureus Col (Meth$^R$)(lac$^-$) | 32 | 4 | 4 | 2 | 2 | 2 |
| S. aureus 76 (Meth$^R$)(lac$^+$) | 32 | 4 | 4 | 2 | 4 | 4 |
| S. aureus ATCC 33593 (Meth$^R$) | 32 | 4 | 4 | 2 | 4 | 4 |
| S. aureus Spain #356 (Meth$^R$) | 32 | 4 | 4 | 4 | 4 | 4 |
| S. haemolyticus 05 (Meth$^R$) | 64 | 8 | 4 | 2 | 4 | 4 |
| E. faecalis ATCC 29212 | ≤0.25 | 0.25 | 0.13 | 0.13 | 0.25 | 0.25 |
| E. faecium ATCC 35667 | 4 | 1 | 1 | 0.5 | 1 | — |
| E. faecium VanA (Van$^R$) | 4 | 2 | 2 | 1 | 2 | 2 |
| E. faecalis VanB (Van$^R$) | 0.5 | 0.25 | 0.25 | 0.25 | 0.5 | 0.5 |
| E. faecium A491 (Amp$^R$) | >128 | 16 | 16 | 16 | 16 | 16 |
| E. coli ATCC 25992 | ≤0.25 | 16 | 8 | 16 | 8 | 16 |
| P. aeruginosa ATCC 27853 | 1 | >32 | >32 | >32 | >32 | >32 |

Cmpd 1 (7R)-7-[(phenylacetyl)amino]-3-(3-isothioureidomethylpyrid-4-ylthio)-3-cephem-4-carboxylate, trifluoroacetic acid salt Cmpd 2 (7R)-7-[(phenylacetyl)amino]-3-(4-isothioureidomethyl-1,2,3-thiadiazol-5-ylthio)-3-cephem-4-carboxylate, trifluoroacetic acid salt Cmpd 3 (7R)-7-[(Z)-2-(aminothiazol-4-yl)-2-(hydroxyimino)acetamido]-3-(3-isothioureidomethylpyrid-4-ylthio)-3-cephem-4-carboxylate, trifluoroacetic acid salt Cmpd 4 (7R)-7-[(Z)-2-(aminothiazol-4-yl)-2-(hydroxyimino)acetamido]-3-(4-isothioureidomethyl-1,2,3-thiadiazol-5-ylthio)-3-cephem-4-carboxylate, trifluoroacetic acid salt Cmpd 5 (7R)-7-[(phenylacetyl)amino]-3-(4-isothioureidomethylthiazol-5-ylthio)-3-cephem-4-carboxylate, trifluoroacetic acid salt Cmpd 6 (7R)-7-[(phenylacetyl)amino]-3-[4-(3-pyrrolidinothiomethyl)-1,2,3-thiadiazol-5-ylthio]-3-cephem-4-carboxylate, trifluoroacetic acid salt Cmpd 7 (7R)-7-[(Z)-2-(aminothiazol-4-yl)-2-(hydroxyimino)acetamido]-3-(4-isothioureidomethylthiazol-5-ylthio)-3-cephem-4-carboxylate, trifluoroacetic acid salt Cmpd 8 (7R)-7-[(Z)-2-(aminothiazol-4-yl)-2-(cyclopentyloxyimino)acetamido]-3-(3-isothioureidomethylpyrid-4-ylthio)-3-cephem-4-carboxylate, trifluoroacetic acid salt Cmpd 9 (7R)-7-[(phenylacetyl)amino]-3-(3-aminoethylthiomethylpyrid-4-ylthio)-3-cephem-4-carboxylate, trifluoroacetic acid salt Cmpd 10 (7R)-7-[(Z)-2-(aminothiazol-4-yl)-2-(hydroxyimino)acetamido]-3-(3- aminoethylthiomethylpyrid-4-ylthio)-3-cephem-4-carboxylate, trifluoroacetic acid salt Cmpd 11 (7R)-7-[(Z)-2-(aminothiazol-4-yl)-2-(hydroxyimino)acetamido]-3-[(methylaminoethylaminoethylthiomethyl)-1,2,3-thiadiazol-5-ylthio]-3-cephem-4-carboxylate, trifluoroacetic acid salt Cmpd 12 (7R)-7-[(Z)-2-(aminothiazol-4-yl)-2-(hydroxyimino)acetamido]-3-[(guanidinoethylaminoethylthiomethyl)-1,2,3-thiadiazol-5-ylthio]-3-cephem-4-carboxylate, trifluoroacetic acid salt Cmpd 13 (7R)-7-[(Z)-2-(aminothiazol-4-yl)-2-(cyclopentyloxyimino)acetamido]-3-(3-aminoethylthiomethylpyrid-4-ylthio)-3-cephem-4-carboxylate, trifluoroacetic acid salt Cmpd 14 (7R)-7-[(Z)-2-(aminothiazol-4-yl)-2-(hydroxyimino)acetamido]-3-(3-guanidinoethylthiomethylpyrid-4-ylthio)-3-cephem-4-carboxylate, trifluoroacetic acid salt Cmpd 15 (7R)-7-[(Z)-2-(aminothiazol-4-yl)-2-(hydroxyimino)acetamido]-3-(3-methylaminoethylthiomethylpyrid-4-ylthio)-3-cephem-4-carboxylate, trifluoroacetic acid salt Cmpd 16 (7R)-7-[(Z)-2-(2-amino-5-chlorothiazol-4-yl)-2-(hydroxyimino)acetamido]-3-(3-aminoethylthiomethylpyrid-4-ylthio)-3-cephem-4-carboxylate, trifluoroacetic acid salt Cmpd 17 (7R)-7-[(Z)-2-(aminothiazol-4-yl)-2-(hydroxyimino)acetamido]-3-[3-(3-pyrrolidinothiomethyl)pyrid-4-ylthio]-3-cephem-4-carboxylate, trifluoroacetic acid salt Cmpd 18 (7R)-7-[(Z)-2-(aminothiazol-4-yl)-2-(hydroxyimino)acetamido]-3-[3-(N-methylglycyl)aminoethylthiomethylpyrid-4-ylthio]-3-cephem-4-carboxylate, trifluoroacetic acid salt Cmpd 19 (7R)-7-[(Z)-2-(aminothiazol-4-yl)-2-(hydroxyimino)acetamido]-3-[3-(2-amino-1,1-dimethylethylthiomethyl)pyrid-4-ylthio]-3-cephem-4-carboxylate, trifluoroacetic acid salt Cmpd 20 (7R)-7-[(Z)-2-(aminothiazol-4-yl)-2-(hydroxyimino)acetamido]-3-(3-aminoethylthiopyrid-4-ylthio)-3-cephem-4-carboxylate, trifluoroacetic acid salt Cmpd 21 (7R)-7-[(Z)-2-(2-amino-5-bromothiazol-4-yl)-2-(hydroxyimino)acetamido]-3-(3-aminoethylthiomethylpyrid-4-ylthio)-3-cephem-4-carboxylate, trifluoroacetic acid salt Cmpd 22 (7R)-7-[(Z)-2-(2-amino-5-chlorothiazol-4-yl)-2-(hydroxyimino)acetamido]-3-[(methylaminoethylaminoethylthiomethyl)-1,2,3-thiadiazol-5-ylthio]-3-cephem-4-carboxylate, trifluoroacetic acid salt Cmpd 23 (7R)-7-[(Z)-2-(aminothiazol-4-yl)-2-(2-fluoroethoxyimino)acetamido]-3-(3-aminoethylthiomethylpyrid-4-ylthio)-3-cephem-4-carboxylate, trifluoroacetic acid salt Cmpd 24 (7R)-7-[(Z)-2-(aminothiazol-4-yl)-2-(hydroxyimino)acetamido]-3-[3-(glycyl)aminoethylthiomethylpyrid-4-ylthio]-3-cephem-4-carboxylate, trifluoroacetic acid salt Cmpd 25 (7R)-7-[(Z)-2-(aminothiazol-4-yl)-2-(hydroxyimino)acetamido]-3-(3-(N-formamidoyl)aminoethylthiomethylpyrid-4-ylthio)-3-cephem-4-carboxylate, trifluoroacetic acid salt Cmpd 26 (7R)-7-[(Z)-2-phenyl-2-(hydroxyimino)acetamido]-3-(3-aminoethylthiomethylpyrid-4-ylthio)-3-cephem-4-carboxylate, trifluoroacetic acid salt Cmpd 27 (7R)-7-[(Z)-2-(2-amino-5-chlorothiazol-4-yl)-2-(hydroxyimino)acetamido]-3-[3-(3-aminopropyl)thiomethylpyrid-4-ylthio]-3-cephem-4-carboxylate, trifluoroacetic acid salt Cmpd 28 (7R)-7-[(Z)-2-(2-amino-5-chlorothiazol-4-yl)-2-(2-fluoroethoxyimino)acetamido]-3-[(methylaminoethylaminoethylthiomethyl)-1,2,3-thiadiazol-5-ylthio]-3-cephem-4-carboxylate, trifluoroacetic acid salt Cmpd 29 (7R)-7-[(Z)-2-(2-amino-5-chlorothiazol-4-yl)-2-(hydroxyimino)acetamido]-3-[3-(glycyl)aminoethylthiomethylpyrid-4-ylthio]-3-cephem-4-carboxylate, trifluoroacetic acid salt Cmpd 30 (7R)-7-[(Z)-2-(2-amino-5-chlorothiazol-4-yl)-2-(hydroxyimino)acetamido]-3-(3-aminoethylthiopyrid-4-ylthio)-3-cephem-4-carboxylate, trifluoroacetic acid salt Cmpd 31 (7R)-7-[(Z)-2-(2-amino-5-chlorothiazol-4-yl)-2-(hydroxyimino)acetamido]-3-(3-(N-formamidinoyl)aminoethylthiomethylpyrid-4-ylthio)-3-cephem-4-carboxylate, trifluoroacetic acid salt Cmpd 32 (7R)-7-[(Z)-2-(2-amino-5-chlorothiazol-4-yl)-2-(hydroxyimino)acetamido]-3-[3-(3-amino-2-hydroxyprop-1-ylthiomethyl)pyrid-4-ylthio]-3-cephem-4-carboxylate, trifluoroacetic acid salt Cmpd 33 (7R)-7-[(Z)-2-(2-amino-5-chlorothiazol-4-yl)-2-(2-fluoroethoxyimino)acetamido]-3-(3-aminoethylthiomethylpyrid-4-ylthio)-3-cephem-4-carboxylate, trifluoroacetic acid salt Cmpd 34 (7R)-7-[(Z)-2-(2-amino-5-chlorothiazol-4-yl)-2-(hydroxyimino)acetamido]-3-(3-(3-N-formamidoylaminopropylthiomethyl)pyrid-4-ylthio)-3-cephem-4-carboxylate, trifluoroacetic acid salt Cmpd 35 (7R)-7-[(Z)-2-(2-amino-5-chlorothiazol-4-yl)-2-(hydroxyimino)acetamido]-3-[3-(glycyl)aminopropylthiomethylpyrid-4-ylthio]-3-cephem-4-carboxylate, trifluoroacetic acid salt Cmpd 36 (7R)-7-[(Z)-2-(2-amino-5-chlorothiazol-4-yl)-2-(hydroxyimino)acetamido]-3-(3-(2-aminoprop-1-ylthiomethyl)pyrid-4-ylthio)-3-cephem-4-carboxylate, trifluoroacetic acid salt Cmpd 37 (7R)-7-[(phenylacetyl)amino]-3-(4-(2-aminoethylthiomethyl)-1,2,3-thiadiazol-5-ylthio)-3-cephem-4-carboxylate, trifluoroacetic acid salt Cmpd 38 (7R)-7-[(Z)-2-(aminothiazol-4-yl)-2-(hydroxyimino)acetamido]-3-(4-(2-aminoethylthiomethyl)-1,2,3-thiadiazol-5-ylthio)-3-cephem-4-carboxylate, trifluoroacetic acid salt Cmpd 39 (7R)-7-[(Z)-2-(2-amino-5-chlorothiazol-4-yl)-2-(hydroxyimino) acetamido]-3-(3-carboxamidomethyl thiomethylpyrid-4-ylthio)-3-cephem-4-carboxylic acid Cmpd 40 (7R)-7-[(Z)-2-(2-amino-5-chlorothiazol-4-yl)-2-(hydroxyimino)acetamido]-3-(3-(2-aminoethoxymethyl)pyrid-4-ylthio)-3-cephem-4-carboxylate, trifluoroacetic acid salt Cmpd 41 (7R)-7-[(Z)-2-(2-amino-5-chlorothiazol-4-yl)-2-(hydroxyimino)acetamido]-3-(3-(2-N-methylaminoethylthiomethyl)pyrid-4-ylthio)-3-cephem-4-carboxylate, trifluoroacetic acid salt Cmpd 42 (7R)-7-[(Z)-2-(2-amino-5-chlorothiazol-4-yl)-2-(hydroxyimino)acetamido]-3-(3-(pyrrolidin-3-ylthiomethyl)pyrid-4-ylthio)-3-cephem-4-carboxylate, trifluoroacetic acid salt Cmpd 43 (7R)-7-[(Z)-2-(2-amino-5-chlorothiazol-4-yl)-2-(hydroxyimino)acetamido]-3-[3-(N-methylglycyl)aminoethylthiomethylpyrid-4-ylthio]-3-cephem-4-carboxylate, trifluoroacetic acid salt Cmpd 44 (7R)-7-[(Z)-2-(2-amino-5-chlorothiazol-4-yl)-2-(hydroxyimino)acetamido]-3-(3-(5- aminopentyloxymethyl)pyrid-4-ylthio)-3-cephem-4-carboxylate, trifluoroacetic acid salt Cmpd 45 (7R)-7-[(Z)-2-(2-amino-5-chlorothiazol-4-yl)-2-(hydroxyimino)acetamido]-3-(3-aminoethylsulfonylmethylpyrid-4-ylthio)-3-cephem-4-carboxylate, trifluoroacetic acid salt Cmpd 46 (7R)-7-[(Z)-2-(2-amino-5-chlorothiazol-4-yl)-2-(hydroxyimino)acetamido]-3-(3-(4-aminobutyloxymethyl)pyrid-4-ylthio)-3-cephem-4-carboxylate, trifluoroacetic acid salt Cmpd 47 (7R)-7-[(Z)-2-(2-amino-5-chlorothiazol-4-yl)-2-(hydroxyimino)acetamido]-3-(3-(3-aminopropyloxymethyl)pyrid-4-ylthio)-3-cephem-4-carboxylate, trifluoroacetic acid salt Cmpd 48 (7R)-7-[(Z)-2-(2-amino-5-chlorothiazol-4-yl)-2-(hydroxyimino)acetamido]-3-(3-(4-amino-2-butyn-1-yl)pyrid-4-ylthio)-3-cephem-4-carboxylate, trifluoroacetic acid salt Cmpd 49 (7R)-7-[(Z)-2-(2-amino-5-chlorothiazol-4-yl)-2-(hydroxyimino)acetamido]-3-(3-(2-aminopropyloxymethyl)pyrid-4-ylthio)-3-cephem-4-carboxylate, trifluoroacetic acid salt Cmpd 50 (7R)-7-[(Z)-2-(2-amino-5-chlorothiazol-4-yl)-2-(hydroxyimino)acetamido]-3-(3-(4-amino-2-Z-buten-1-yl)pyrid-4-ylthio)-3-cephem-4-carboxylate, trifluoroacetic acid salt Cmpd 51 (7R)-7-[(Z)-2-(2-amino-5-chlorothiazol-4-yl)-2-(hydroxyimino)acetamido]-3-(3-(3-aminopropylthio)pyrid-4-ylthio)-3-cephem-4-carboxylate, trifluoroacetic acid salt Cmpd 52 (7R)-7-[(Z)-2-(2-amino-5-chlorothiazol-4-yl)-2-(hydroxyimino)acetamido]-3-(3-(piperidine-4-ylthiomethyl)pyrid-4-ylthio)-3-cephem-4-carboxylate, trifluoroacetic acid salt Cmpd 53 (7R)-7-[(Z)-2-(2-amino-5-chlorothiazol-4-yl)-2-(hydroxyimino)acetamido]-3-(3-aminoethylsulfinylmethylpyrid-4-ylthio)-3-cephem-4-carboxylate, trifluoroacetic acid salt Cmpd 54 (7R)-7-[(Z)-2-(2-amino-5-chlorothiazol-4-yl)-2-(hydroxyimino)acetamido]-3-(3-(N-acetamidinoyl)aminoethylthiomethylpyrid-4-ylthio)-3-cephem-4-carboxylate, trifluoroacetic acid salt Cmpd 55 (7R)-7-[(Z)-2-(2-amino-5-chlorothiazol-4-yl)-2-(hydroxyimino)acetamido]-3-(3-(5S-5-N,N-dimethylcarboxamidopyrrolidin-3-ylthiomethyl)pyrid-4-ylthio)-3-cephem-4-carboxylate, trifluoroacetic acid salt Cmpd 56 (7R)-7-[(Z)-2-(2-amino-5-chlorothiazol-4-yl)-2-(hydroxyimino)acetamido]-3-[3-(2RS-2-amino-3-hydroxyprop-1-ylthiomethyl)pyrid-4-ylthio]-3-cephem-4-carboxylate, trifluoroacetic acid salt Cmpd 57 (7R)-7-[(Z)-2-(2-amino-5-chlorothiazol-4-yl)-2-(hydroxyimino)acetamido]-3-(3-(N-methylaminoethylaminoethylthiomethyl)pyrid-4-ylthio)-3-cephem-4-carboxylate, trifluoroacetic acid salt Cmpd 58 (7R)-7-[(Z)-2-(2-amino-5-chlorothiazol-4-yl)-2-(hydroxyimino)acetamido]-3-(3-(2R-2-N,N-dimethylcarboxamido-2-aminoethylthiomethyl)pyrid-4-ylthio)-3-cephem-4-carboxylate, trifluoroacetic acid salt Cmpd 59 (7R)-7-[(Z)-2-(2-amino-5-chlorothiazol-4-yl)-2-(hydroxyimino)acetamido]-3-(3-(2R-2-carboxamido-2-aminoethylthiomethyl)pyrid-4-ylthio)-3-cephem-4-carboxylate, trifluoroacetic acid salt Cmpd 60 (7R)-7-[(Z)-2-(2-amino-5-chlorothiazol-4-yl)-2-(hydroxyimino)acetamido]-3-(3-isothioureidomethylpyrid-4-ylthio)-3-cephem-4-carboxylate, trifluoroacetic acid salt Cmpd 61 (7R)-7-[(Z)-2-(2-amino-5-chlorothiazol-4-yl)-2-(hydroxyimino)acetamido]-3-(3-(N,N-dimethylcarboxamidomethylaminoethylthiomethyl)pyrid-4-ylthio)-3-cephem-4-carboxylate, trifluoroacetic acid salt Cmpd 62 (7R)-7-[(Z)-2-(2-amino-5-chlorothiazol-4-yl)-2-(hydroxyimino)acetamido]-3-(3-(2-amino-2-methylpropylthiomethyl)pyrid-4-ylthio)-3-cephem-4-carboxylate, trifluoroacetic acid salt Cmpd 63 (7R)-7-[(Z)-2-(2-amino-5-chlorothiazol-4-yl)-2-(hydroxyimino)acetamido]-3-(3-(N-formylaminoethylthiomethyl)pyrid-4-ylthio)-3-cephem-4-carboxylate, trifluoroacetic acid salt Cmpd 64 (7R)-7-[(Z)-2-(2-amino-5-chlorothiazol-4-yl)-2-(hydroxyimino)acetamido]-3-(3-(N-formylaminoethylthio)pyrid-4-ylthio)-3-cephem-4-carboxylate, trifluoroacetic acid salt Cmpd 65 (7R)-7-[(Z)-2-(2-amino-5-chlorothiazol-4-yl)-2-(hydroxyimino)acetamido]-3-[3-(2R-2-amino-3-hydroxyprop-1-ylthiomethyl)pyrid-4-ylthio]-3-cephem-4-carboxylate, trifluoroacetic acid salt (Compound numbers correspond to those in MIC tables; data reported for challenge with methicillin-susceptible *S. aureus* strain ATCC 13709.)

| Compound: | Vancomycin | Imipenem | Survivors 1 | 3 | 10 |
|---|---|---|---|---|---|
| Dose | | | | | |
| 10 mg/kg | 10/10 | | | | |
| 5 mg/kg | 10/0 | | | | |
| 2.5 mg/kg | 4/10 | | 10/10 | 9/10 | |
| 1.25 mg/kg | 2/10 | | '8/10 | 7/10 | 10/10 |
| 0.625 mg/kg | 2/10 | 10/10 | 6/10 | 8/10 | 8/10 |
| 0.3125 mg/kg | | 10/10 | 5/10 | 5/10 | 2/10 |
| 0.156 mg/kg | | 10/10 | 2/10 | 0/10 | 2/10 |
| 0.078 mg/kg | | 6/10 | | | 2/10 |
| 0.039 mg/kg | | 3/10 | | | 1.29 |
| ED$_{50}$ (mg/kg) | 1.94 | 0.06 | 0.39 | 0.42 | |

| Compound: | 11 | Survivors 14 | 15 | 16 | 17 |
|---|---|---|---|---|---|
| Dose | | | | | |
| 40 mg/kg | | | | | |
| 20 mg/kg | | | | | |
| 10 mg/kg | | | | | |
| 5 mg/kg | | 10/10 | 5/10 | | 6/10 |
| 2.5 mg/kg | 6/10 | 9/10 | 5/10 | 8/10 | 3/10 |
| 1.25 mg/kg | 5/10 | 3/10 | 2/10 | 5/9 | 5/10 |
| 0.625 mg/kg | 3/10 | 3/10 | 0/10 | 3/10 | 2/10 |
| 0.3125 mg/kg | 1/10 | 1/10 | 2/10 | 1/10 | 2/10 |
| 0.156 mg/kg | 1/10 | | | 2/10 | |
| ED$_{50}$ (mg/kg) | 0.96 | 1.13 | 4.63 | 1.00 | 3.59 |

| Compound: | 18 | Survivors 26 | 27 | 28 | 29 |
|---|---|---|---|---|---|
| Dose | | | | | |
| 5 mg/kg | 6/10 | 9/10 | 7/10 | 7/10 | 7/10 |
| 2.5 mg/kg | 2/10 | 7/10 | 6/10 | 3/10 | 9/10 |
| 1.25 mg/kg | 2/10 | 5/10 | 2/10 | 4/10 | 9/10 |
| 0.625 mg/kg | 2/10 | 5/10 | 0/10 | 1/10 | 5/10 |
| 0.3125 mg/kg | 3/10 | 1/10 | 0/10 | 1/10 | 2/10 |
| ED$_{50}$ (mg/kg) | 4.44 | 1.06 | 2.64 | 3.01 | 1.26 |

-continued

| | Survivors | | | | |
|---|---|---|---|---|---|
| Compound: | 30 | 32 | 33 | 39 | 56 |
| Dose | | | | | |
| 5 mg/kg | 10/10 | 8/10 | 8/10 | 10/10 | 8/10 |
| 2.5 mg/kg | 10/10 | 5/10 | 9/10 | 6/10 | 8/10 |
| 1.25 mg/kg | 4/10 | 5/10 | 5/10 | 6/10 | 3/10 |
| 0.625 mg/kg | 2/10 | 1/10 | 4/10 | 3/10 | 3/10 |
| 0.3125 mg/kg | 0/10 | 0/10 | 0/10 | 1/10 | 2/10 |
| $ED_{50}$ (mg/kg) | 1.14 | 2.00 | 1.19 | 1.15 | 1.23 |

| | Survivors | | | | |
|---|---|---|---|---|---|
| Compound: | 57 | 58 | 59 | 64 | 65 |
| Dose | | | | | |
| 5 mg/kg | 9/10 | 5/10 | 10/10 | 8/10 | 8/10 |
| 2.5 mg/kg | 5/10 | 5/10 | 4/10 | 4/10 | 3/10 |
| 1.25 mg/kg | 4/10 | 2/10 | 4/10 | 4/10 | 1/10 |
| 0.625 mg/kg | 4/10 | 1/10 | 6/10 | 1/10 | 2/10 |
| 0.3125 mg/kg | 4/10 | 1/10 | 4/10 | 1/10 | 1/10 |
| $ED_{50}$ (mg/kg) | 1.08 | 4.10 | 0.81 | 2.27 | 3.10 |

EXAMPLES

The present invention will be more fully described in conjunction with the following specific examples which are not to be construed in any way as limiting the scope of the invention.

Example 1
(7R)-7-[(phenylacetyl)amino]-3-(4-hydroxymethyl-1,2,3-thiadiazol-5-ylthio)-3-cephem-4-carboxylate, 4-methoxybenzyl ester To a stirred solution of 1,3-dichloroacetone (6.85 g, 54 mmol) and ethyl 3-mercaptopropionate (13.9 mL, 108 mmol) in anhydrous tetrahydrofuran (150 mL) was dropwise added triethylamine (15.0 mL, 108 mmol) at 0° C. and stirred at room temperature for 24 h. The solvent was evaporated and the residue was partitioned between water and ethyl acetate. The ethyl acetate phase was washed with 5% hydrochloric acid and then brine, dried over sodium sulfate, and concentrated to dryness, affording 17.4 g of the crude 1,3-bis(2-ethoxycarbonylethylthio)acetone.

A solution of 1,3-bis[(2-ethoxycarbonylethyl)thio]acetone (6.22 g, 19.3 mmol), ethyl carbazate (2.40 g, 23.1 mmol) and a catalytic amount of p-toluenesulfonic acid in anhydrous acetonitrile (50 mL) containing molecular sieve was stirred for 2 days at room temperature. The reaction was quenched with water/ethyl acetate and filtered. The filtrate was extracted with ethyl acetate. The organic extract was washed with aqueous sodium bicarbonate, dried over sodium sulfate, and concentrated. The residue was triturated with hexane, affording 7.2 g of 1,3-bis[(2-ethoxycarbonylethyl)thio]acetone ethoxycarbonylhydrazone. 1H NMR (CDCl$_3$) δ 2.2–2.4 (m, 9), 2.6–2.8 (m, 8H), 3.42 (s, 2H), 3.54 (s, 2H), 4.1–4.3 (m, 6H), 8.82 (br s, 1H).

To a solution of the hydrazone (7.2 g, 17.6 mmol) in 1,2-dichloroethane (20 mL) was added thionyl chloride (3.9 mL, 53 mmol) at 0° C. and stirred overnight at room temperature. The mixture was concentrated to a volume of 10 mL, diluted with dichloromethane, washed with aqueous sodium bicarbonate, dried over sodium sulfate, and then concentrated to dryness, affording 6.47 g of 5-[(2-ethoxycarbonylethyl)thio]-4-[(2-ethoxycarbonylethyl)thiomethyl]-1,2,3-thiadiazole. 1H NMR (CDCl$_3$) δ 1.2–1.3 (m, 6H), 2.60 (t, 2H, J=7), 2.68 (t, 2H, J=7), 2.77 (t, 2H, J=7), 3.24 (t, 2H, J=7), 4.07 (s, 2H), 4.1–4.2 (m, 4H).

To a solution of 5-[(2-ethoxycarbonylethyl)thio]-4-[(2-ethoxycarbonylethyl)thiomethyl]-1,2,3-thiadiazole (1.0 g, 3.0 mmol) in dichloromethane (40 mL) was added m-chloroperoxybenzoic acid in several portions at 0° C. until the starting material was disappeared. The mixture was then sequentially washed with saturated aqueous sodium thiosulfate, cold aqueous 1% sodium hydroxide and brine, and was concentrated to dryness. The oxidized product was treated with trifluoroacetic anhydride (2 mL) for 30 min at room temperature. After removal of trifluoroacetic anhydride under the reduced pressure, the mixture was stirred in ethyl acetate/1% sodium hydroxide (30 ml/30 mL) for 30 min. The ethyl acetate layer was concentrated to a volume of 5 mL and methanol (10 mL) was added. Excess sodium borohydride (200 mg) was added in portions at 0° C. while stirring. After 30 min, the reaction was quenched with diluted hydrochloric acid. The mixture was extracted with ethyl acetate and concentrated. The residue was purified by silica gel chromatography (1% methanol/dichloromethane) to provide 225 mg of 5-[(2-ethoxycarbonylethyl)thio]-4-hydroxymethyl-1,2,3-thiadiazole. 1H NMR (CDCl$_3$) δ 1.27 (t, 3H, J=8), 2.71 (t, 2H, J=7), 3.27 (t, 2H, J=7), 4.16 (q, 2H, J=8), 5.03 (s, 2H).

To a solution of 5-[(2-ethoxycarbonylethyl)thio]-4-hydroxymethyl-1,2,3-thiadiazole (225 mg, 0.91 mmol) in anhydrous ethanol (20 mL) was added 0.5M sodium methoxide in methanol (1.6 mL). After 10 min, the mixture was concentrated, and was triturated with dichloromethane to obtain the sodium thiolate. A solution of the sodium thiolate and (7R)-7-[(phenylacetyl)amino]-3-trifluoromethanesulfonyloxy-3-cephem-4-carboxylate, 4-methoxybenzyl ester (500 mg, 0.85 mmol) in tetrahydrofuran (10 mL) was stirred at 0° C. for 30 min, and water (50 ml) was added. The reaction mixture was extracted with ethyl acetate and concentrated. The residue was purified by silica gel chromatography (2% methanol/dichloromethane), affording 407 mg of the title compound. 1H NMR (CDCl$_3$) δ 3.22 (d, 1H, J=18), 3.46 (d, 1H, J=18), 3.61 (d, 1H, J=16), 3.67 (d, 1H, J=16), 3.81 (s, 3H), 4.95 (d, 1H, J=5), 5.02 (s, 2H), 5.23 (d, 1H, J=12), 5.28 (d, 1H, J=12), 5.83 (dd, 1H, J=5, 8), 6.14 (d, 1H, J=8), 6.86 (d, 2H, J=9), 7.2–7.4 (m, 7H).

Example 2
(7R)-7-[(phenylacetyl)amino]-3-(4-chloromethyl-1,2,3-thiadiazol-5-ylthio)-3-cephem-4-carboxylate, 4-methoxybenzyl ester To DMF (5 mL) was added thionyl chloride (85 mL, 1.71 mmol) and stirred for 30 min at room temperature. A solution of (7R)-7-[(phenylacetyl)amino]-3-(4-hydroxymethyl-1,2,3-thiadiazol-5-ylthio)-3-cephem-4-carboxylate, 4-methoxybenzyl ester (400 mg, 0.684 mmol) in DMF (1 mL) was added and stirred for an additional 30 min. The reaction was quenched with water, and the mixture was extracted with ethyl acetate. The organic extract was washed with water and concentrated. The residue was purified by silica gel chromatography (0.5% methanol/dichloromethane), affording 322 mg of the title compound. 1H NMR (CDCl$_3$) δ 3.20 (d, 1H, J=18), 3.47 (d, 1H, J=18), 3.60 (d, 1H, J=16), 3.66 (d, 1H, J=16), 3.79 (s, 3H), 4.95 (m, 3H), 5.22 (d, 1H, J=12), 5.25 (d, 1H, J=12), 5.85 (dd, 1H, J=5, 8), 6.53 (d, 1H, J=8), 6.84 (d, 2H, J=9), 7.2–7.4 (m, 7H).

Example 3
(7R)-7-[(phenylacetyl)amino]-3-(4-isothioureidomethyl-1,2,3-thiadiazol-5-ylthio)-3-cephem-4-carboxylate, trifluoroacetic acid salt A solution of (7R)-7-[(phenylacetyl)amino]-3-(4-chloromethyl-1,2,3-thiadiazol-5-ylthio)-3-cephem-4-carboxylate, 4-methoxybenzyl ester (70 mg, 0.12 mmol), thiourea (7.6 mg, 0.1 mmol) and sodium iodide (15 mg, 0.1 mmol) in dry acetonitrile (3 mL) was stirred at room temperature overnight. The mixture was concentrated and triturated with dichloromethane to remove the unreacted starting material. The residue was redissolved in acetone (2 mL) and filtered. The filtrate was concentrated to dryness, affording 60 mg of (7R)-7-[(phenylacetyl)amino]-3-(4-isothioureidomethyl-1,2,3-thiadiazol-5-ylthio)-3-cephem-4-carboxylate, 4-methoxybenzyl ester, iodide salt as a yellowish solid. 1H NMR (acetone-$d_6$) δ 3.56 (d, 1H, J=18), 3.66 (d, 1H, J=16), 3.72 (d, 1H, J=16), 3.80 (s, 3H), 3.86 (d, 1H, J=18), 5.06 (d, 1H, J=15), 5.10 (d, 1H, J=15), 5.28 (m, 3H), 5.88 (dd, 1H, J=5, 8), 6.91 (d, 2H, J=9), 7.2–7.4 (m, 7), 8.32 (d, 1H, J=8).

A mixture of (7R)-7-[(phenylacetyl)amino]-3-(4-isothioureidomethyl-1,2,3-thiadiazol-5-ylthio)-3-cephem-4-carboxylate, 4-methoxybenzyl ester, iodide salt (60 mg), anisole (0.1 mL) and trifluoroacetic acid (1 mL) was stirred at 0° C. for 30 min, and then concentrated to dryness. The residue was sequentially triturated with dichloromethane (40 mL) and water (0.5 mL) to afford 38 mg of the title compound. 1H NMR (DMSO-$d_6$) δ 3.41 (d, 1H, J=18), 3.48 (d, 1H, J=14), 3.55 (d, 1H, J=14), 3.69 (d, 1H, J=18), 4.86 (d, 1H, J=15), 4.94 (d, 1H, J=15), 5.14 (d, 1H, J=5), 5.72 (dd, 1H, J=5, 8), 7.1–7.3 (m, 7H), 9.18 (d, 1H, J=8)

Example 4
(7R)-7-amino-3-(4-chloromethyl-1,2,3-thiadiazol-5-ylthio)-3-cephem-4-carboxylate, 4-methoxybenzyl ester To a solution of (7R)-7-[(phenylacetyl)amino1-3-(4-chloromethyl-1,2,3-thiadiazol-5-ylthio)-3-cephem-4-carboxylate, 4-methoxybenzyl ester (604 mg, 1.68 mmol) and pyridine (0.271 mL, 3.36 mmol) in dichloromethane (20 mL) was dropwise added a solution of phosphorous pentachloride (208 mg, 2.68 mmol) in dichloromethane (10.7 mL) and stirred at −10° C. for 2 h. After cooling to −40° C., isobutanol (1.55 mL) was added, and the resulting mixture was stirred at −10° C. for 4 h. The reaction was quenched with water, and the mixture was extracted with dichloromethane. The organic extract was washed with saturated aqueous sodium bicarbonate and concentrated. The residue was purified by silica gel chromatography (10% methanol/dichloromethane), affording 599 mg of the title compound. 1H NMR (CD$_3$OD) d 3.45 (d, 1H, J=18), 3.65 (d, 1H, J=18), 3.76 (s, 3H), 4.75 (1H, overlapped with water), 4.98 (s, 2H), 5.05 (d, 1H, J=5), 5.23 (s, 2H), 6.82 (d, 2H, J=9), 7.26 (d, 2H, J=9).

Example 5
4-chloro-3-hydroxymethylpyridine

To a solution of 4-chloro-3-pyridyl carboxyaldehyde (140 mg, 1.0 mmol) in THF (1 mL) at 0° C. was added methanol (1 mL) followed by portionwise addition of sodium borohydride (75 mg, 2.0 mmol). After 1 hr, acetic acid (0.15 ml) was added and the reaction mixture was evaporated to dryness with rotary evaporator at room temperature. The solid residue was chromatographed on silica gel column (1% MeOH/dichloromethane) to afford 60 mg (42%) of the title compound. 1H NMR (CDCl$_3$) δ 4.30 (br s, 1H), 4.80 (s, 2H), 7.30 (d, 1H, J=5), 8.34 (d, 1H, J=5), 8.62 (s, 1H).

Example 6
(7R)-7-[(phenylacetyl)amino]-3-(3-hydroxymethylpyrid-4-ylthio)-3-cephem-4-carboxylate, 4-methoxybenzyl ester To a solution of 4-chloro-3-hydroxymethylpyridine (60 mg, 0.42 mmol) in DMF (1 mL) at room temperature under nitrogen was added potassium thioacetate (71 mg, 0.63 mmol). After overnight stirring, the solvent was removed with rotary evaporator. The residue was washed with ethyl ether and taken up in 10% MeOH/dichloromethane. The insoluble material was filtered off and the filtrate was concentrated with rotary evaporator. The residual material was dissolved in MeOH (3 mL) and aqueous sodium hydroxide was added (0.5 mL, 3 M). After an overnight reaction at room temperature the reaction was acidified with 1 M hydrochloric acid, evaporated to dryness with rotary evaporator, and partitioned between saturated sodium bicarbonate solution and ethyl acetate. The organic layer was dried with sodium sulfate and the solvent was removed with rotary evaporator. The residue was dissolved in MeOH and (7R)-7-[(phenylacetyl)amino]-3-trifluoromethanesulfonyloxy-3-cephem-4-carboxylate, 4-methoxybenzyl ester(240 mg, 0.42 mmol) was added followed by addition of dichloromethane. After an overnight reaction at room temperature the reaction was partitioned between 5% sodium bicarbonate solution and ethyl acetate. Purification on silica gel (Chromatotron, 2% MeOH/dichloromethane) afforded the title compound (60 mg, 25%). 1H NMR (CDCl$_3$) δ 3.15 (d, 1H, J=18), 3.55 (d, 1H, J=18), 3.63 (d, 1H, J=18), 3.68 (d, 1H, J=18), 3.78 (s, 3H), 4.61 (d, 1H, J=13), 4.66(d, 1H, J=13), 5.05 (d, 1H, J=5), 5.08 (d, 1H, J=13), 5.25 (d, 1H, J=13), 5.89 (dd, 1H, J=9, 5), 6.76 (d, 2H, J=8), 7.05 (m, 2H), 7.16 (d, 21H, J=8), 7.32 (m, 5H), 8.40 (d, 1H, J=5), 8.48 (s, 1H).

Example 7
(7R)-7-[(phenylacetyl)amino]-3-(3-chloromethylpyrid-4-ylthio)-3-cephem-4-carboxylate, 4-methoxybenzyl ester To a solution of (7R)-7-[(phenylacetyl)amino]-3-(3-hydroxymethylpyrid-4-ylthio)-3-cephem-4-carboxylate, 4-methoxybenzyl ester (112 mg, 0.194 mmol) and lithium chloride (14 mg, 0.581 mmol) in DMF at 0° C. was added diisopropylethylamine (0.101 mL, 0.581 mmol) and methanesulfonyl chloride (0.045 mL, 0.581 mmol). After 45 min, the reaction mixture was partitioned between water and ethyl acetate/hexane (v/v, 3/1). Purification on silica gel (Chromatotron, 2% MeOH/dichloromethane) afforded the title compound (52 mg, 45%). 1H NMR (CDCl$_3$) δ 3.17 (d, 1H, J=18), 3.59 (d, 1H, J=18), 3.63 (d, 1H, J=18), 3.68 (d, 1H, J=18), 3.77 (s, 3HH), 4.54 (d, 1H, J=13), 4.66 (d, 1H, J=13), 5.06 (d, 1H, J=5), 5.08 (d, 1H, J=13), 5.22 (d, 1H, J=13), 5.90 (dd, 1H, J=9, 5), 6.76 (d, 2H, J=8), 6.95 (d, 1H, J=9), 7.07 (d, 1H, J=5), 7.15 (d, 2H, J=8), 7.30 (m, 5H), 8.41 (d, 1H, J=5), 8.45 (s, 1H).

Example 8
(7R)-7-[(phenylacetyl)amino]-3-(3-isothioureidomethylpyrid-4-ylthio)-3-cephem-4-carboxylate, 4-methoxybenzyl ester, hydrochloride salt To a solution of (7R)-7-[(phenylacetyl)amino]-3-(3-chloromethylpyrid-4-ylthio)-3-cephem-4-carboxylate, 4-methoxybenzyl ester (52 mg, 0.087 mmol) in ethanol (0.4 mL) and dichloromethane (0.1 mL) was added thiourea (7 mg, 0.095 mmol) at room temperature. After overnight reaction the solvents were removed with rotary evaporator and the residue was triturated with ethyl ether. The solid precipitate was then dried in vacuum to afford the title compound (56 mg, 96%). 1H NMR (CDCl$_3$/CD$_3$OD) δ 3.14 (d, 1H, J=10), 3.53 (d, 1H, J=10), 3.58 (s, 2H), 3.73 (s, 3H), 4.40 (s, 2H), 5.03 (d, 1H, J=5), 5.12 (d, 1H, J=9), 5.15 (d, 1H, J=9), 5.75 (d, 1H, J=5), 6.74 (d, 2H, J=10), 7.10 (d, 1H, J=5), 7.14 (d, 2H, J=10), 7.25 (m, 5H), 8.30 (d, 1H, J=5), 8.45 (s, 1H).

Example 9
(7R)-7-[(phenylacetyl)amino]-3-(3-isothioureidomethylpyrid-4-ylthio)-3-cephem-4-carboxylate, trifluoroacetic acid salt To a solution of (7R)-7-[(phenylacetyl)amino]-3-(3-isothioureidomethylpyrid-4-ylthio)-3-cephem-4-carboxylate, 4-methoxybenzyl ester hydrochloride (56 mg, 0.083 mmol) in dichloromethane (1 mL) was added anisole (0.1 ml) followed by addition of trifluoroacetic acid (1 mL). After 30 min, the reaction mixture was concentrated with rotary evaporator and the residue was triturated with ethyl ether. The precipitate was repeatedly washed by decantation with fresh portions of ethyl ether and dried in vacuum to afford the title compound (49 mg, 79%). 1H NMR ($CD_3OD$) δ 3.20 (d, 1H, J=18), 3.58 (d, 1H, J=13), 3.62 (d, 1H, J=13), 3.83 (d, 1H, J=18), 4.56 (d, 1H, J=10), 4.60 (d, 1H, J=10), 5.25 (d, 1H, J=5), 5.78 (d, 1H, J=5), 7.28 (m, 5H), 7.43 (d, 1H, J=5), 8.45 (d, 1H, J=5), 8.55 (s, 1H).

Example 10

(7R)-7-[(Z)-2-(N-triphenylmethylaminothiazol-4-yl)-2-(triphenylmethoxyimino)acetamido]-3-(4-chloromethyl-1,2,3-thiadiazol-5-ylthio)-3-cephem-4-carboxylate, 4-methoxybenzyl ester To a suspension of (Z)-2-(N-triphenylmethylaminothiazol-4-yl)-2-(triphenylmethoxyimino)acetate sodium salt (2.11 g, 3.05 mmol) in DMF (4 mL) was added methanesulfonyl chloride (0.28 mL) at −60° C. and stirred at the same temperature for 1.5 h. The solution was then added to a solution of (7R)-7-amino-3-(4-chloromethyl-1,2,3-thiadiazol-5-yl)thio-3-cephem-4-carboxylate, 4-methoxybenzyl ester hydrochloride (920 mg, 1.88 mmol) and diisopropylethylamine (0.4 mL) in DMF (2 mL) at −10° C. and stirred for 1 h. The reaction mixture was poured into ice-water and the resulting precipitate was collected by filtration. The filter cake was purified by silica gel column chromatography (0.5% methanol/dichloromethane), affording 558 mg of the title compound. 1H NMR ($CDCl_3$) δ 3.07 (d, 1H, J=18), 3.44 (d, 1H, J=18), 3.81(2H), 4.96 (2H), 5.06 (1H), 6.07 (1H), 6.43 (s, 1H), 6.80 (br s, 1H), 6.88 (1H), 7.25–7.45 (40H).

Example 11

(7R)-7-[(Z)-2-(aminothiazol-4-yl)-2-(hydroxyimino)acetamido]-3-(4-isothioureidomethyl-1,2,3-thiadiazol-5-ylthio)-3-cephem-4-carboxylate, trifluoroacetic acid salt A solution of (7R)-7-[(Z)-2-(N-triphenylmethylaminothiazol-4-yl)-2-(triphenylmethoxyimino)acetamido]-3-(4-chloromethyl-1,2,3-thiadiazol-5-ylthio)-3-cephem-4-carboxylate, 4-methoxybenzyl ester(221 mg, 0.19 mmol), sodium iodide (34 mg, 0.23 mmol) and thiourea (14 mg, 0.18 mmol) in acetonitrile (10 mL) was stirred at 45° C. for 3 h. The resulting mixture was partitioned between water and ethyl acetate. The ethyl acetate layer was washed with water and concentrated. The residue was triturated to obtain the isothiouronium salt, which was subjected to the substantially the same conditions for deprotection as used in Example 9, affording 27 mg of the title compound. 1H NMR ($D_2O$) δ 3.48 (d, 1H, J=18), 3.84 (d, 1H, J=18), 5.39 (s, 1H), 5.90 (s, 1H), 7.16 (s, 1H).

Example 12

4-ethoxycarbonyl-5-[2-(phenylsulfonyl)ethylthiolthiazole

To a solution of potassium tert-butoxide (496 mg, 4.4 mmol) in 10 ml of THF was added a solution of ethyl isocyanoacetate (0.48 ml, 4.4 mmol) in 5 ml of THF at −40° C. and the reaction mixture was continued to stir for 10 min. After the reaction was cooled down to −60° C., a solution carbon disulfide in 5 ml of THF was added. The resulting mixture was allowed to warm up to 0° C. and 2-iodoethyl phenyl sulfone (4.4 mmol) was added. The mixture was then stirred at refluxed condition for 5 hours. After it was cooled down to room temperature, water and ethyl acetate were added. The aqueous layer was adjusted to acidic condition with dilute hydrochloric acid and extracted with ethyl acetate. The combined organic layer was dried with anhydrous sodium sulfate and the solvent was removed under reduced pressure. The crude residue was purified by chromatography to give the title compound (890 mg, 56%). 1H NMR ($CDCl_3$) δ 1.40 (t, 3H, J=7), 3.3–3.5 (m, 4H), 4.40 (q, 2H, J=7), 7.6 (t, 2H, J=8), 7.70 (t, 1H, J=8), 7.93 (d, 2H, J=8), and 8.64 (s, 1H).

Example 13

4-hydroxymethyl-5-[2-(phenylsulfonyl)ethylthio]thiazole

To a solution of 4-ethoxycarbonyl-5-[2-(phenylsulfonyl)ethylthio]thiazole (702 mg, 2 mmol) in 20 ml of THF was added lithium borohydride (2M, 1 ml) and methanol (0.16 ml, 4 mmol) at −30° C. The reaction mixture was allowed slowly warm up to room temperature and stirred overnight. The solvent was removed under reduced pressure and the crude residue was subjected to chromatography by using dichloromethane and methanol as the eluent to give the title compound (400 mg, 65%). 1H NMR ($CDCl_3$) δ 2.55 (s, 1H), 3.00 (t, 2H, J=6), 3.40 (t, 2H, J=6), 4.71 (s, 2H), 7.6 (t, 2H, J=7), 7.68 (t, 1H, J=7), 7.82 (d, 2H, J=7), and 8.80 (s, 1H).

Example 14

(7R)-7-[(Z)-2-(N-triphenylmethylaminothiazol-4-yl)-2-(triphenylmethoxyimino)acetamido]-3-(4-hydroxymethylthiazol-5-ylthio)-3-cephem-4-carboxylate, 4-methoxybenzyl ester To a solution of 4-hydroxymethyl-5-[2-(phenylsulfonyl)ethylthio]thiazole (39 mg) in 1 ml of DMF was added potassium t-butoxide (14 mg) and the resulting mixture was continued to stir for 2 hours. After the reaction solution was cooled down to −40° C., a solution of (7R)-7-[(Z)-2-(N-triphenylmethylaminothiazol-4-yl)-2-(triphenylmethoxyimino)acetamido]-3-trifluoromethanesulfonyloxy-3-cephem-4-carboxylate, 4-methoxybenzyl ester (104 mg) in 1.5 ml of DMF was added. The mixture was allowed slowly warm up to 0° C., quenched with dilute aqueous ammonium chloride, and extracted with ethyl acetate and hexane. The solvent was removed under reduced pressure and the crude residue was purified by chromatography to give the title compound (61 mg). 1H NMR ($CDCl_3$) δ 3.28 (q, 2H, J=8), 3.82 (s, 3H), 4.72 (q, 2H, J=8 Hz), 4.98 (d, 1H, J=4), 5.25 (q, 2H, J=8), 5.96 (q, 1H, J=4), 6.42 (s, 1H), 6.85 (s, 1H), 6.93 (d, 2H, J=7), 7.20–7.42 (m, 33H), and 8.8 (s, 1H).

Example 15

(7R)-7-[(Z)-2-(N-triphenylmethylaminothiazol-4-yl)-2-(triphenylmethoxyimino)acetamido]-3-(4-chloromethylthiazol-5-ylthio)-3-cephem-4-carboxylate, 4-methoxybenzyl ester To DMF (1 ml) was added thionyl chloride (0.016 ml) at 0° C. and the resulting mixture was continued to stir at the same temperature for 30 min. The resulting solution was canulated to a solution of (7R)-7-[(Z)-2-(N-triphenylmethylaminothiazol-4-yl)-2-(triphenylmethoxyimino)acetamido]-3-(4-hydroxymethylthiazol-5-ylthio)-3-cephem-4-carboxylate, 4-methoxybenzyl ester (61 mg) in 1 ml of DMF and continued to stir at the same temperature for 1 hour. The reaction solution was diluted with ethyl acetate and hexane, and was washed with water. The solvent was removed under reduced pressure and the crude residue was purified by chromatography to give the title compound (43 mg). 1H NMR ($CDCl_3$)

δ 3.22 (q, 2H, J=12), 3.80 (s, 3H), 4.78 (q, 2H, J=8), 5.04 (d, 1H, J=4), 5.30 (q, 2H, J=5), 6.00 (q, 1H, J=4), 6.42 (s, 1H), 6.72 (s, 1H), 6.92 (d, 2H, J=7), 7.08 (d, 1H, J=4), 7.20–7.45 (m, 32H), and 8.95 (s, 1H).

Example 16
(7R)-7-[(Z)-2-(N-triphenylmethylaminothiazol-4-yl)-2-(triphenylmethoxyimino)acetamido]-3-(4-isothioureidomethylthiazol-5-ylthio)-3-cephem-4-carboxylate, 4-methoxybenzyl ester (7R)-7-[(Z)-2-(N-triphenylmethylaminothiazol-4-yl)-2-(triphenylmethoxyimino)acetamido]-3-(4-chloromethylthiazol5-ylthio)-3-cephem-4-carboxylate, 4-methoxybenzyl ester (43 mg) was dissolved in 2 ml of acetonitrile, to which was added thiourea (4.5 mg) and sodium iodide (13 mg). The resulting mixture was stirred at room temperature overnight. The solvent was removed under reduced pressure and the crude residue was purified by flash chromatography to give the title compound(40 mg). 1H NMR (CDCl$_3$/CD$_3$OD) δ 3.2 (q, 2H, J=12), 3.80 (s, 3H), 4.4 (q, 2H, J=12), 5.02 (d, 1H, J=4 5.25 (q, 2H, J=5), 5.85 (d, 1H, J=4), 6.45 (s, 1H), 6.90 (d, 2H, J=7), 7.2–7.4 (m, 32H), and 9.00 (s, 1H).

Example 17
(7R)-7-[(Z)-2-(aminothiazol-4-yl)-2-(hydroxyimino) acetamido]-3-(4-isothioureidomethylthiazol-5-ylthio)-3-cephem-4-carboxylate, trifluoroacetic acid salt (7R)-7-[(Z)-2-(N-triphenylmethylaminothiazol-4-yl)-2-(triphenylmethoxyimino)acetamido]-3-(4-isothioureidomethylthiazol-5-ylthio)-3-cephem-4-carboxylate, 4-methoxybenzyl ester(40 mg) was dissolved in 0.1 ml of anisole and 0.9 ml of dichloroacetic acid. The resulting mixture was stirred at room temperature for 3 hours and then precipitated by addition of diethyl ether (100 ml). The precipitate was filtered and subjected to HP-20 reverse phase chromatography to give the title compound. 1H NMR (D$_2$O) δ 3.60 (q, 2H, J=6), 4.60 (q, 2H, J=10), 5.20 (d, 1H, J=4), 5.80 (d, 1H, J=4), 6.90 (s, 1H), and 9.13 (s, 1H). IR (KBr) 997, 1042, 1180, 1349, 1386, 1533, 1615, 1655, and 1768 cm$^{-1}$.

Example 18
(Z)-2-(2-amino-5-chlorothiazol-4-yl)-2-(triphenylmethoxyimino)acetic acid To a solution of (Z)-2-(2-aminothiazol-4-yl)-2-(triphenylmethoxyimino)acetic acid (5.81 g, 13.47 mmol) in DMF (30 mL) at room temperature (1 mL) was added N-chlorosuccinimide (1.80 g, 13.47 mmol). After overnight reaction the reaction mixture was poured into water (about 500 mL) and the resulting precipitate was filtered, washed with water and then with ethyl acetate and dried in vacuum to afford 4.43 g (71%) of the title compound. 13C NMR (CDCl$_3$) δ 108.5, 125.6, 126.2, 126.6, 12.3, 134.7, 141.8, 146.5, 162.1, 163.3.

Example 19
(7R)-7-[(Z)-2-(2-amino-5-chlorothiazol-4-yl)-2-(triphenylmethoxyimino)acetamido]-3-chloro-3-cephem-4-carboxylate diphenylmethyl ester To a solution of 7-amino-3-chlorocephalosporanic acid diphenylmethyl ester toluenesulfonic acid salt (5.0 g, 8.72 mmol) in dry THF (100 ml) was added pyridine (0.63 g, 10.0 mmol) at room temperature followed by addition of (Z)-2-(2-amino-5-chlorothiazol-4-yl)-2-(triphenylmethoxy imino) acetic acid (5.81 g, 13.47 mmol). The resulting slurry was cooled to −15° C. and additional pyridine (1.42 g, 22.5 mmol) was added followed by dropwise addition of phosphorous oxychloride(1.64 g, 17.5 mmol) while maintaining reaction temperature below −10° C. After 30 min. reaction ethyl acetate (200 mL) was added followed by addition of water (150 mL). Aqueous layer was thoroughly extracted with ethyl acetate and the combined organic extracts were dried over sodium sulfate and concentrated in vacuum to yield crude product which was purified by flash column chromatography on silica gel (ethyl acetate/hexane-3/1) to afford the title compound (5.37 g, 65%). 1H NMR (CDCl$_3$/CD3OD) δ 3.35 (d, 1H, J=18), 3.68 (d, 1H, J=18), 5.07 (d, 1H, J=5), 5.80 (br s, 2H), 6.04 (dd, 1H, J=9, 5), 7.03 (s, 1H), 7.06 (d, 1H, J=9), 7.22–7.50 (m, 25H).

Example 20
(7R)-7-[(Z)-2-(2-amino-5-chlorothiazol-4-yl)-2-(triphenylmethoxyimino)acetamido]-3-mercapto-3-cephem-4-carboxylate diphenylmethyl ester To a solution of (7R)-7-[(Z)-2-(2-amino-5-chlorothiazol-4-yl)-2-(triphenylmethoxyimino)acetamido]-3-chloro-3-cephem-4-carboxylate diphenylmethyl ester (4.0 g, 4.72 mmol) in DMF (30 mL) cooled to −20° C. was added in one portion powdered sodium hydrogen sulfide hydrate (1.1 g, 19.6 mmol). After 15 min the reaction mixture was poured into 0.5 M monosodium phosphate (about 100 mL), extracted with ethyl acetate and the organic layer was washed thoroughly with water. After concentrating in vacuum the crude title product was obtained as yellow foam 3.8 g (95%). 1H NMR (CDCl$_3$/CD3OD) δ 3.38 (d, 1H, J=15), 4.43 (d, 1H, J=15), 5.03 (d, 1H, J=5), 5.80 (d, 1H, J=5), 5.99 (br s, 1H), 6.80 (s, 1H), 7.05–7.50 (m, 25H).

Example 21
3-chloromethyl-4-chloropyridine hydrochloride

Thionyl chloride (0.714 mL, 9.78 mmol) was added at room temperature to dry DMF (7 mL). After 30 min the above solution was cannulated into the solution of 3-hydroxymethyl-4-chloropyridine (700 mg, 4.89 mmol) in DMF (3 mL). After 45 min, the product was precipitated by addition of dry ether (100 ml), washed with ether, and dried in vacuum to yield 813 mg (84%) of the title compound. 1H NMR (CD$_3$OD) δ 5.00 (s, 2H), 8.31 (d, 1H, J=5), 8.99 (d, 1H, J=5), 9.18 (s, 1H).

Example 22
3-(N-tert-butoxycarbonylaminoethylthiomethyl)-4-chloropyridine

To a solution of 3-chloromethyl-4-chloropirydine hydrochloride (513 mg, 2.59 mmol) in DMF (6 mL) at room temperature were added sodium iodide (386 mg, 2.59 mmol), diisopropylethylamine (1.12 mL, 6.47 mmol) and 2-(N-tert-butoxycarbonylamino)ethanethiol (458 mg, 2.59 mmol). After 2 h, the reaction mixture was partitioned between dilute HCl and ethyl acetate. The organic layer was washed with water, dried over sodium sulfate, and concentrated to yield 750 mg of the oily product (96%), which was used for the next step without further purification. 1H NMR (CDCl$_3$) δ 1.43 (s, 9H), 2.61 (m, 2H), 3.35 (m, 2H), 3.81 (s, 2H), 4.90 (br s, 1H), 7.35 (d, 1H, J=4), 8.40 (d, 1H, J=4), 8.57 (s, 1H).

Example 23
(7R)-7-[(Z)-2-(2-amino-5-chlorothiazol-4-yl)-2-(triphenylmethoxyimino)acetamido]-3-(3-N-tert-butoxycarbonylaminoethylthiomethylpyrid-4-ylthio)-3-cephem-4-carboxylate diphenylmethyl ester To a solution of (7R)-7-[(Z)-2-(2-amino-5-chlorothiazol-4-yl)-2-(triphenylmethoxyimino)acetamido]-3-mercapto-3-cephem-4-carboxylate diphenylmethyl ester (650 mg, 0.777 mmol) in DMF (3 mL) was added 3-(N-tert-butoxycarbonylaminoethylthiomethyl)-4-chloropyridine (242 mg, 0.80 mmol) at room temperature. After overnight reaction the reaction mixture was partitioned between water and ethyl acetate. The organic layer was thoroughly washed with water, dried over sodium sulfate, and concentrated to yield the crude product which was purified by radial chromatography on silica gel (dichloromethane/methanol; v/v, 50/1) to afford 220 mg of the title compound (26%). 1H NMR (CDCl$_3$/CD$_3$OD) δ 1.23 (s, 9H), 2.32 (t, 2H, J=6), 2.98 (d, 1H, J=18), 3.06 (m, 2H), 3.40 (d, 1H, J=18), 3.46 (s, 2H), 5.03 (d, 1H, J=5), 5.52 (br s, 1H), 5.94 (d, 1H, J=5), 6.80 (s, 1H), 6.90 (d, 1H, J=6), 7.00–7.22 (m, 25H), 8.01 (d, 1H, J=6), 8.08 (s, 1H).

Example 24

(7R)-7-[(Z)-2-(2-amino-5-chlorothiazol-4-yl)-2-(hydroxyimino)acetamido]-3-(3-aminoethylthiomethylpyrid-4-ylthio]-3-cephem-4-carboxylate, methanesulfonic acid salt To a solution of (7R)-7-[(Z)-2-(2-amino-5-chlorothiazol-4-yl)-2-(triphenylmethoxyimino)acetamido]-3-(3-N-tert-butoxycarbonylamino ethylthiomethylpyrid-4-ylthio)-3-cephem-4-carboxylate diphenylmethyl ester(1.0 g, 0.907 mmol) in dichloromethane (10 mL) and anisole (1.0 mL) was added at 0° C. trifluoroacetic acid (13 mL). After 1.5 hr the reaction mixture was concentrated in vacuum at room temperature and the oily residue was dissolved in 98% formic acid (20 mL). After 4 hr at room temperature formic acid was removed in vacuum and the residue was dissolved in water (25 mL). The insoluble material was removed by centrifugation and the supernatant was purified on HP20 column by elution with water followed by 0.1 M ammonium acetate, water and finally eluting the product with acetonitrile/water (1/4). The eluate was concentrated to about 1/10 original volume and the resulting precipitate was filtered, washed with water and dried in vacuum to yield zwitterionic product (260 mg). The methanosulfonate salt was prepared by suspending the above material in water (15 mL) followed by addition of methanesulfonic acid (1.0 M in water, 0.98 eq) and acetonitrile (5 mL). After evaporation of the resulting solution to dryness the residue was dissolved in water (30 mL), centrifuged to remove insoluble material and the supernatant was lyophilized to produce the title compound (274 mg, 44%). 1H NMR (D$_2$O) δ 3.11 (s, 3H), 3.19 (m, 2H), 3.52 (m, 2H), 3.67 (d, 1H, J=17), 4.22 (d, 1H, J=17), 4.33 (s, 2H), 5.76 (d, 1H, J=4), 6.29 (d, 1H, J=4), 7.93 (d, 1H, J=4), 8.78 (d, 1H, J=4), 8.87 (s, 1H).

Example 25

3-(N-tert-butoxycarbonylaminoethylthio)-4-chloropyridine

To a suspension of 4-chloropyridine hydrochloride (2 g) in 40 mL of dry THF was added a freshly prepared LDA (2.5 eq.) at −70° C. and the resulting mixture was continued to stir at the same temperature for 4 hours. A solution of N,N'-di(tert-butoxycarbonyl)cystamine (2.5 g, 0.5 eq.) in 10 ml of THF was cannulated to the above solution. The reaction mixture was allowed to warm up to 0° C., quenched with water and then extracted with ethyl acetate. The solvent was removed under reduced pressure and the crude residue was purified by flash chromatography to give of the title compound(0.95 g, 50%) as a white solid. 1H NMR (CDCl$_3$) δ 1.42 (s, 9H), 3.15 (t, 2H, J=7), 3.38 (t, 2H, J=7), 4.95 (s, 1H), 7.32 (d, 1H, J=6), 8.35 (d, 1H, J=6), and 8.60 (s, 1H).

Example 26

(7R)-7-[(Z)-2-(2-amino-5-chlorothiazol-4-yl)-2-(triphenylmethoxyimino)acetamido]-3-[3-(N-tert-butoxycarbonylaminoethylthio)pyridyl-4-thio]-3-cephem-4-carboxylate, diphenylmethyl ester To a stirring solution of (7R)-7-[(Z)-2-(2-amino-5-chlorothiazol-4-yl)-2-(triphenylmethoxyimino)acetamido]-3-mercapto-3-cephem-4-carboxylate, diphenylmethyl ester (6.7 g, 7.8 mmol) in 20 ml of dry DMF was added 3-(N-tert-butoxycarbonylaminoethylthio)-4-chloropyridine (2.3 g, 7.8 mmol) at −20° C. The reaction mixture was allowed to slowly warm up to room temperature and stirred overnight. The reaction mixture was diluted with ethyl acetate and hexane and washed with water. The solvent was removed under reduced pressure and the crude residue was purified by chromatography to give the title compound (6 g, 68%) as a yellow solid. 1H NMR (CDCl$_3$) δ 1.40 (s, 9H), 2.75 (t, 2H, J=7), 3.10 (t, 2H, J=7), 3.15 (d, 1H, J=14), 3.60 (d, 1H, J=14), 4.95 (s, 1H), 5.20 (d, 1H, J=4), 5.90 (s, 2H), 6.25 (q, 1H, J=4), 6.85 (d, 1H, J=4), 6.90 (s, 1H), 7.15–7.4 (m, 26H), 8.1 (s, 1H), 8.21 (d, 1H, J=7).

Example 27

(7R)-7-[(Z)-2-(2-amino-5-chlorothiazol-4-yl)-2-(hydroxyimino)acetamido]-3-(3-aminoethylthiopyrid-4-ylthio)-3-cephem-4-carboxylate, trifluoroacetic acid salt To a solution of (7R)-7-[(Z)-2-(2-amino-5-chlorothiazol-4-yl)-2-(triphenylmethoxyimino)acetamido]-3-[3-(N-tert-butoxycarbonylaminoethylthio)pyridyl-4-thio]-3-cephem-4-carboxylate, diphenylmethyl ester (6 g) in 10 ml of dichloromethane and 1 ml of anisole was added 10 ml of trifluoroacetic acid at 0° C. and the resulting solution was stirred at room temperature for 1 hour. After the solvent was removed, the residue was redissolved in 20 ml formic acid and stirred at room temperature overnight. The solvent was removed under reduced pressure. The residue was dried over high vacuum and then triturated with ethyl acetate. The resulting solid was subjected to reverse phase chromatography on Amberchrom column (0.1% aqueous trifluoroacetic acid/acetonitrile) to give the title compound(1.5 g, 48%). 1H NMR (D$_2$O) δ 3.5–3.7 (m, 4H), 3.8 (d, 1H, J=14), 4.4 (d, 1H, J=14), 5.84 (d, 1, J=4), 6.4 (d, 1H, J=4), 7.65 (d, 1H, J=6), 8.82 (d, 1H, J=6), and 9.02 (s, 1H). IR (KBr) 778, 1042, 1173, 1541, 1610, 1780, 3187 cm$^{-1}$.

Example 28

(7R)-7-[(Z)-2-(aminothiazol-4-yl)-2-(triphenylmethoxyoxyimino)acetamido]-3-(4-(2-tert-butoxycarbonylaminoethylthiomethyl)-1,2,3-thiadiazol-5-ylthio)-3-cephem-4-carboxylate, benzhydryl ester To a solution of 4-[(2-tert-butoxycarbonylaminoethyl)thiomethyl]-5-(2-ethoxycarbonylethyl)thio-1,2,3-1,2,3-thiadiazole (181 mg, 0.44 mmol) in ethanol (5 mL) was added sodium methoxide in methanol (0.55M, 1 mL), and concentrated. The residue was triturated with hexane-ethyl acetate(9:1), mixed with (7R)-7-[[(Z)-2-(2-aminothiazol-4-yl)-2-(triphenylmethoxyimino)acetyl]amino]-3-chloro-3-cephem-4-carboxylate, diphenylmethyl ester (200 mg, 0.25 mmol), and dissolved in a mixed solvent of ethanol and dichloromethane. The solution was stirred at room temperature for 16 h, and concentrated. The crude was purified by silica gel column chromatography (3% methanol/dichloromethane), affording 100 mg of the title compound. 1H NMR (CDCl$_3$) δ 1.46 (9H), 2.68 (2H), 3.19 (d, 1H, J=18), 3.33 (2H+1H), 4.03(2H), 4.88 (br s, 1H), 5.09 (1H), 5.93 (br s, 2H), 6.44 (s, 1H), 7.03 (1H), 7.20–7.45 (25H).

Example 29

(7R)-7-[(Z)-2-(aminothiazol-4-yl)-2-(hydroxyimino)acetamido]-3-(4-(2-aminoethylthiomethyl)-1,2,3-thiadiazol-5-ylthio)-3-cephem-4-carboxylate, dichloroacetic acid salt (7R)-7-[(Z)-2-(aminothiazol-4-yl)-2-(triphenylmethoxyoxyimino)acetamido]-3-(4-(2-aminoethylthiomethyl)-1,2,3-thiadiazol-5-ylthio)-3-cephem-4-carboxylate, diphenylmethyl ester (82 mg, 0.076 mmol) was dissolved in 0.8 mL of dichloroacetic acid containing 5% anisole and stirred at room temperature overnight. Excess diethyl ether was added and the resulting precipitate was collected by filtration. The filter cake was purified by HP-20 reverse phase column chromatography, affording 16 mg of the title compound. 1H NMR (DMSO-$d_6$) δ 2.64(2H), 2.90 (2H), 3.4 (1H, overlapped with water), 3.82 (d, 1H, J=17), 4.04 (d, 1H, J=15), 4.14 (d, 1H, J=15), 5.17 (d, 1H, J=5), 5.74 (dd, 1H, J=5, 8), 6.64 (s, 1H), 7.08 (s, 1H), 9.50 (d, 1H, J=8).

Example 30

3-(2-N-tert-butoxycarbonylaminoethoxymethyl)-4-chloropyridine

A diphasic mixture of 4-chloro-3-chloromethylpyridine hydrochloride (396 mg, 2 mmol), N-tert-butoxycarbonylaminoethanol (132 mg, 2 mmol) and benzyl triethyl ammonium bromide (544 mg, 2 mmol) in toluene (20 mL) and 50% sodium hydroxide aqueous solution was vigorously stirred at room temperature for 24 h. The organic layer was taken and concentrate to afford 490 mg of the title compound. 1H NMR (CDCl$_3$) δ 1.46 (s, 9H), 3.39 (2H), 3.65 (2H), 4.64 (s, 2H), 4.90 (br s, 1H), 7.33 (d, 1H, J=5), 8.46 (d, 1H, J=5), 8.64 (s, 1H).

Example 31

(7R)-7-[(Z)-2-(2-amino-5-chlorothiazol-4-yl)-2-(triphenylmethoxyimino)acetamido]-3-(3-(2-tert-butoxycarbonylaminoethoxymethyl)pyrid-4-ylthio)-3-cephem-4-carboxylate, diphenylmethyl ester Under substantially the same conditions as used in Example 26, (7R)-7-[(Z)-2-(2-amino-5-chlorothiazol-4-yl)-2-(triphenylmethoxyimino)acetamido]-3-mercapto-3-cephem-4-carboxylate, diphenylmethyl ester was reacted with 3-(2-N-tert-butoxycarbonylaminoethoxymethyl)-4-chloropyridine to afford the title compound. 1H NMR (CDCl$_3$) δ 1.42 (9H), 3.11 (d, 1H, J=18), 3.24 (2H), 3.40 (2H), 3.46 (d, 1H, J=18), 4.30 (2H), 4.83 (br s, 1H), 5.17 (1H), 5.72 (br s, 2H), 6.20 (1H), 6.99 (s, 1H), 7.25–7.45 (25H), 8.28 (1H), 8.33 (1H).

Example 32

(7R)-7-[(Z)-2-(2-amino-5-chlorothiazol-4-yl)-2-(hydroxyimino)acetamido]-3-(3-(2-aminoethoxymethyl)pyrid-4-ylthio)-3-cephem-4-carboxylate, trifluoroacetic acid salt (7R)-7-[(Z)-2-(2-amino-5-chlorothiazol-4-yl)-2-(triphenylmethoxyimino)acetamido]-3-(3-(2-tert-butoxycarbonylaminoethoxymethyl)pyrid-4-ylthio)-3-cephem-4-carboxylate, diphenylmethyl ester was subjected to deprotection under substantially the same conditions as used in Example 27, affording the title compound. 1H NMR (D$_2$O) δ 3.35 (2H), 3.45 (d, 1H, J=18), 3.91 (2H), 4.00 (d, 1H, J=18), 5.52 (d, 1H, J=5), 6.04 (d, 1H, J=5), 7.73 (d, 1H, J=6), 8.57 (d, 1H, J=6), 8.65 (s, 1H).

Example 33

3-(N-tert-butoxycarbonylaminoethylsulfonylmethyl)-4-chloropyridine

To a solution of 3-(N-tert-butoxycarbonylaminoethyl) thiomethyl)-4-chloropyridine (302 mg, 1 mmol) in a mixed solvents of ethyl acetate (10 mL) and methanol (5 mL) was added methanesulfonic acid (144 mg, 1.5 mmol). 3-chloroperoxybenzoic acid (700 mg) was added and stirred at room temperature for 5 h. The reaction was quenched with saturated sodium thiosulfate aqueous solution. The solution was neutralized with 10% sodium hydroxide and extracted with ethyl acetate. The ethyl acetate extract was dried over sodium sulfate and concentrated to dryness, affording 286 mg of the title compound. 1H NMR (CDCl$_3$) δ 1.44 (9H), 3.22 (2H), 3.66 (2H), 4.50 (s, 2H), 5.21 (br s,1H), 7.42 (d, 1H, J=5), 8.54 (s,1H, J=5), 8.72 (1H).

Example 34

(7R)-7-[(Z)-2-(2-amino-5-chlorothiazol-4-yl)-2-(triphenylmethoxyimino)acetamido]-3-(3-N-tert-butoxycarbonylaminoethylsulfonylmethylpyrid-4-ylthio)-3-cephem-4-carboxylate, diphenylmethyl ester Under substantially the same conditions as used in Example 26, (7R)-7-[(Z)-2-(2-amino-5-chlorothiazol-4-yl)-2-(triphenylmethoxyimino)acetamido]-3-mercapto-3-cephem-4-carboxylate, diphenylmethyl ester was reacted with 3-(N-tert-butoxycarbonylaminoethylsulfonylmethyl)-4-chloropyridine to afford the title compound. 1H NMR (CDCl$_3$) δ 1.44 (9H), 3.20(3H), 3.66 (3H), 4.48 (s, 2H), 5.19 (1H), 7.25–7.45 (25H), 8.50 (s,1H, J=5), 8.70 (1H).

Example 35

(7R)-7-[(Z)-2-(2-amino-5-chlorothiazol-4-yl)-2-(hydroxyimino)acetamido]-3-(3-aminoethylsulfonylmethylpyrid-4-ylthio)-3-cephem-4-carboxylate, trifluoroacetic acid salt (7R)-7-[(Z)-2-(2-amino-5-chlorothiazol-4-yl)-2-(triphenylmethoxyimino)acetamido]-3-(3-N-tert-butoxycarbonylamino ethylsulfonylomethylpyrid-4-ylthio)-3-cephem-4-carboxylate, diphenylmethyl ester was subjected to deprotection under substantially the same conditions as used in Example 27, affording the title compound. 1H NMR (D$_2$O) δ 3.47 (d, 1H, J=18), 3.3.70 (2H), 3.85 (2H), 4.02 (d, 1H, J=18), 5.07(s, 2H), 5.52 (d, 1H, J=5), 6.03 (d, 1H, J=5), 7.79 (d, 1H, J=6), 8.64 (d, 1H, J=6), 8.76 (s, 1H).

Example 36

3-(4-N-tert-butoxycarbonylaminobutyn-1-yl)-4-chloropyridine 4-chloro-3-chloromethylpyridine hydrochloride was reacted with 3-t-BOC-amino-1-propyne under the phase transfer condition described in Example 30, affording the title compound. 1H NMR (CDCl$_3$) δ 1.4–1.6 (9H, rotomeric mixture), 4.0–4.2 (2H), 7.32 (d, 1H, J=5), 8.43 (d, 1H, J=5), 8.53 (s, 1H).

Example 37

(7R)-7-[(Z)-2-(2-amino-5-chlorothiazol-4-yl)-2-(triphenylmethoxyimino)acetamido]-3-(3-(4-N-tert-butoxycarbonylaminobutyn-1-yl)pyrid-4-ylthio)-3-cephem-4-carboxylate, diphenylmethyl ester Under substantially the same conditions as used in Example 26, (7R)-7-[(Z)-2-(2-amino-5-chlorothiazol-4-yl)-2-(triphenylmethoxyimino)acetamido]-3-mercapto-3-cephem-4-carboxylate, diphenylmethyl ester was reacted with 3-(4-N-tert-butoxycarbonylaminobutyn-1-yl)-4-chloropyridine to afford the title compound. 1H NMR (CDCl$_3$) δ 1.4–1.8 (9H), 3.10 (d, 1H, J=18), 3.47 (d, 1H, J=18), 3.85 (2H), 5.16 (1H), 5.62 (br s, 2H), 6.13 (1H), 7.00 (1H), 7.2–7.5 (25H), 8.35 (2H).

Example 38

(7R)-7-[(Z)-2-(2-amino-5-chlorothiazol-4-yl)-2-(hydroxyimino)acetamido]-3-(3-(4-amino-2-butyn-1-yl) pyrid-4-ylthio)-3-cephem-4-carboxylate, trifluoroacetic acid salt (7R)-7-[(Z)-2-(2-amino-5-chlorothiazol-4-yl)-2-(triphenylmethoxyimino)acetamido]-3-(3-(4-N-tert-butoxycarbonylaminobutyn-1-yl)pyrid-4-ylthio)-3-cephem-4-carboxylate, diphenylmethyl ester was subjected to deprotection under substantially the same conditions as used in Example 27, affording the title compound. 1H NMR (D$_2$O) δ 3.46 (d, 1H, J=18), 4.02 (d, 1H, J=18), 4.16 (2H), 4.70 (2H), 5.52 (d, 1H, J=5), 6.03 (d, 1H, J=5), 7.76 (d, 1H, J=6), 8.66 (d, 1H, J=6), 8.78 (s, 1H).

Example 39

(7R)-7-[(Z)-2-(2-amino-5-chlorothiazol-4-yl)-2-(hydroxyimino)acetamido]-3-(3-(4-amino-2-(Z)-buten-1-yl)pyrid-4-ylthio)-3-cephem-4-carboxylate, trifluoroacetic acid salt (7R)-7-[(Z)-2-(2-amino-5-chlorothiazol-4-yl)-2-(triphenylmethoxyimino)acetamido]-3-(3-(4-tert-butoxycarbonylamino-2-(Z)-buten-1-yl)pyrid-4-ylthio)-3-cephem-4-carboxylate, diphenylmethyl ester was subjected to deprotection under substantially the same conditions as used in Example 27, affording the title compound, as a mixture with the 1-butenyl isomer. 1H NMR (D$_2$O) δ 3.46 (d, 1H, J=18), 3.91 (2H), 4.02 (d, 1H, J=18), 4.56 (2H), 5.52 (d, 1H, J=5), 5.63 (2H), 6.03 (d, 1H, J=5), 7.76 (d, 1H, J=6), 8.65 (d, 1H, J=6), 8.76 (s, 1H).

Example 40

3-(N-tert-butoxycarbonylaminoethylsulfenylmethyl)-4-chloropyridine

To a solution of 3-(N-tert-butoxycarbonylaminoethyl)thiomethyl)-4-chloropyridine (687 mg, 2.26 mmol) in methylene chloride (10 mL) at 0° C. was added 3-chloroperoxybenzoic acid (467, 2.72 mmol). After overnight reaction at room temperature reaction mixture was partitioned between dichloromethane and diluted sodium bicarbonate solution. The organic layer was dried over sodium sulfate and concentrated. Crystallization of the crude from ethyl acetate/hexane afforded the title compound. 1H NMR (CDCl$_3$) δ 1.40 (s, 9H), 2.90 (m, 1H), 3.01 (m, 1H), 3.59 (m, 2), 4.00 (d, 1H, J=13), 4.22 (d, 1H, J=13), 5.30 (br. s, 1H), 7.40 (d, 1H, J=4), 8.45 (d, 1H, J=4), 8.57 (s, 1H).

Example 41

(7R)-7-[(Z)-2-(2-amino-5-chlorothiazol-4-yl)-2-(hydroxyimino)acetamido]-3-(3-aminoethylsulfenylmethylpyrid-4-ylthio)-3-cephem-4-carboxylate, trifluoroacetic acid salt Under substantially the same conditions as used in Example 43, (7R)-7-[(Z)-2-(2-amino-5-chlorothiazol-4-yl)-2-(triphenylmethoxyimino)acetamido]-3-mercapto-3-cephem-4-carboxylate, diphenylmethyl ester was reacted with 3-(N-tert-butoxycarbonylaminoethylsulfenylmethyl)-4-chloropyridine to afford (7R)-7-[(Z)-2-(2-amino-5-chlorothiazol-4-yl)-2-(triphenylmethoxyimino)acetamido]-3-(3-N-tert-butoxycarbonylaminoethylsulfenylmethylpyrid-4-ylthio)-3-cephem-4-carboxylate, diphenylmethyl ester, which was then subjected to deprotection under substantially the same conditions as used in Example 35, affording the title compound. 1H NMR (D$_2$O) δ 2.90 (s, 3H), 3.20–3.35 (m, 1H), 3.50–3.70 (m, 4H), 4.00 (dd, 1H, J=18, 3), 4.55 (dd, 1H, J=13, 3), 4.65 (dd, 1H, J=13, 3), 5.51 (m, 1H), 6.02 (m, 1H), 7.75 (m, 1H), 8.60 (m, 2H).

Example 42

(7R)-7-{[2-[N,N'-bis-(t-butoxycarbonyl)guadinino]ethylthio]acetyl]amino}-3-(4-chloromethyl-1,2,3-thiadiazol-5-ylthio)-3-cephem-4-carboxylate, 4-methoxybenzyl ester To a solution of (7R)-7-amino-3-(4-chloromethyl-1,2,3-1,2,3-thiadiazol-5-ylthio)-3-cephem-4-carboxylate, 4-methoxybenzyl ester (485 mg, 0.794 mmol) and {2-[N$^w$, N$^{w'}$-bis-(t-butoxycarbonyl)guadinino]ethyl}thioacetic acid (329 mg, 0.873 mmol) were added phosphorous oxychloride (0.103 mL, 1.11 mmol) and diisopropylethyl amine (0.55 mL, 3.18 mmol), and was stirred at –10° C. for 16 h. Water was added, and the mixture was extracted with ethyl acetate. The organic extract was washed with aqueous sodium bicarbonate and then concentrated. The residue was purified by silica gel chromatography (1% methanol/dichloromethane), affording 440 mg of the title compound. $^1$H NMR (CD$_3$OD) d 1.44 (s, 9), 1.47 (s, 9), 2.79 (m, 2), 3.30 (2, overlapped with solvent), 3.35 (d, 1, J=18), 3.57 (m, 2), 3.64 (d, 1, J=18), 3.77 (s, 3), 4.96 (s, 2), 5.15 (d, 1, J=5), 5.20 (d, 1, J=12), 5.23 (d, 1, J=12), 5.77 (d, 1, J=5) 6.81 (d, 2, J=9), 7.25 (d, 1, J=8).

Example 43

(7R)-7-{[2-[N,N'-bis-(t-butoxycarbonyl)guadinino]ethylthio]acetyl]amino}-3-(4-isothiouroniummethylthiomethyl-1,2,3-thiadiazol-5-ylthio)-3-cephem-4-carboxylate, 4-methoxybenzyl ester, iodide salt A solution of (7R)-7-{[2-[N,N'-bis-(t-butoxycarbonyl)guadinino]ethylthio]acetyl]amino}-3-(4-chloromethyl-1,2,3-1,2,3-thiadiazol-5-ylthio)-3-cephem-4-carboxylate, 4-methoxybenzyl ester (200 mg, 0.24 mmol), thiourea (18 mg, 0.24 mmol) and sodium iodide (35 mg, 0.24 mmol) in acetonitrile (3 mL) was stirred at room temperature overnight. The mixture was concetrated and triturated with dichloromethane. The residue was redissolved in acetone (2 mL) and filtered. The filtrate was concentrated to dryness, affording 200 mg of the title compound. $^1$H NMR (CDCl$_3$) d 1.45 (s, 18), 2.81 (m, 2), 3.15 (d, 1, J=18), 3.36 (d, 1, J=15), 3.55 (d, 1, J=15), 3.62 (m, 2), 3.80 (s, 3), 3.83 (d, 1, J=18), 4.80 (d, 1, J=15), 4.86 (d, 1, J=15), 5.08 (d, 1, J=5), 5.23 (d, 1, J=12), 5.27 (d, 1, J=12), 5.58 (dd, 1, J=5, 8) 6.85 (d, 2, J=9), 7.37 (d, 2, J=9), 8.24 (d, 1, J=8).

Example 44

(7R)-7-{[(2-guadininoethylthio)acetyl]amino}-3-(4-isothiouroniummethylthiomethyl-1,2,3-thiadiazol-5-ylthio)-3-cephem-4-carboxylic acid, 2,2-dichloroacetate salt A solution of (7R)-7-{[2-[N,N'-bis-(t-butoxycarbonyl)guadinino]ethylthio]acetyl]amino}-3-(4-isothiouroniummethylthiomethyl-1,2,3-1,2,3-thiadiazol-5-ylthio)-3-cephem-4-carboxylate, 4-methoxybenzyl ester, iodide salt (200 mg) and anisole (0.1 mL) in dichloroacetic acid (2 mL) was stirred at room temperature for 16 h. The mixture was precipitated with diethylether/hexane, filtered, and vacuum-dried to afford 70 mg of the title compound.

Using substantially the same methods as described in the Examples above, the following additional compounds were prepared:

Example 45

(7R)-7-[(Z)-2-(2-aminothiazol-4-yl)-2-(hydroxyimino)acetamido]-3-[3-(2-aminoethylthio)pyrid-4-ylthio]-3-cephem-4-carboxylate, trifluoroacetic acid salt

Example 46

(7R)-7-[(Z)-2-(2-aminothiazol-4-yl)-2-(hydroxyimino)acetamido]-3-[3-(2-guanidinoethylthio)pyrid-4-ylthio]-3-cephem-4-carboxylate, trifluoroacetic acid salt

Example 47

(7R)-7-[(Z)-2-(2-aminothiazol-4-yl)-2-(hydroxyimino)acetamido]-3-[3-(2-N-(iminomethyl)aminoethylthio)pyrid-4-ylthio]-3-cephem-4-carboxylate, trifluoroacetic acid salt

Example 48
(7R)-7-[(Z)-2-(2-aminothiazol-4-yl)-2-(hydroxyimino) acetamido]-3-[3-(2-aminopropylthio)pyrid-4-ylthio]-3-cephem-4-carboxylate, trifluoroacetic acid salt

Example 49
(7R)-7-[(Z)-2-(2-aminothiazol-4-yl)-2-(hydroxyimino) acetamido]-3-[3-(2-guanidinopropylthio)pyrid-4-ylthio]-3-cephem-4-carboxylate, trifluoroacetic acid salt

Example 50
(7R)-7-[(Z)-2-(2-aminothiazol-4-yl)-2-(hydroxyimino) acetamido]-3-[3-(2-N-(iminomethyl)aminopropylthio) pyrid-4-ylthio]-3-cephem-4-carboxylate, trifluoroacetic acid salt

Example 51
(7R)-7-[(Z)-2-(2-aminothiazol-4-yl)-2-(hydroxyimino) acetamido]-3-[3-(2-amino-2-carboxamidoethylthio)pyrid-4-ylthio]-3-cephem-4-carboxylate, trifluoroacetic acid salt

Example 52
(7R)-7-[(Z)-2-(2-aminothiazol-4-yl)-2-(hydroxyimino) acetamido]-3-[3-(2-guanidino-2-carboxamidoethylthio) pyrid-4-ylthio]-3-cephem-4-carboxylate, trifluoroacetic acid salt

Example 53
(7R)-7-[(Z)-2-(2-aminothiazol-4-yl)-2-(hydroxyimino) acetamido]-3-[3-(2-N-(iminomethyl)amino-2-carboxamidoethylthio)pyrid-4-ylthio]-3-cephem-4-carboxylate, trifluoroacetic acid salt

Example 54
(7R)-7-[(Z)-2-(2-aminothiazol-4-yl)-2-(hydroxyimino) acetamido]-3-[3-(2-amino-3-hydroxypropylthio)pyrid-4-ylthio]-3-cephem-4-carboxylate, trifluoroacetic acid salt

Example 55
(7R)-7-[(Z)-2-(2-aminothiazol-4-yl)-2-(hydroxyimino) acetamido]-3-[3-(2-guanidino-3-hydroxypropylthio)pyrid-4-ylthio]-3-cephem-4-carboxylate, trifluoroacetic acid salt

Example 56
(7R)-7-[(Z)-2-(2-aminothiazol-4-yl)-2-(hydroxyimino) acetamido]-3-[3-(2-N-(iminomethyl)amino-3-hydroxypropylthio)pyrid-4-ylthio]-3-cephem-4-carboxylate, trifluoroacetic acid salt

Example 57
(7R)-7-[(Z)-2-(2-aminothiazol-4-yl)-2-(hydroxyimino) acetamido]-3-[3-(2-aminoethylthiomethyl)pyrid-4-ylthio]-3-cephem-4-carboxylate, trifluoroacetic acid salt

Example 58
(7R)-7-[(Z)-2-(2-aminothiazol-4-yl)-2-(hydroxyimino) acetamido]-3-[3-(2-guanidinoethylthiomethyl)pyrid-4-ylthio]-3-cephem-4-carboxylate, trifluoroacetic acid salt

Example 59
(7R)-7-[(Z)-2-(2-aminothiazol-4-yl)-2-(hydroxyimino) acetamido]-3-[3-(2-N-(iminomethyl)aminoethylthiomethyl) pyrid-4-ylthio]-3-cephem-4-carboxylate, trifluoroacetic acid salt

Example 60
(7R)-7-[(Z)-2-(2-aminothiazol-4-yl)-2-(hydroxyimino) acetamido]-3-[3-(2-aminopropylthiomethyl)pyrid-4-ylthio]-3-cephem-4-carboxylate, trifluoroacetic acid salt

Example 61
(7R)-7-[(Z)-2-(2-aminothiazol-4-yl)-2-(hydroxyimino) acetamido]-3-[3-(2-guanidinopropylthiomethyl)pyrid-4-ylthio]-3-cephem-4-carboxylate, trifluoroacetic acid salt

Example 62
(7R)-7-[(Z)-2-(2-aminothiazol-4-yl)-2-(hydroxyimino) acetamido]-3-[3-(2-N-(iminomethyl) aminopropylthiomethyl)pyrid-4-ylthio]-3-cephem-4-carboxylate, trifluoroacetic acid salt

Example 63
(7R)-7-[(Z)-2-(2-aminothiazol-4-yl)-2-(hydroxyimino) acetamido]-3-[3-(2-amino-2-carboxamidoethylthiomethyl) pyrid-4-ylthio]-3-cephem-4-carboxylate, trifluoroacetic acid salt

Example 64
(7R)-7-[(Z)-2-(2-aminothiazol-4-yl)-2-(hydroxyimino) acetamido]-3-[3-(2-guanidino-2-carboxamidoethylthiomethyl)pyrid-4-ylthio]-3-cephem-4-carboxylate, trifluoroacetic acid salt

Example 65
(7R)-7-[(Z)-2-(2-aminothiazol-4-yl)-2-(hydroxyimino) acetamido]-3-[3-(2-N-(iminomethyl)amino-2-carboxamidoethylthiomethyl)pyrid-4-ylthio]-3-cephem-4-carboxylate, trifluoroacetic acid salt

Example 66
(7R)-7-[(Z)-2-(2-aminothiazol-4-yl)-2-(hydroxyimino) acetamido]-3-[3-(2-amino-3-hydroxypropylthiomethyl) pyrid-4-ylthio]-3-cephem-4-carboxylate, trifluoroacetic acid salt

Example 67
(7R)-7-[(Z)-2-(2-aminothiazol-4-yl)-2-(hydroxyimino) acetamido]-3-[3-(2-guanidino-3-hydroxypropylthiomethyl) pyrid-4-ylthio]-3-cephem-4-carboxylate, trifluoroacetic acid salt

Example 68
(7R)-7-[(Z)-2-(2-aminothiazol-4-yl)-2-(hydroxyimino) acetamido]-3-[3-(2-N-(iminomethyl)amino-3-hydroxypropylthiomethyl)pyrid-4-ylthio]-3-cephem-4-carboxylate, trifluoroacetic acid salt

Example 69
(7R)-7-[(Z)-2-(2-amino-5-chlorothiazol-4-yl)-2-(hydroxyimino)acetamido]-3-[3-(2-aminoethylthio)pyrid-4-ylthio]-3-cephem-4-carboxylate, trifluoroacetic acid salt

Example 70
(7R)-7-[(Z)-2-(2-amino-5-chlorothiazol-4-yl)-2-(hydroxyimino)acetamido]-3-[3-(2-guanidinoethylthio) pyrid-4-ylthio]-3-cephem-4-carboxylate, trifluoroacetic acid salt

Example 71
(7R)-7-[(Z)-2-(2-amino-5-chlorothiazol-4-yl)-2-(hydroxyimino)acetamido]-3-[3-(2-N-(iminomethyl) aminoethylthio)pyrid-4-ylthio]-3-cephem-4-carboxylate, trifluoroacetic acid salt

Example 72
(7R)-7-[(Z)-2-(2-amino-5-chlorothiazol-4-yl)-2-(hydroxyimino)acetamido]-3-[3-(2-aminopropylthio)pyrid-4-ylthio]-3-cephem-4-carboxylate, trifluoroacetic acid salt

Example 73
(7R)-7-[(Z)-2-(2-amino-5-chlorothiazol-4-yl)-2-(hydroxyimino)acetamido]-3-[3-(2-guanidinopropylthio) pyrid-4-ylthio]-3-cephem-4-carboxylate, trifluoroacetic acid salt

Example 74
(7R)-7-[(Z)-2-(2-amino-5-chlorothiazol-4-yl)-2-(hydroxyimino)acetamido]-3-[3-(2-N-(iminomethyl)aminopropylthio)pyrid-4-ylthio]-3-cephem-4-carboxylate, trifluoroacetic acid salt

Example 75
(7R)-7-[(Z)-2-(2-amino-5-chlorothiazol-4-yl)-2-(hydroxyimino)acetamido]-3-[3-(2-amino-2-carboxamidoethylthio)pyrid-4-ylthio]-3-cephem-4-carboxylate, trifluoroacetic acid salt

Example 76
(7R)-7-[(Z)-2-(2-amino-5-chlorothiazol-4-yl)-2-(hydroxyimino)acetamido]-3-[3-(2-guanidino-2-carboxamidoethylthio)pyrid-4-ylthio]-3-cephem-4-carboxylate, trifluoroacetic acid salt

Example 77
(7R)-7-[(Z)-2-(2-amino-5-chlorothiazol-4-yl)-2-(hydroxyimino)acetamido]-3-[3-(2-N-(iminomethyl)amino-2-carboxamidoethylthio)pyrid-4-ylthio]-3-cephem-4-carboxylate, trifluoroacetic acid salt

Example 78
(7R)-7-[(Z)-2-(2-amino-5-chlorothiazol-4-yl)-2-(hydroxyimino)acetamido]-3-[3-(2-amino-3-hydroxypropylthio)pyrid-4-ylthio]-3-cephem-4-carboxylate, trifluoroacetic acid salt

Example 79
(7R)-7-[(Z)-2-(2-amino-5-chlorothiazol-4-yl)-2-(hydroxyimino)acetamido]-3-[3-(2-guanidino-3-hydroxypropylthio)pyrid-4-ylthio]-3-cephem-4-carboxylate, trifluoroacetic acid salt

Example 80
(7R)-7-[(Z)-2-(2-amino-5-chlorothiazol-4-yl)-2-(hydroxyimino)acetamido]-3-[3-(2-N-(iminomethyl)amino-3-hydroxypropylthio)pyrid-4-ylthio]-3-cephem-4-carboxylate, trifluoroacetic acid salt

Example 81
(7R)-7-[(Z)-2-(2-amino-5-chlorothiazol-4-yl)-2-(hydroxyimino)acetamido]-3-[3-(2-aminoethylthiomethyl)pyrid-4-ylthio]-3-cephem-4-carboxylate, trifluoroacetic acid salt

Example 82
(7R)-7-[(Z)-2-(2-amino-5-chlorothiazol-4-yl)-2-(hydroxyimino)acetamido]-3-[3-(2-guanidinoethylthiomethyl)pyrid-4-ylthio]-3-cephem-4-carboxylate, trifluoroacetic acid salt

Example 83
(7R)-7-[(Z)-2-(2-amino-5-chlorothiazol-4-yl)-2-(hydroxyimino)acetamido]-3-[3-(2-N-(iminomethyl)aminoethylthiomethyl)pyrid-4-ylthio]-3-cephem-4-carboxylate, trifluoroacetic acid salt

Example 84
(7R)-7-[(Z)-2-(2-amino-5-chlorothiazol-4-yl)-2-(hydroxyimino)acetamido]-3-[3-(2-aminopropylthiomethyl)pyrid-4-ylthio]-3-cephem-4-carboxylate, trifluoroacetic acid salt

Example 85
(7R)-7-[(Z)-2-(2-amino-5-chlorothiazol-4-yl)-2-(hydroxyimino)acetamido]-3-[3-(2-guanidinopropylthiomethyl)pyrid-4-ylthio]-3-cephem-4-carboxylate, trifluoroacetic acid salt

Example 86
(7R)-7-[(Z)-2-(2-amino-5-chlorothiazol-4-yl)-2-(hydroxyimino)acetamido]-3-[3-(2-N-(iminomethyl)aminopropylthiomethyl)pyrid-4-ylthio]-3-cephem-4-carboxylate, trifluoroacetic acid salt

Example 87
(7R)-7-[(Z)-2-(2-amino-5-chlorothiazol-4-yl)-2-(hydroxyimino)acetamido]-3-[3-(2-amino-2-carboxamidoethylthiomethyl)pyrid-4-ylthio]-3-cephem-4-carboxylate, trifluoroacetic acid salt

Example 88
(7R)-7-[(Z)-2-(2-amino-5-chlorothiazol-4-yl)-2-(hydroxyimino)acetamido]-3-[3-(2-guanidino-2-carboxamidoethylthiomethyl)pyrid-4-ylthio]-3-cephem-4-carboxylate, trifluoroacetic acid salt

Example 89
(7R)-7-[(Z)-2-(2-amino-5-chlorothiazol-4-yl)-2-(hydroxyimino)acetamido]-3-[3-(2-N-(iminomethyl)amino-2-carboxamidoethylthiomethyl)pyrid-4-ylthio]-3-cephem-4-carboxylate, trifluoroacetic acid salt

Example 90
(7R)-7-[(Z)-2-(2-amino-5-chlorothiazol-4-yl)-2-(hydroxyimino)acetamido]-3-[3-(2-amino-3-hydroxypropylthiomethyl)pyrid-4-ylthio]-3-cephem-4-carboxylate, trifluoroacetic acid salt

Example 91
(7R)-7-[(Z)-2-(2-amino-5-chlorothiazol-4-yl)-2-(hydroxyimino)acetamido]-3-[3-(2-guanidino-3-hydroxypropylthiomethyl)pyrid-4-ylthio]-3-cephem-4-carboxylate, trifluoroacetic acid salt

Example 92
(7R)-7-[(Z)-2-(2-amino-5-chlorothiazol-4-yl)-2-(hydroxyimino)acetamido]-3-[3-(2-N-(iminomethyl)amino-3-hydroxypropylthiomethyl)pyrid-4-ylthio]-3-cephem-4-carboxylate, trifluoroacetic acid salt

Example 93
(7R)-7-[(Z)-2-(2-aminothiazol-4-yl)-2-(2-fluoroethoxyimino)acetamido]-3-[3-(2-aminoethylthio)pyrid-4-ylthio]-3-cephem-4-carboxylate, trifluoroacetic acid salt

Example 94
(7R)-7-[(Z)-2-(2-aminothiazol-4-yl)-2-(2-fluoroethoxyimino)acetamido]-3-[3-(2-guanidinoethylthio)pyrid-4-ylthio]-3-cephem-4-carboxylate, trifluoroacetic acid salt

Example 95
(7R)-7-[(Z)-2-(2-aminothiazol-4-yl)-2-(2-fluoroethoxyimino)acetamido]-3-[3-(2-N-(iminomethyl)aminoethylthiomethyl)pyrid-4-ylthio]-3-cephem-4-carboxylate, trifluoroacetic acid salt

Example 96
(7R)-7-[(Z)-2-(2-aminothiazol-4-yl)-2-(2-fluoroethoxyimino)acetamido]-3-[3-(2-aminopropylthio)pyrid-4-ylthio]-3-cephem-4-carboxylate, trifluoroacetic acid salt

Example 97
(7R)-7-[(Z)-2-(2-aminothiazol-4-yl)-2-(2-fluoroethoxyimino)acetamido]-3-[3-(2- guanidinopropylthio)pyrid-4-ylthio]-3-cephem-4-carboxylate, trifluoroacetic acid salt

Example 98
(7R)-7-[(Z)-2-(2-aminothiazol-4-yl)-2-(2-fluoroethoxyimino)acetamido]-3-[3-(2-N-(iminomethyl)aminopropylthio)pyrid-4-ylthio]-3-cephem-4-carboxylate, trifluoroacetic acid salt

Example 99
(7R)-7-[(Z)-2-(2-aminothiazol-4-yl)-2-(2-fluoroethoxyimino)acetamido]-3-[3-(2-amino-2-carboxamidoethylthio)pyrid-4-ylthio]-3-cephem-4-carboxylate, trifluoroacetic acid salt

Example 100
(7R)-7-[(Z)-2-(2-aminothiazol-4-yl)-2-(2-fluoroethoxyimino)acetamido]-3-[3-(2-guanidino-2-carboxamidoethylthio)pyrid-4-ylthio]-3-cephem-4-carboxylate, trifluoroacetic acid salt

Example 101
(7R)-7-[(Z)-2-(2-aminothiazol-4-yl)-2-(2-fluoroethoxyimino)acetamido]-3-[3-(2-N-(iminomethyl)amino-2-carboxamidoethylthio)pyrid-4-ylthio]-3-cephem-4-carboxylate, trifluoroacetic acid salt

Example 102
(7R)-7-[(Z)-2-(2-aminothiazol-4-yl)-2-(2-fluoroethoxyimino)acetamido]-3-[3-(2-amino-3-hydroxypropylthio)pyrid-4-ylthio]-3-cephem-4-carboxylate, trifluoroacetic acid salt

Example 103
(7R)-7-[(Z)-2-(2-aminothiazol-4-yl)-2-(2-fluoroethoxyimino)acetamido]-3-[3-(2-guanidino-3-hydroxypropylthio)pyrid-4-ylthio]-3-cephem-4-carboxylate, trifluoroacetic acid salt

Example 104
(7R)-7-[(Z)-2-(2-aminothiazol-4-yl)-2-(2-fluoroethoxyimino)acetamido]-3-[3-(2-N-(iminomethyl)amino-3-hydroxypropylthio)pyrid-4-ylthio]-3-cephem-4-carboxylate, trifluoroacetic acid salt

Example 105
(7R)-7-[(Z)-2-(2-aminothiazol-4-yl)-2-(2-fluoroethoxyimino)acetamido]-3-[3-(2-aminoethylthiomethyl)pyrid-4-ylthio]-3-cephem-4-carboxylate, trifluoroacetic acid salt

Example 106
(7R)-7-[(Z)-2-(2-aminothiazol-4-yl)-2-(2-fluoroethoxyimino)acetamido]-3-[3-(2-guanidinoethylthiomethyl)pyrid-4-ylthio]-3-cephem-4-carboxylate, trifluoroacetic acid salt

Example 107
(7R)-7-[(Z)-2-(2-aminothiazol-4-yl)-2-(2-fluoroethoxyimino)acetamido]-3-[3-(2-N-(iminomethyl)aminoethylthiomethyl)pyrid-4-ylthio]-3-cephem-4-carboxylate, trifluoroacetic acid salt

Example 108
(7R)-7-[(Z)-2-(2-aminothiazol-4-yl)-2-(2-fluoroethoxyimino)acetamido]-3-[3-(2-aminopropylthiomethyl)pyrid-4-ylthio]-3-cephem-4-carboxylate, trifluoroacetic acid salt

Example 109
(7R)-7-[(Z)-2-(2-aminothiazol-4-yl)-2-(2-fluoroethoxyimino)acetamido]-3-[3-(2-guanidinopropylthiomethyl)pyrid-4-ylthio]-3-cephem-4-carboxylate, trifluoroacetic acid salt

Example 110
(7R)-7-[(Z)-2-(2-aminothiazol-4-yl)-2-(2-fluoroethoxyimino)acetamido]-3-[3-(2-N-(iminomethyl)aminopropylthiomethyl)pyrid-4-ylthio]-3-cephem-4-carboxylate, trifluoroacetic acid salt

Example 111
(7R)-7-[(Z)-2-(2-aminothiazol-4-yl)-2-(2-fluoroethoxyimino)acetamido]-3-[3-(2-amino-2-carboxamidoethylthiomethyl)pyrid-4-ylthio]-3-cephem-4-carboxylate, trifluoroacetic acid salt

Example 112
(7R)-7-[(Z)-2-(2-aminothiazol-4-yl)-2-(2-fluoroethoxyimino)acetamido]-3-[3-(2-guanidino-2-carboxamidoethylthiomethyl)pyrid-4-ylthio]-3-cephem-4-carboxylate, trifluoroacetic acid salt

Example 113
(7R)-7-[(Z)-2-(2-aminothiazol-4-yl)-2-(2-fluoroethoxyimino)acetamido]-3-[3-(2-N-(iminomethyl)amino-2-carboxamidoethylthiomethyl)pyrid-4-ylthio]-3-cephem-4-carboxylate, trifluoroacetic acid salt

Example 114
(7R)-7-[(Z)-2-(2-aminothiazol-4-yl)-2-(2-fluoroethoxyimino)acetamido]-3-[3-(2-amino-3-hydroxypropylthiomethyl)pyrid-4-ylthio]-3-cephem-4-carboxylate, trifluoroacetic acid salt

Example 115
(7R)-7-[(Z)-2-(2-aminothiazol-4-yl)-2-(2-fluoroethoxyimino)acetamido]-3-[3-(2-guanidino-3-hydroxypropylthiomethyl)pyrid-4-ylthio]-3-cephem-4-carboxylate, trifluoroacetic acid salt

Example 116
(7R)-7-[(Z)-2-(2-aminothiazol-4-yl)-2-(2-fluoroethoxyimino)acetamido]-3-[3-(2-N-(iminomethyl)amino-3-hydroxypropylthiomethyl)pyrid-4-ylthio]-3-cephem-4-carboxylate, trifluoroacetic acid salt

Example 117
(7R)-7-[(Z)-2-(2-amino-5-chlorothiazol-4-yl)-2-(2-fluoroethoxyimino)acetamido]-3-[3-(2-aminoethylthio)pyrid-4-ylthio]-3-cephem-4-carboxylate, trifluoroacetic acid salt

Example 118
(7R)-7-[(Z)-2-(2-amino-5-chlorothiazol-4-yl)-2-(2-fluoroethoxyimino)acetamido]-3-[3-(2-guanidinoethylthio)pyrid-4-ylthio]-3-cephem-4-carboxylate, trifluoroacetic acid salt

Example 119
(7R)-7-[(Z)-2-(2-amino-5-chlorothiazol-4-yl)-2-(2-fluoroethoxyimino)acetamido]-3-[3-(2-N-(iminomethyl)aminoethylthio)pyrid-4-ylthio]-3-cephem-4-carboxylate, trifluoroacetic acid salt

Example 120
(7R)-7-[(Z)-2-(2-amino-5-chlorothiazol-4-yl)-2-(2-fluoroethoxyimino)acetamido]-3-[3-(2-aminopropylthio)pyrid-4-ylthio]-3-cephem-4-carboxylate, trifluoroacetic acid salt

Example 121
(7R)-7-[(Z)-2-(2-amino-5-chlorothiazol-4-yl)-2-(2-fluoroethoxyimino)acetamido]-3-[3-(2- guanidinopropylthio)pyrid-4-ylthio]-3-cephem-4-carboxylate, trifluoroacetic acid salt Example 122
(7R)-7-[(Z)-2-(2-amino-5-chlorothiazol-4-yl)-2-(2-fluoroethoxyimino)acetamido]-3-[3-(2-N-(iminomethyl)aminopropylthio)pyrid-4-ylthio]-3-cephem-4-carboxylate, trifluoroacetic acid salt Example 123
(7R)-7-[(Z)-2-(2-amino-5-chlorothiazol-4-yl)-2-(2-fluoroethoxyimino)acetamido]-3-[3-(2-amino-2-carboxamidoethylthio)pyrid-4-ylthio]-3-cephem-4-carboxylate, trifluoroacetic acid salt Example 124
(7R)-7-[(Z)-2-(2-amino-5-chlorothiazol-4-yl)-2-(2-fluoroethoxyimino)acetamido]-3-[3-(2-guanidino-2-carboxamidoethylthio)pyrid-4-ylthio]-3-cephem-4-carboxylate, trifluoroacetic acid salt Example 125
(7R)-7-[(Z)-2-(2-amino-5-chlorothiazol-4-yl)-2-(2-fluoroethoxyimino)acetamido]-3-[3-(2-N-(iminomethyl)amino-2-carboxamidoethylthio)pyrid-4-ylthio]-3-cephem-4-carboxylate, trifluoroacetic acid salt Example 126
(7R)-7-[(Z)-2-(2-amino-5-chlorothiazol-4-yl)-2-(2-fluoroethoxyimino)acetamido]-3-[3-(2-amino-3-hydroxypropylthio)pyrid-4-ylthio]-3-cephem-4-carboxylate, trifluoroacetic acid salt Example 127
(7R)-7-[(Z)-2-(2-amino-5-chlorothiazol-4-yl)-2-(2-fluoroethoxyimino)acetamido]-3-[3-(2-guanidino-3-hydroxypropylthio)pyrid-4-ylthio]-3-cephem-4-carboxylate, trifluoroacetic acid salt Example 128
(7R)-7-[(Z)-2-(2-amino-5-chlorothiazol-4-yl)-2-(2-fluoroethoxyimino)acetamido]-3-[3-(2-N-(iminomethyl)amino-3-hydroxypropylthio)pyrid-4-ylthio]-3-cephem-4-carboxylate, trifluoroacetic acid salt Example 129
(7R)-7-[(Z)-2-(2-amino-5-chlorothiazol-4-yl)-2-(2-fluoroethoxyimino)acetamido]-3-[3-(2-aminoethylthiomethyl)pyrid-4-ylthio]-3-cephem-4-carboxylate, trifluoroacetic acid salt Example 130
(7R)-7-[(Z)-2-(2-amino-5-chlorothiazol-4-yl)-2-(2-fluoroethoxyimino)acetamido]-3-[3-(2-guanidinoethylthiomethyl)pyrid-4-ylthio]-3-cephem-4-carboxylate, trifluoroacetic acid salt Example 131
(7R)-7-[(Z)-2-(2-amino-5-chlorothiazol-4-yl)-2-(2-fluoroethoxyimino)acetamido]-3-[3-(2-N-(iminomethyl)aminoethylthiomethyl)pyrid-4-ylthio]-3-cephem-4-carboxylate, trifluoroacetic acid salt Example 132
(7R)-7-[(Z)-2-(2-amino-5-chlorothiazol-4-yl)-2-(2-fluoroethoxyimino)acetamido]-3-[3-(2-aminopropylthiomethyl)pyrid-4-ylthio]-3-cephem-4-carboxylate, trifluoroacetic acid salt Example 133
(7R)-7-[(Z)-2-(2-amino-5-chlorothiazol-4-yl)-2-(2-fluoroethoxyimino)acetamido]-3-[3-(2-guanidinopropylthiomethyl)pyrid-4-ylthio]-3-cephem-4-carboxylate, trifluoroacetic acid salt Example 134
(7R)-7-[(Z)-2-(2-amino-5-chlorothiazol-4-yl)-2-(2-fluoroethoxyimino)acetamido]-3-[3-(2-N-(iminomethyl)aminopropylthiomethyl)pyrid-4-ylthio]-3-cephem-4-carboxylate, trifluoroacetic acid salt Example 135
(7R)-7-[(Z)-2-(2-amino-5-chlorothiazol-4-yl)-2-(2-fluoroethoxyimino)acetamido]-3-[3-(2-amino-2-carboxamidoethylthiomethyl)pyrid-4-ylthio]-3-cephem-4-carboxylate, trifluoroacetic acid salt Example 136
(7R)-7-[(Z)-2-(2-amino-5-chlorothiazol-4-yl)-2-(2-fluoroethoxyimino)acetamido]-3-[3-(2-guanidino-2-carboxamidoethylthiomethyl)pyrid-4-ylthio]-3-cephem-4-carboxylate, trifluoroacetic acid salt Example 137
(7R)-7-[(Z)-2-(2-amino-5-chlorothiazol-4-yl)-2-(2-fluoroethoxyimino)acetamido]-3-[3-(2-N-(iminomethyl)amino-2-carboxamidoethylthiomethyl)pyrid-4-ylthio]-3-cephem-4-carboxylate, trifluoroacetic acid salt Example 138
(7R)-7-[(Z)-2-(2-amino-5-chlorothiazol-4-yl)-2-(2-fluoroethoxyimino)acetamido]-3-[3-(2-amino-3-hydroxypropylthiomethyl)pyrid-4-ylthio]-3-cephem-4-carboxylate, trifluoroacetic acid salt Example 139
(7R)-7-[(Z)-2-(2-amino-5-chlorothiazol-4-yl)-2-(2-fluoroethoxyimino)acetamido]-3-[3-(2-guanidino-3-hydroxypropylthiomethyl)pyrid-4-ylthio]-3-cephem-4-carboxylate, trifluoroacetic acid salt Example 140
(7R)-7-[(Z)-2-(2-amino-5-chlorothiazol-4-yl)-2-(2-fluoroethoxyimino)acetamido]-3-[3-(2-N-(iminomethyl)amino-3-hydroxypropylthiomethyl)pyrid-4-ylthio]-3-cephem-4-carboxylate, trifluoroacetic acid salt Thus, it will be appreciated that the compounds, methods and compositions of the invention are effective against various β-lactam resistant strains of bacteria which pose an increasing health risk to society.

Although certain embodiments and examples have been used to describe the present invention, it will be apparent to those skilled in the art that changes to the embodiments and examples shown may be made without departing from the scope or spirit of the invention.

Those references not previously incorporated herein by reference, including both patent and non-patent references, are expressly incorporated herein by reference for all purposes.

Other embodiments are within the following claims.

What is claimed:
1. A compound of the formula:

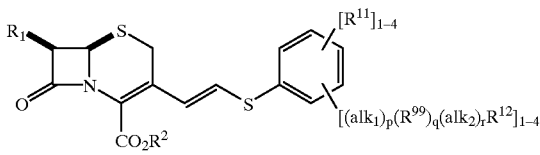

or a pharmaceutically acceptable salt thereof wherein
R$^1$ is selected from the group consisting of

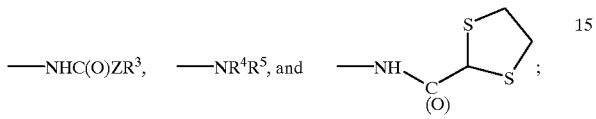

Z is selected from the group consisting of —CH$_2$(X)$_m$—, —C(NOR$^6$)—, —CH(OR$^7$)—, —C(CHCO$_2$R$^8$)— and —CH(NR$^9$R$^{10}$)—;
X is selected from the group consisting of oxygen and sulfur;
m is selected from the group consisting of 0 and 1;
R$^3$ is selected from the group consisting of cyano, optionally substituted alkyl, optionally substituted aryl, optionally substituted heterocycle, optionally substituted heteroaralkyl and (CH$_2$)$_n$T,
wherein said alkyl is optionally substituted with substituents selected from the group consisting of hydroxyl, bromo, fluoro, chloro, iodo, mercapto, cyano, alkylthio, carboxyl, alkoxycarbonyl, alkenyl, nitro, amino, alkoxyl, carboxamido, isothioureido, amidino, and guanidino;
wherein said aryl is substituted with substituents selected from the group consisting of hydroxyl, bromo, fluoro, chloro, iodo, mercapto, cyano, alkylthio, carboxyl, alkoxycarbonyl, alkenyl, nitro, amino, alkoxyl, and carboxamido;
wherein said heterocycle is selected from, the group consisting of furyl, thienyl, imidazolyl, indolyl, pyridinyl, thiadiazolyl, thiazolyl, piperazinyl, dibenzfuranyl, dibenzthienyl, pyrimidinyl, and pyridazinyl; and
wherein said heterocycle and said heteroaryl portion of said heteroaralkyl is each independently and optionally substituted with substituents selected from the group consisting of hydroxyl, bromo, fluoro, chloro, iodo, mercapto, cyano, alkylthio, carboxyl, oxo, alkoxycarbonyl, alkenyl, nitro, amino, alkoxyl, and carboxamido;
n is 1 to 6,
T is selected from the group consisting of amino, amidino (C- or N-linked), guanidino, and isothioureido, optionally substituted by alkyl, aryl, hydroxyl, or amino;
R$^4$–R$^7$ are independently selected from the group consisting of hydrogen, optionally substituted alkyl, optionally substituted aryl and, acyl;
wherein said alkyl is optionally substituted with substituents selected from the group consisting of hydroxyl, bromo, fluoro, chloro, iodo, mercapto, cyano, alkylthio, carboxyl, alkoxycarbonyl, alkenyl, nitro, amino, alkoxyl, carboxamido, isothioureido, amidino, and guanidino; and
wherein said aryl is substituted with substituents selected from the group consisting of hydroxyl, bromo, fluoro, chloro, iodo, mercapto, cyano, alkylthio, carboxyl, alkoxycarbonyl, alkenyl, nitro, amino, alkoxyl, and carboxamido;
R$^8$ is selected from the group of hydrogen, optionally substituted alkyl, optionally substituted aryl, and acyl;
wherein said alkyl is optionally substituted with substituents selected from the group consisting of hydroxyl, bromo, fluoro, chloro, iodo, mercapto, cyano, alkylthio, carboxyl, alkoxycarbonyl, alkenyl, nitro, amino, alkoxyl, carboxamido, isothioureido, amidino, and guanidino; and
wherein said aryl is substituted with substituents selected from the group consisting of hydroxyl, bromo, fluoro, chloro, iodo, mercapto, cyano, alkylthio, carboxyl, alkoxycarbonyl, alkenyl, nitro, amino, alkoxyl, and carboxamido,
R$^9$ and R$^{10}$ are selected independently from the group consisting of hydrogen, optionally substituted alkyl, acyl, and optionally substituted heterocyclecarbonyl;
wherein said alkyl is optionally substituted with substituents selected from the group consisting of hydroxyl, bromo, fluoro, chloro, iodo, mercapto, cyano, alkylthio, carboxyl, alkoxycarbonyl, alkenyl, nitro, amino, alkoxyl, carboxamido, isothioureido, amidino, and guanidino;
and wherein the heterocycle portion of said heterocyclecarbonyl is optionally substituted with substituents selected from the group consisting of hydroxyl, bromo, fluoro, chloro, iodo, mercapto, cyano, alkylthio, carboxyl, oxo, alkoxycarbonyl, alkenyl, nitro, amino, alkoxyl, and carboxamido;
R$^2$ is selected from the group consisting of hydrogen, optionally substituted alkyl, optionally substituted alkenyl, optionally substituted aryl, optionally substituted heterocycle, optionally substituted aralkyl, optionally substituted heteroaralkyl, and trialkylsilyl; or when R$^{12}$ is a cationic group R$^2$ is not present and the CO$_2$ group to which it would be attached bears a negative charge;
wherein said alkyl and said alkenyl are each independently and optionally substituted with substituents selected from the group consisting of hydroxyl, bromo, fluoro, chloro, iodo, mercapto, cyano, alkylthio, carboxyl, alkoxycarbonyl, nitro, amino, alkoxyl, carboxamido, isothioureido, amidino, and guanidino;
wherein said aryl and said aryl portion of said aralkyl is each independently and optionally substituted with substituents selected from the group consisting of hydroxy, bromo, fluoro, chloro, iodo, mercapto, cyano, alkylthio, carboxyl, alkoxycarbonyl, nitro, amino, alkoxyl, and carboxamido;
wherein said heterocycle is selected from the group consisting of furyl, thienyl, imidazolyl, indolyl, pyridinyl, thiadiazolyl, thiazolyl, piperazinyl, dibenzfuranyl, dibenzthienyl, pyrimidinyl, and pyridazinyl; and
wherein said heterocycle and said heteroaryl portion of said heteroaralkyl is each independently and optionally substituted with substituents selected from the group consisting of hydroxyl, bromo, fluoro, chloro, iodo, mercapto, cyano, alkylthio, carboxyl, oxo, alkoxycarbonyl, alkenyl, nitro, amino, alkoxyl, and carboxamido;
R$^{11}$ is selected from the group consisting of hydrogen, halogen, optionally substituted alkyl, optionally substituted alkoxy, hydroxyl, amino, cyano, optionally substituted hydroxyalkyl, optionally substituted carboxamidoalkyl, and optionally substituted aminoalkyl;

wherein said alkyl, and said alkyl portion of said alkoxy, hydroxyalkyl, carboxamidoalkyl, and aminoalkyl is each independently and optionally substituted with substituents selected from the group consisting of bromo, fluoro, chloro, iodo, mercapto, cyano, alkylthio, carboxyl, alkenyl, nitro, isothioureido, amidino, and guanidino;

$alk_1$ and $alk_2$ are alkylene groups and are independently and optionally substituted with a substitutent selected from the group consisting of alkyl, hydroxyl, optionally substituted amino, alkoxy, hydroxyalkyl, and optionally substituted carboxamide;

p is 0, 1, or 2;

$R^{99}$ is selected from the group consisting of sulfur, SO, $SO_2$, NH, N-alkyl, oxygen, C=C (cis or trans), and C≡C;

q is 1;

r is 0, 1, 2 or 3;

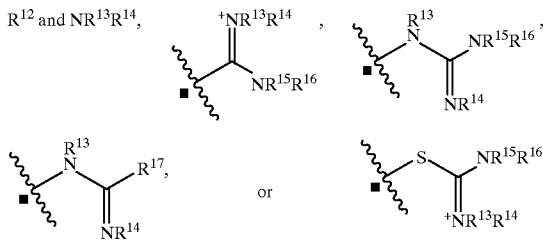

$R^{13}$–$R^{16}$ are independently selected from the group consisting of hydrogen, hydroxy, amino, amidino, optionally substituted alkyl, cycloalkyl, acyl, aminoacyl, and phosphoryl;

wherein said alkyl is optionally substituted with substituents selected from the group consisting of bromo, fluoro, chloro, iodo, mercapto, cyano, alkylthio, heterocycle, aryl, heteroaryl, nitro, alkoxyl, carboxamido, isothioureido, amidino, and guanidino;

$R^{17}$ is hydrogen or optionally substituted alkyl;

wherein said alkyl is optionally substituted with substituents selected from the group consisting of bromo, fluoro, chloro, iodo, mercapto, cyano, alkylthio, heterocycle, aryl, heteroaryl, nitro, alkoxyl, carboxamido, isothioureido, amidino, and guanidino.

2. The compound or salt of claim 1, wherein $R^1$ is —NHC(O)$ZR^3$.

3. The compound or salt of claim 2, wherein $R^3$ is optionally substituted aryl or an optionally substituted heterocycle.

4. The compound or salt of claim 3, wherein $R^3$ is selected from the group consisting of optionally substituted phenyl, optionally substituted thienyl, optionally substituted furanyl, 2-aminothiazolyl, 2-aminothiazol-4-yl, 2-amino-5-chlorothiazol-4-yl, and 2-aminothiadiazol-4-yl.

5. The compound of claim 4, wherein Z is —C(NOR$^6$)—, and $R^6$ is hydrogen.

6. The compound or salt of claim 5, wherein $R^3$ is selected from the group consisting of phenyl, 2-thienyl, 2-furyl, 2-aminothiazol-4-yl, 2-amino-5-chlorothiazol-4-yl, and 2-aminothiadiazol-4-yl.

7. The compound or salt of claim 6, wherein $R^3$ is 2-aminothiazol-4-yl or 2-amino-5-chlorothiazol-4-yl.

8. A method of treating a mammal suffering from a methicillin-resistant, vancomycin-resistant, or ampicillin-resistant bacterial infection, comprising administering to such mammal a therapeutically effective amount of a compound or salt of any one of claims 1–7.

9. The method of claim 8, wherein said mammal is infected with a methicillin-resistant Staphylococcal or ampicillin-resistant Enterococcal organism.

10. An antibacterial composition for treating a methicillin-resistant, vancomycin-resistant, or ampicillin-resistant bacterial infection, comprising a therapeutically effective amount of a compound or salt of any one of claims 1–7 in a pharmaceutically acceptable carrier.

11. The composition of claim 10, wherein said infected is caused by a methicillin-resistant Staphylococcal or ampicillin-resistant Enterococcal organism.

* * * * *